United States Patent [19]
Ellsworth et al.

[11] Patent Number: 5,840,751
[45] Date of Patent: Nov. 24, 1998

[54] 5,6-DIHYDROPYRONE DERIVATIVES AS PROTEASE INHIBITORS AND ANTIVIRAL AGENTS

[75] Inventors: Edmund Lee Ellsworth, Brighton; Elizabeth Lunney, Ann Arbor; Bradley Dean Tait, Canton, all of Mich.

[73] Assignee: Warner-Lambert Company, Morris Plains, N.J.

[21] Appl. No.: 319,820

[22] Filed: Oct. 12, 1994

Related U.S. Application Data

[63] Continuation-in-part of Ser. No. 155,443, Nov. 19, 1993, abandoned.

[51] Int. Cl.$^6$ ............ A61K 31/35; A61K 31/415; A61K 31/44; A61K 31/505
[52] U.S. Cl. ............ 514/460; 514/256; 514/269; 514/336; 514/397; 549/292; 549/417; 548/311.1; 546/268; 544/298; 544/315
[58] Field of Search ............ 549/292, 417; 514/256, 269, 336, 397, 460; 546/268; 548/311.1; 544/298, 315

[56] References Cited

U.S. PATENT DOCUMENTS

| | | | |
|---|---|---|---|
| 3,206,476 | 9/1965 | Collins | 549/292 |
| 3,818,046 | 6/1974 | Harris et al. | 549/292 |
| 3,931,235 | 1/1976 | Harris et al. | 549/292 |

FOREIGN PATENT DOCUMENTS

| | | |
|---|---|---|
| 0278742 | 8/1988 | European Pat. Off. . |
| 3-227923 | 10/1991 | Japan . |
| 3227923-A | 10/1991 | Japan . |
| 89/07939 | 9/1989 | WIPO . |
| 8907939 | 9/1989 | WIPO . |
| 93/10645 | 11/1992 | WIPO . |
| 94111361 | 5/1994 | WIPO . |
| 94118188 | 8/1994 | WIPO . |

OTHER PUBLICATIONS

S. Thaisrivongs, et al., *J. Med. Chem.*, 1994, 37, 3200–3204.
M. Ruwart, et al., *American Association of Pharmaceutical Scientists Meeting—Abstract IPDD 7290*, Nov. 6–10, 1994, San Diego.
D. Richman, "Control of Virus Diseases," *45th Symposium of the Society for General Microbiology*, 1990, 261–313.
H. Toh, et al., *Nature*, 1985, 315:691.
J. Kay, et al., *Biochim. Biophys. Acta* 1: 1990, 1048.
C. Cameron, et al., *J. Biological Chem.* 168, 1993, 11711–720.
M. Graves, *Structure and Function of the Aspartic Protease* 1991, 395–405.
C. Peng, et al., *J. Virol.*, 63: 1989, 2550–2556.
N. Kohl, et al., *Proc. Nat. Acad. Sci. USA*, 85:1988, 4689–90.
J.C. Craig, et al, *Antiviral Research*, 16:1991, 295–305.
A.G. Tomasselli, et al., *Chimica Oggi*, 9: 1991, 6–27.
T. Meek, *J. Enzyme Inhibition*, 6: 1992, 65–98.
R. Nagorny, et al, *AIDS*, 7:1993, 129–130.
D.P. Fairlie, et al., *Biochem. Biophys. Res. Comm.*, 188: 1992, 631–637.

*Primary Examiner*—Amelia Owens
*Attorney, Agent, or Firm*—Elizabeth M. Anderson

[57] ABSTRACT

The present invention relates to novel 5,6-dihydropyrone derivatives and related structures which potently inhibit the HIV aspartyl protease blocking HIV infectivity. The 5,6-dihydropyrone derivatives are useful in the development of therapies for the treatment of bacterial and viral infections and diseases, including AIDS. The present invention is also directed to methods of synthesis of multifunctionalized 5,6-dihydropyrones and of related structures.

23 Claims, No Drawings

5,6-DIHYDROPYRONE DERIVATIVES AS PROTEASE INHIBITORS AND ANTIVIRAL AGENTS

This application is a CIP of 8/155,443 filed Nov. 19, 1993 now abandoned.

1. FIELD OF THE INVENTION

The present invention relates to 5,6-dihydropyrone derivatives that are inhibitors of aspartyl proteases, in particular the aspartyl proteases found in retroviruses including Human Immunodeficiency Virus (HIV). The 5,6-dihydropyrones are expected to have utility as antiviral agents, for the treatment of infection caused by HIV or other retroviruses employing aspartyl proteases, and to be useful in the treatment of diseases caused by the retroviruses, including AIDS.

2. BACKGROUND OF THE INVENTION

Acquired Immunodeficiency Syndrome (AIDS) was coined in 1982 to describe the clinical manifestations of immunodeficiency. The etiological agent of AIDS was later associated with a retrovirus, Human Immunodeficiency Virus (HIV), from the lentivirus subfamily. At least two infectious strains of HIV have been identified, HIV-1 and HIV-2. Here, HIV will be used as a general term describing all strains and mutants of the Human Immunodeficiency Virus. The detailed study of HIV has given rise to many approaches to antiviral drug development including inhibition of the viral aspartyl protease (D. Richman, *Control of Virus Diseases*, 45th Symposium of the Society for General Microbiology, 261–313 (1990)).

Aspartyl proteases have been found in many retroviruses including the Feline Immunodeficiency Virus (FIV), the Myeloblastosis Associated Virus (MAV), HIV, and the Rous Sarcoma Virus (RSV) [H. Toh et al. *Nature*, 315: 691 (1985); J. Kay, B. M. Dunn, *Biochim. Biophys. Acta,* 1: 1048 (1990); C. Cameron, *J. Biological Chem.,* 168: 11711–720 (1993)]. Since there are structural similarities among the known retroviral proteases, compounds which inhibit the HIV protease may well inhibit other retroviral proteases.

HIV aspartyl protease is responsible for post-translational processing of viral precursor polyproteins such as pol and gag. (M. Graves, *Structure and Function of the Aspartic Proteases,* 395–405 (1991)). Cleavage of these polyproteins is essential for maturation of the virus, since the proteolytic activity necessary for polyprotein processing cannot be provided by host cellular enzymes. An important finding has been that viruses which lack this protease, or contain a mutant which is a defective protease, lack infectivity [C. Ping et al., *J. Virol,* 63: 2550–556 (1989) and N. Kohl et al., *Proc. Nati. Acad. Sci. USA,* 85: 4686–90 (1987)]. Thus, a selective HIV protease inhibitor has been shown to inhibit viral spread and the production of cytopathic effects in cultures of acutely infected cells (J. C. Craig, *Antiviral Research,* 16: 295–305 (1991)). For this reason, inhibition of HIV protease is believed to be a viable approach to antiviral therapy.

HIV protease inhibitors have been extensively reviewed (see for example A. Tomasselli et al., *Chimica Oggi,* 6–27 20 (1991) and T. Meek, *J. Enzyme Inhibition* 6: 65–98 (19.92)). However, the majority of these inhibitors are peptides and thus unsuitable as drugs, due to the well known pharmacological deficiencies exhibited by most peptide drugs (biliary excretion, low bioavailability and stability in physiological milieu, etc.) Nonpeptidic inhibitors of HIV protease are thus very important, since these may lead to useful therapeutic agents.

Hei 3-227923 claimed coumarins with anti-HIV activity. However, only 4-hydroxycoumarin was specifically described without discussion of mechanism of action.

World Patent 89/07939 claimed eight coumarin derivatives as HIV reverse transcriptase inhibitors with potential antiviral activity. These derivatives are hexachlorocoumarin, 7-acetoxycoumarin, and the structures shown below.

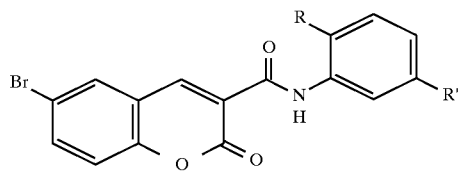

R = H, R' = Cl; R = H, R' = CF₃; R = R' = Cl

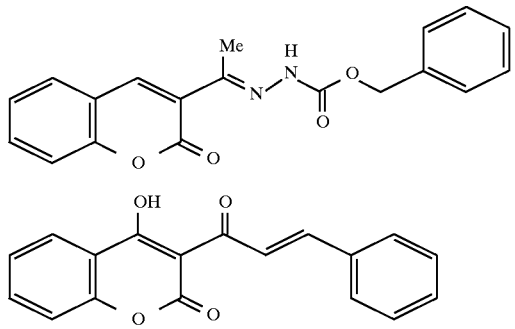

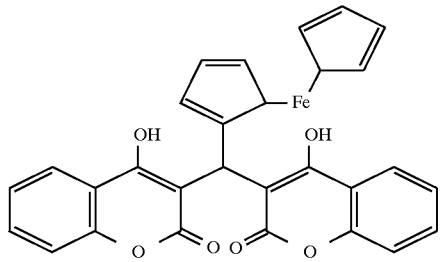

Warfarin (3-(α-acetonylbenzyl)-4-hydroxycoumarin), shown below, was reported by R. Nagorny et al. in *AIDS* 7: 129–130 (1993) as inhibiting cell-free and cell-mediated HIV infection. However, Warfarin was the only analog pyrone studied and its mechanism of action in HIV inhibition was not specified.

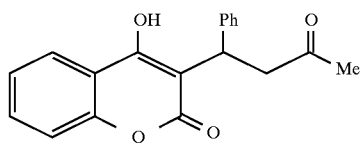

Selected flavones, structurally different from the 5,6-dihydropyrones of the present invention, were reported by Fairli et al., (*Biochem. Biophys. Res. Comm.,* 188: 631–637, (1992)) to be inhibitors of HIV-1 protease. These compounds are shown below.

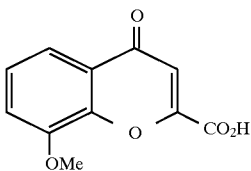

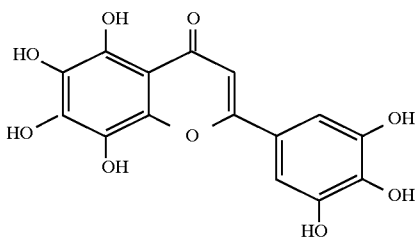

U.S. Pat. No. 3,206,476 describes several pyrones, specifically 3-substituted-4-hydroxy-6-aryl-2-pyrones, as antihypertensive agents. However, the range of substituents at the 3-position of these heterocycles is limited to halo and amino groups and alkanoylamino derivatives.

U.S. Pat. No. 3,818,046 describes several pyrone derivatives, specifically 4-hydroxypyrones with sulfur-containing carbon chains at the 3-position, as growth stunters and antimicrobial agents. These pyrones are substituted as follows: R=Me; M=H or alkali metal; and R'=H, alkyl, phenyl, halophenyl, nitrophenyl, lower alkylphenyl, benzyl, phenethyl, naphthylmethyl, halobenzyl, lower alkylbenzyl, nitrobenzyl, propargyl, allyl, cyclohexyl, lower alkyl, lower thioalkyl, or adamantyl; and n=0 to 2.

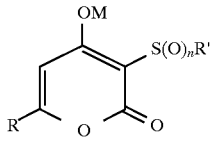

R = Me

A process for preparing the pyrones shown above is claimed in U.S. Pat. No. 3,931,235.

EP 278742 describes several cyclic 2-benzoyl-1,3-diones with herbicidal activity. All of these compounds possess 3-benzoyl substituents. Their structures, in the keto tautomeric forms, are shown below:

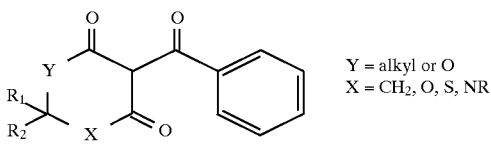

Y = alkyl or O
X = CH₂, O, S, NR

3. SUMMARY OF THE INVENTION

The present invention is based in great part on the extraordinary discovery of the inventors that novel 5,6-dihydropyrone derivatives and related compounds, selected from a broad spectrum of tailored molecular structures, potently inhibit the HIV aspartyl protease blocking infection by HIV. The present invention is also based on the insights of the applicants regarding the mechanism of action of antiviral drugs, especially as revealed by their studies on structure-activity relationships characteristic of anti-HIV compounds that include 5,6-dihydropyrone derivatives.

The invented 5,6-dihydropyrones are expected to be extremely useful in the development of treatments for infections caused by viruses, especially by retroviruses that rely on aspartyl protease activities for replication and infectivity. One such retrovirus is HIV. For this reason, the antiviral 5,6-dihydropyrones are also expected to be very useful in the treatment of diseases and syndromes associated with viral pathogens. One such syndrome is AIDS.

Efficient syntheses of the biologically active 5,6-dihydropyrones involving either de novo assemblies of the 5,6-dihydropyrone nucleus or modifications of suitably functionalized 5,6-dihydropyrones, are disclosed. Furthermore, many working examples outlining the preparation of specific 5,6-dihydropyrones whose structures contain the desired functional groups in proper geometric arrangements are given.

The testing of specific 5,6-dihydropyrones as inhibitors of the HIV aspartyl protease, based on the study of the hydrolysis of an undecapeptide enzyme substrate, and the testing of the 5,6-dihydropyrones as inhibitors of viral growth and infectivity, based on the study of infection of H9 cell lines by the HIV-1$_{iiib}$ strain, are also disclosed. Striking enzyme inhibitions, at nanomolar levels, with corresponding anti-HIV activities were observed.

The present inventors contemplate the preparation of pharmaceutically useful antiviral compositions comprising one or more of the invented 5,6-dihydropyrones and related compounds and a pharmaceutically acceptable carrier. They also contemplate the use of these compositions, alone or in combination with other antiviral treatments, in the treatment of infections and diseases caused by retroviruses, including AIDS.

The present inventors contemplate the preparation of pharmaceutically useful antibacterial compositions cmprising one or more of the invented 5,6 dihydropyrones and related compounds and a pharmaceutically acceptable carrier.

The present invention relates to compounds or the pharmaceutically acceptable salts thereof of formula 1, shown below,

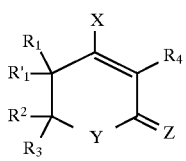

1 wherein
X is $OR_5$, $NHR_5$, $CH_2OR_5$, $CO_2R_6$, or $SR_5$, wherein $R_5$ is $R_6$ or $COR_6$ wherein $R_6$ is independently H, a straight chain alkyl group containing 1 to 6 carbon atoms, a branched or cyclic alkyl group containing 3 to 7 carbon atoms, an alkylcycloalkyl of 5–9 carbon atoms, benzyl, phenyl or a heterocycle;
Z is O or S;
Y is O, S, $C(R_6)_2$, NF, or NR6;
$R_1$ and $R_1'$ are each independently $[CH_2]_{n1}$—$[W_1]_{n2}$—$[Ar]_{n2}$—$[CH_2]_{n3}$—$[W_2]_{n4}$—$R_7$;
$R_2$ is independently selected from the group of structures from which $R_1$ is selected with the proviso that if $W_1$ is a heteroatom n1 is an integer of from 1 to 4;
$R_3$ is independently selected from the group of structures from which $R_1$ is selected with the proviso that if $W_1$ is a heteroatom n1 is an integer of from 1 to 4;

$R_2$ and $R_3$ may be taken together to form an unsubstituted or substituted 3-, 4-, 5-, 6-, or 7-membered ring, wherein the substituents are one or more of the $R_7$ groups listed below;

$R_4$ is $[CH_2]_{n1}-[W_3]_{n2}-[CH_2]_{n3}-[W_4]_{n4}-[Ar]_{n2}-[CH_2]_{n3}-[W_2]_{n4}-R_7$;

n1, n2, n3, n4, and n5 are independently integers of from 0 to 4, 0 to 1, 0 to 4, 0 to 1, and 0 to 2, respectively;

$W_1$, $W_2$, and $W_4$ are independently O, OCONR$_7$, S(O)$_5$, CO, C(=NR$_7$)NR$_7$, CR$_7$=CR$_7$, C≡C, NR$_7$, CS, C=N—R$_7$, C=NOR$_7$, NR$_7$SO$_2$, SO$_2$NR$_7$, C=C(R$_7$)$_2$, CR$_7$N(R$_7$)$_2$, CR$_7$OR$_7$, C(R$_7$)$_2$, NCO$_2$R$_7$, NR$_7$CO$_2$, CO$_2$, NCON(R$_7$)$_2$, NR$_7$CONR$_7$, NCOR$_7$, NR$_7$CO, or CONR$_7$;

$W_3$ is independently selected from the group of structures from which $W_1$ is selected, with the further limitation that if n1 in $R_4$ is zero, that $W_3$ is selected from the group of structures consisting of —Co, —CR$_7$=CR$_7$, —C≡C, —CS, —C=N—R$_7$, —C=N—R$_7$, —C=NOR$_7$, —CR$_7$N(R$_7$)$_2$, —C=C(R$_7$)$_2$, —CR$_7$OR$_7$, —C(R$_7$)$_2$, —CO$_2$, and —CONR$_7$, with the left hyphen denoting the point of attachment to the hydropyrone ring;

$R_7$ is independently H, Ar, a straight or branched alkyl or alkenyl group containing from 1 to 6 carbon atoms, or two $R_7$'s can be taken together to form a ring of 3–7 atoms, or a substituted derivative thereof wherein the substituents are one or more of CO$_2$R$_6$, COR$_6$, CON(R$_6$)$_2$, NR$_6$CON(R$_6$)$_2$, NR$_6$COR$_6$, OR$_6$, S(O)$_{n5}$R$_6$, N(R$_6$)$_2$, Cl, Br, F, CF$_3$, Ar, OAr, or S(O)$_{n5}$Ar;

Ar is independently phenyl, naphthyl, a 5- or 6- membered heterocycle containing 1 to 4 heteroatoms, a cycloalkyl containing 3 to 6 atoms, a fused ring system containing 8-10 atoms, or a substituted derivative thereof wherein the substituents are of F, Cl, Br, CN, NO$_2$, (CH$_2$)$_{n6}$R$_6$, (CH$_2$)$_{n6}$C(Me)=CH$_2$, (CH$_2$)$_{n6}$N(R$_6$)$_2$, (CH$_2$)$_{n6}$NR$_6$CON(R$_6$)$_2$, (CH$_2$)$_{n6}$NR$_6$COR$_6$, (CH$_2$)$_{n6}$OR$_6$, (CH$_2$)$_{n6}$OCOR$_6$, (CH$_2$)$_{n6}$OCON(R$_6$)$_2$, (CH$_2$)$_{n6}$CO$_2$R$_6$, (CH$_2$)$_{n6}$CON(R$_6$)$_2$, (CH$_2$)$_{n6}$COR$_6$, CF$_3$, (CH$_2$)$_{n6}$S(O)$_{n5}$R$_6$, OCH$_2$O, or O(CH$_2$)$_2$O; and n6 is independently an integer of from 0 to 3.

More preferred compounds of the present invention are those of formula 1 wherein X is OR$_5$, wherein R$_5$ is H or COR$_6$ wherein R$_6$ is as defined above;

Z is O;

Y is O, S, or CH$_2$;

$R_1$ and $R_1'$ are independently H, F, (CH$_2$)$_{n1}$CO$_2$R$_6$, (CH$_2$)$_{n1}$OR$_6$, or (CH$_2$)$_{n1}$CON(R$_6$)$_2$;

$R_2$ is $[CH_2]_{n1}-[W_1]_{n2}-[Ar]_{n2}-[CH_2]_{n3}-[W_2]_{n4}-R_7$ with the proviso that if $W_1$ is a heteroatom n1 is an integer of from 1 to 4;

$R_3$ is independently selected from the group of structures from which $R_2$ is selected;

$R_2$ and $R_3$ can be part of a 5-, 6-, or 7-membered ring optionally substituted by groups selected from the group of structures from which $R_7$ is selected;

$R_4$ is $[CH_2]_{n1}-[W_3]_{n2}-[CH_2]_{n3}-[W_4]_{n4}-[Ar]_{n2}-[CH_2]_{n3}-[W_2]_{n4}-R_7$;

n1, n2, n3, n4, and n5 are as defined above;

$W_1$ and $W_4$ are independently O, S(O)$_{n5}$, CO, CR$_7$=CR$_7$, NR$_7$, CR$_7$OR$_7$, C(R$_7$)$_2$, NR$_7$CO$_2$, CO$_2$, NR$_7$CONR$_7$, CONR$_7$ or NR$_7$CO;

$W_2$ is as defined above;

$W_3$ is CR$_7$OR$_7$, C(R$_7$)$_2$, or CONR$_7$;

R7 is as defined above;

Ar is as defined above; and n6 is as defined above.

Even more preferred compounds of the present invention are those of formula 1 wherein X is OH;

Z is O;

Y is O or CH$_2$;

$R_1$ and $R_1'$ are H;

$R_2$ is $[CH_2]_{n1}-[W_1]_{n2}-[Ar]_{n2}-[CH_2]_{n3}-[W_2]_{n4}-R_7$ with the proviso that if $W_1$ is a heteroatom n1 is an integer of from 1 to 4;

$R_2$ and $R_3$ can be part of a 5-, 6-, or 7-membered ring structure optionally substituted by groups selected from the group from which $R_7$ is selected;

$R_4$ is $[CH_2]_{n1}-[W_3]_{n2}-[Ch_2]_{n3}-[W_4]_{n4}-[Ar]_{n2}-[CH_2]_{n3}-[W_2]_{n4}-R_7$;

n1, n2, n3, n4, and n5 are as defined above;

$W_1$ is O, S(O)$_{n5}$, NR$_7$, CONR$_7$ or C(R$_7$)$_2$;

$W_2$ is as defined above;

$W_3$ is C(R$_7$)$_2$;

$W_4$ is independently CR$_7$=CR$_7$, NR$_7$CONR$_7$, C(R$_7$)$_2$, NR$_7$CO, CO, or CO$_2$;

$R_6$, is as defined above;

$R_7$, is as defined above;

Ar is as defined above; and n6 is as defined above.

still more preferred are compounds of formula 1 wherein

X is OH;

Z is O;

Y is O;

$R_1$, and $R_1'$ are H;

$R_2$ is CH$_2$—Ar—(CH$_2$)$_{n3}$—[W$_2$]$_{n4}$—R$_7$, CH$_2$—CH$_2$—Ar—(CH$_2$)$_{n3}$—[W$_2$]$_{n4}$—R$_7$, CH$_2$OAr—(CH$_2$)$_{n3}$—[W$_2$]$_{n4}$—R$_7$, cyclopentylmethyl, -(CH$_2$)$_4$—C(=O)—N(R$_7$)$_2$, cyclohexylmethyl, 2-(2- or 3-tetrahydrofuranyl)ethyl, 2-(2- or 3-furanyl)ethyl, propyl, butyl, iso-butyl, pentyl, iso-pentyl, 2-(cyclopropyl)ethyl, (CH$_2$)$_2$C(CH$_3$)=CH$_2$, Ar—(CH$_2$)$_{n3}$-[W$_2$]$_{n4}$—R$_7$, phenyl, or 2-, 3-, or 4-pyridyl;

$R_3$ is Ar—(CH$_2$)$_{n3}$—[W$_2$]$_{n4}$—R$_7$, phenyl, cyclopentyl, cyclohexyl, 2- or 3-furanyl, 2- or 3-thienyl, 2-, 3- or 4-pyridyl, isobutyl, pentyl, CH$_2$—CH$_2$—Ar, or isopentyl;

$R_2$ and $R_3$ can be part of an unsubstituted or substituted 5-, 6-, or to 7-membered ring structure where the substituents are independently one or more of those listed for $R_7$ above;

$R_4$ is as defined above for the even more preferreed compounds of Formula 1;

n1, n2, n3, n4, and n5 are as defined above;

$W_2$, $W_3$ and $W_4$ are as defined for the even more preferred compounds of the invention above;

$R_6$ is as defined above;

$R_7$ is as defined above;

Ar is as defined above; and n6 is as defined above.

Some of the most preferred compounds of the present invention are included in the following:

5,6-Dihydro-4-hydroxy-6-phenyl-3-[(phenylmethyl)thio-2H]-pyran-2-one;

5,6-Dihydro-4-hydroxy-6-phenyl-3-[(2-phenylethyl)thio]-2H-pyran-2-one;

5,6-Dihydro-4-hydroxy-6-phenyl-3-[(3-phenylpropyl)thio]-2H-pyran-2-one;

5,6-Dihydro-4-hydroxy-6-phenyl-3-[(2-phenoxyethyl)thio]-2H-pyran-2-one;

5,6-Dihydro-4-hydroxy-6-(2-methylpropyl)-6-phenyl-3-[(phenylmethyl)thio]-2H-pyran-2-one;

5,6-Dihydro-4-hydroxy-6-(2-methylpropyl)-6-phenyl-3-[(2-phenylethyl)thio]-2H-pyran-2-one;

5-(3-Chlorophenyl)-2-[(2-phenylethyl)thio]-1,3-cyclohexanedione;

5,6-Dihydro-4-hydroxy-6-(4-methoxyphenyl)-3-[(phenylmethyl)thio]-2H-pyran-2-one;

5,6-Dihydro-4-hydroxy-6-(4-methylthiophenyl)-3-[(phenylmethyl)thio]-2H-pyran-2-one;

5,6-Dihydro-4-hydroxy-6-(4-methylphenyl)-3-[(phenylmethyl)thio]-2H-pyran-2-one;

5,6-Dihydro-4-hydroxy-6-[4-(1,1-dimethylethyl)phenyl]-3-[(phenylmethyl)thio]-2H-pyran-2-one;

6-(4-Chlorophenyl)-5,6-dihydro-4-hydroxy-3-[(phenylmethyl)thio]-2H-pyran-2-one;

6-(3-Chlorophenyl)-5,6-dihydro-4-hydroxy-3-[(phenylmethyl)thio]-2H-pyran-2-one;

5,6-Dihydro-3-[(2-phenylethyl)thio]-6-[4-(phenylmethoxy)phenyl]-2H-pyran-2-one;

5,6-Dihydro-6-(4-methoxyphenyl)-3-[(2-phenylethyl)thio]-2H-pyran-2-one;

5,6-Dihydro-6-(4-methylthiophenyl)-3-[(2-phenylethyl)thio]-2H-pyran-2-one;

5,6-Dihydro-6-(4-methylphenyl)-3-[(2-phenylethyl)thio]-2H-pyran-2-one;

6-[1,1'-Biphenyl]-4-yl-5,6-dihydro-3-[(2-phenylethyl)thio]-2H-pyran-2-one;

5,6-Dihydro-6-[4-(1,1-dimethylethyl)phenyl]-3-[(2-phenylethyl)thio]-2H-pyran-2-one;

6-(3-Chlorophenyl)-5,6-dihydro-3-[(2-phenylethyl)thio]-2H-pyran-2-one;

6-[([1,1'-Biphenyl]-4-yloxy)methyl]-5,6-dihydro-3-[(2-phenylethyl)thio]-2H-pyran-2-one;

6-[1,1'-Biphenyl]-4-yl-6-butyl-5,6-dihydro-4-hydroxy-3-[(2-phenylethyl)thio]-2H-pyran-2-one;

4-[2,3-Dihydro-4-hydroxy-6-oxo-5-[(phenylmethyl)thio]-2H-pyran-2-yl]benzonitrile;

6-(4-Trifluoromethylphenyl)-5,6-dihydro-4-hydroxy-3-[(phenylmethyl)thio]-2H-pyran-2-one;

6-(3,5-Dichlorophenyl)-5,6-dihydro-4-hydroxy-3-[(phenylmethyl)thio]-2H-pyran-2-one;

6-(Pentafluorophenyl)-5,6-dihydro-4-hydroxy-3-[(phenylmethyl)thio]-2H-pyran-2-one;

5,6-Dihydro-4-hydroxy-6-(3-methylphenyl)-3-[(2-phenylethyl)thio]-2H-pyran-2-one;

6-(2-Chlorophenyl)-5,6-dihydro-4-hydroxy-3-[(phenylmethyl)thio]-2H-pyran-2-one;

6-Butyl-5,6-dihydro-4-hydroxy-6-phenyl-3-[(phenylmethyl)thio]-2H-pyran-2-one;

6-[1,1'-Biphenyl]-4-yl-6-butyl-5,6-dihydro-4-hydroxy-3-[(phenylmethyl)thio]-2H-pyran-2-one;

5,6-Dihydro-4-hydroxy-6-phenyl-3-[(phenylmethyl)thio]-6-propyl-2H-pyran-2-one;

5,6-Dihydro-4-hydroxy-6-phenyl-3-[(2-phenylethyl)thio]-6-propyl-2H-pyran-2-one;

5,6-Dihydro-4-hydroxy-6-pentyl-6-phenyl-3-[(phenylmethyl)thio]-2H-pyran-2-one;

5,6-Dihydro-4-hydroxy-6-pentyl-6-phenyl-3-[(2-phenylethyl)thio]-2H-pyran-2-one;

5,6-Dihydro-4-hydroxy-6-(3-methylbutyl)-6-phenyl-3-[(phenylmethyl)thio]-2H-pyran-2-one;

5,6-Dihydro-4-hydroxy-6-(3-methylbutyl)-6-phenyl-3-[(2-phenylethyl)thio]-2H-pyran-2-one;

5,6-Dihydro-4-hydroxy-6,6-diphenyl-3-[(phenylmethyl)thio]-2H-pyran-2-one;

5,6-Dihydro-4-hydroxy-6,6-diphenyl-3-[(2-phenylethyl)thio]-2H-pyran-2-one;

5,6-Dihydro-4-hydroxy-6-phenyl-6-(2-phenylethyl)-3-[(phenylmethyl)thio]-2H-pyran-2-one;

5,6-Dihydro-4-hydroxy-6-phenyl-6-(2-phenylethyl)-3-[(2-phenylethyl)thio]-2H-pyran-2-one;

5,6-Dihydro-4-hydroxy-6-[4-[2-(4-morpholinyl)ethoxy]phenyl]-6-(2-phenylethyl)-3-[(2-phenylethyl) thio]-2H-pyran-2-one;

1-[4-[3,6-Dihydro-4-hydroxy-6-oxo-5-[(2-phenylethyl)thio]-2H-pyran-2-yl]phenyl]-5-phenyl-1H-pyrrole-2-propanoic acid;

5,6-Dihydro-4-hydroxy-6-(3-methylbutyl)-3-[[2-(1-methylethyl)phenyl]thio]-6-phenyl-2H-pyran-2-one;

5,6-Dihydro-4-hydroxy-6-phenyl-6-(2-phenylethyl)-3-[[3-(phenylmethoxy)phenyl]methyl]-2H-pyran-2-one;

5,6-Dihydro-4-hydroxy-3-[5-methyl-2-(1-methylethyl)phenoxy]-6-phenyl-6-(2-phenylethyl)-2H-pyran-2-one;

N-(1,1-Dimethylethyl)-1-[[3,6-dihydro-4-hydroxy-6-oxo-2-phenyl-5-[(2-phenylethyl)thio]-2H-pyran-2-yl]methyl]-cyclohexanecarboxamide;

6-Butyl-3-[(1-ethyl-1H-indol-3-yl)thio]-5,6-dihydro-4-hydroxy-6-phenyl-2H-pyran-2-one;

5,6-Dihydro-4-hydroxy-6-(4-hydroxyphenyl)-3-[(phenylmethyl)thio]-2H-pyran-2-one;

5,6-Dihydro-4-hydroxy-6-(4-hydroxyphenyl)-3-[(2-phenylethyl)thio]-2H-pyran-2-one;

[4-[5,6-Dihydro-4-hydroxy-2-oxo-3-[(phenylmethyl)thio]-2H-pyran-6-yl]phenoxy]acetic acid;

[4-[5,6-Dihydro-4-hydroxy-2-oxo-3-[(2-phenylethyl)thio]-2H-pyran-6-yl]phenoxy]acetic acid;

[4-[5,6-Dihydro-4-hydroxy-2-oxo-3-[(phenylmethyl)thio]-2H-pyran-6-yl]phenoxy]acetic acid ethyl ester;

[4-[5,6-Dihydro-4-hydroxy-2-oxo-3-[(2-phenylethyl)thio]-2H-pyran-6-yl]phenoxy]acetic acid ethyl ester 5,6-Dihydro-4-hydroxy-6-[4-(2-hydroxyethoxy)phenyl]-3-[(phenylmethyl)thio]-2H-pyran-2-one;

5,6-Dihydro-4-hydroxy-6-[4-(2-hydroxyethoxy)phenyl]-3-[(2-phenylethyl)thio]-2H-pyran-2-one;

5,6-Dihydro-4-hydroxy-3-[(phenylmethyl)thio]-6-[4-[2-(4-thiomorpholinyl)ethoxy]phenyl]-2H-pyran-2-one-S,S-dioxide;

5,6-Dihydro-4-hydroxy-3-[(2-phenylethyl)thio]-6-[4-[2-(4-thiomorpholinyl)ethoxy]phenyl]-2H-pyran-2-one-S,S-dioxide;

4-[5,6-Dihydro-4-hydroxy-2-oxo-3-[(phenylmethyl)thio]-2H-pyran-6-yl]benzoic acid;

4-[5,6-Dihydro-4-hydroxy-2-oxo-3-[(2-phenylmethyl)thio]-2H-pyran-6-yl]benzoic acid;

5,6-Dihydro-4-hydroxy-6-[4-(hydroxymethyl)phenyl]-3-[(phenylmethyl)thio]-2H-pyran-2-one;

5,6-Dihydro-4-hydroxy-6-[4-(hydroxymethyl)phenyl]-3-[(2-phenylethyl)thio]-2H-pyran-2-one;

5,6-Dihydro-4-hydroxy-6-(3-methylbutyl)-3-[5-methyl-1-(phenylmethyl)hexyl]-6-phenyl-2H-pyran-2-one;

3-[1-(Cyclohexylthio)-5-methylhexyl]-5,6-dihydro-4-hydroxy-6-(3-methylbutyl)-6-phenyl-2H-pyran-2-one;

3-[2-Cyclohexyl-1-[(3-methylbutyl)amino]ethyl]-5,6-dihydro-4-hydroxy-6-(3-methylbutyl)-6-phenyl-2H-pyran-2-one;

5,6-Dihydro-4-hydroxy-6-(3-methylbutyl)-3-[(4-methylpentyl) (phenylmethyl) amino]-6-phenyl-2H-pyran-2-one;

5,6-Dihydro-4-hydroxy-6-phenyl-3-[(phenylmethyl)thio]-6-[(tetrahydro-3-furanyl)methyl]-2H-pyran-2-one;

2,3-Dihydro-4-hydroxy-6-oxo-2-phenyl-5-[(phenylmethyl)thio]-2H-pyran-3-acetamide;

2,3-Dihydro-4-hydroxy-6-oxo-2-phenyl-5-[(phenylmethyl)thio]-2H-pyran-3-butanamide;

5-(4-Hydroxybutyl)-5,6-dihydro-4-hydroxy-6-phenyl-3-[(phenylmethyl)thio]-2H-pyran-2-one;

5,6-Dihydro-4-hydroxy-6-phenyl-3-[(2-phenylethyl)thio]-2(1H)-pyridinone;

5,6-Dihydro-4-hydroxy-1-methyl-6-phenyl-3-[(2-phenylethyl)thio]-2(1H)-pyridinone;

Phenylmethyl 2-(1-methylethyl)-2-[[3,6-dihydro-4-hydroxy-6-oxo-2-phenyl-5-[(2-phenylethyl)thio]-2H-pyran-2-yl]methyl]hydrazinecarboxylate;

N-[1-[[3,6-Dihydro-4-hydroxy-6-oxo-2-phenyl-5-[(2-phenylethyl)thio]-2H-pyran-2-yl]methyl]cyclopentyl] urea;

N-[1-[[3,6-Dihydro-4-hydroxy-6-oxo-2-phenyl-5-[(2-phenylethyl)thio]-2H-pyran-2-yl]methyl]cyclopentyl]-N'-(phenylmethyl)urea;

Phenylmethyl [1-[[3,6-dihydro-4-hydroxy-6-oxo-2-phenyl-5-[(2-phenylethyl)thio]-2H-pyran-2-yl]methyl]cyclopentyl]carbamate;

6-[(2,3-Dimethyl-1H-pyrrol-1-yl)methyl]-5,6-dihydro-4-hydroxy-6-phenyl-3-[(2-phenylethyl)thio]-2H-pyran-2-one;

5,6-Dihydro-4-hydroxy-6-[2-(1-piperazinyl)ethyl]-6-phenyl-3-[(2-phenylethyl)thio]2H-pyran-2-one;

5,6-Dihydro-4-hydroxy-6-[2-(4-morpholinyl)ethyl]-6-phenyl-3-[(phenylmethyl)thio]-2H-pyran-2-one;

5,6-Dihydro-4-hydroxy-6-[3-(4-morpholinyl)propyl]-6-phenyl-3-[(phenylmethyl)thio]-2H-pyran-2-one;

5,6-Dihydro-4-hydroxy-6-[4-(4-morpholinyl)butyl]-6-phenyl-3-[(phenylmethyl)thio]-2H-pyran-2-one;

5,6-Dihydro-4-hydroxy-6-[2-(4-thiomorpholinyl)ethyl]-6-phenyl-3-[(phenylmethyl)thio]-2H-pyran-2-one;

5,6-Dihydro-4-hydroxy-6-[3-(4-thiomorpholinyl)propyl)-6-phenyl-3-[(phenylmethyl)thio]-2H-pyran-2-one;

5,6-Dihydro-4-hydroxy-6-[4-(4-thiomorpholinyl)butyl]-6-phenyl-3-[(phenylmethyl)thio]-2H-pyran-2-one;

5,6-Dihydro-4-hydroxy-6-[2-(1-piperazinyl)ethyl]-6-phenyl-3-[(phenylmethyl)thio]-2H-pyran-2-one;

5,6-Dihydro-4-hydroxy-6-[3-(1-piperazinyl)propyl]-6-phenyl-3-[(phenylmethyl)thio]-2H-pyran-2-one;

5,6-Dihydro-4-hydroxy-6-[4-(1-piperazinyl)butyl]-6-phenyl-3-[(phenylmethyl)thio]-2H-pyran-2-one;

5,6-Dihydro-4-hydroxy-6-[2-(4-methyl-1-piperazinyl)ethyl]-6-phenyl-3-[(phenylmethyl)thio]-2H-pyran-2-one;

5,6-Dihydro-4-hydroxy-6-[3-(4-methyl-1-piperazinyl)propyl]-6-phenyl-3-[(phenylmethyl)thio]-2H-pyran-2-one;

5,6-Dihydro-4-hydroxy-6-[4-(4-methyl-1-piperazinyl)butyl]-6-phenyl-3-[(phenylmethyl)thio]-2H-pyran-2-one;

5,6-Dihydro-4-hydroxy-6-[2-(4-morpholinyl)ethyl]-6-phenyl-3-[(2-isopropylphenyl)thio]-2H-pyran-2-one;

5,6-Dihydro-4-hydroxy-6-[3-(4-morpholinyl)propyl]-6-phenyl-3-[(2-isopropylphenyl)thio]-2H-pyran-2-one;

5,6-Dihydro-4-hydroxy-6-[4-(4-morpholinyl)butyl]-6-phenyl-3-[(2-isopropylphenyl)thio]-2H-pyran-2-one;

5,6-Dihydro-4-hydroxy-6-[2-(4-thiomorpholinyl)ethyl]-6-phenyl-3-[(2-isopropylphenyl)thio]-2H-pyran-2-one;

5,6-Dihydro-4-hydroxy-6-[3-(4-thiomorpholinyl)propyl]-6-phenyl-3-[(2-isopropylphenyl)thio]-2H-pyran-2-one;

5,6-Dihydro-4-hydroxy-6-[4-(4-thiomorpholinyl)butyl]-6-phenyl-3-[(2-isopropylphenyl)thio]-2H-pyran-2-one;

5,6-Dihydro-4-hydroxy-6-[2-(1-piperazinyl)ethyl]-6-phenyl-3-[(2-isopropylphenyl)thio]-2H-pyran-2-one;

5,6-Dihydro-4-hydroxy-6-[3-(1-piperazinyl)propyl]-6-phenyl-3-[(2-isopropylphenyl)thio]-2H-pyran-2-one;

5,6-Dihydro-4-hydroxy-6-[4-(1-piperazinyl)butyl]-6-phenyl-3-[(2-isopropylphenyl)thio]-2H-pyran-2-one;

5,6-Dihydro-4-hydroxy-6-[2-(4-methyl-1-piperazinyl)ethyl]-6-phenyl-3-[(2-isopropylphenyl)thio]-2H-pyran-2-one;

5,6-Dihydro-4-hydroxy-6-[3-(4-methyl-1-piperazinyl)propyl]-6-phenyl-3-[(2-isopropylphenyl)thio]-2H-pyran-2-one;

5,6-Dihydro-4-hydroxy-6-[4-(4-methyl-1-piperazinyl)butyl]-6-phenyl-3-[(2-isopropylphenyl)thio]-2H-pyran-2-one;

5,6-Dihydro-4-hydroxy3-[(2-isopropylphenyl)thio].-6-(3-morpholin-4-yl-3-oxopropyl)-6-phenyl-2H-pyran.-2-one;

5,6-Dihydro-4-hydroxy-3-[(2-isopropylphenyl)thio]-6-(4-morpholin-4-yl-4-oxobutyl)-6-phenyl-2H-pyran-2-one;

5,6-Dihydro-4-hydroxy-3-[(2-isopropylphenyl)thio]-6-(5-morpholin-4-yl-5-oxopentyl)-6-phenyl-2H-pyran-2-one;

5,6-Dihydro-4-hydroxy-3-[(2-isopropylphenyl)thio]-6-(3-thiomorpholin-4-yl-3-oxopropyl)-6-phenyl-2H-pyran-2-one;

5,6-Dihydro-4-hydroxy-3-[(2-isopropylphenyl)thio]-6-(4-thiomorpholin-4-yl-4-oxobutyl)-6-phenyl-2H-pyran-2-one;

5,6-Dihydro-4-hydroxy-3-[(2-isopropylphenyl)thio]-6-(5-thiomorpholin-4-yl-5-oxopentyl)-6-phenyl-2H-pyran-2-one;

5,6-Dihydro-4-hydroxy-3-[(2-isopropylphenyl)thio]-6-(3-piperazin-1-yl-3-oxopropyl)-6-phenyl-2H-pyran-2-one;

5,6-Dihydro-4-hydroxy-3-[(2-isopropylphenyl)thio]-6-(4-piperazin-1-yl-4-oxobutyl)-6-phenyl-2H-pyran-2-one;

5,6-Dihydro-4-hydroxy-3-[(2-isopropylphenyl)thio]-6-(5-piperazin-1-yl-5-oxopentyl)-6-phenyl-2H-pyran-2-one;

5,6-Dihydro-4-hydroxy-3-[(2-isopropylphenyl)thio]-6-[3-(4-methylpiperazin-1-yl)-3-oxopropyl]-6-phenyl-2H-pyran-2-one;

5,6-Dihydro-4-hydroxy-3-[(2-isopropylphenyl)thio]-6-[4-(4-methylpiperazin-1-yl)-4-oxobutyl]-6-phenyl-2H-pyran-2-one;

5,6-Dihydro-4-hydroxy-3-[(2-isopropylphenyl)thio]-6-[5-(4-methylpiperazin-1-yl)-5-oxopentyl]-6-phenyl-2H-pyran-2-one;

5,6-Dihydro-4-hydroxy-3-[(phenylmethyl)thio]-6-(3-morpholin-4-yl-3-oxopropyl)-6-phenyl-2H-pyran-2-one;

5,6-Dihydro-4-hydroxy-3-[(phenylmethyl)thio]-6-(4-morpholin-4-yl-4-oxobutyl)-6-phenyl-2H-pyran-2-one;

5,6-Dihydro-4-hydroxy-3-[(phenylmethyl)thio]-6-(5-morpholin-4-yl-5-oxopentyl)-6-phenyl-2H-pyran-2-one;

5,6-Dihydro-4-hydroxy-3-[(phenylmethyl)thio]-6-(3-thiomorpholin-4-yl-3-oxopropyl)-6-phenyl-2H-pyran-2-one;

5,6-Dihydro-4-hydroxy-3-[(phenylmethyl)thio]-6-(4-thiomorpholin-4-yl-4-oxobutyl)-6-phenyl-2H-pyran-2-one;

5,6-Dihydro-4-hydroxy-3-[(phenylmethyl)thio]-6-(5-thiomorpholin-4-yl-5-oxopentyl)-6-phenyl-2H-pyran-2-one;

5,6-Dihydro-4-hydroxy-3-[(phenylmethyl)thio]-6-(3-piperazin-1-yl-3-oxopropyl)-6-phenyl-2H-pyran-2-one;

5,6-Dihydro-4-hydroxy-3-[(phenylmethyl)thio]-6-(4-piperazin-1-yl-4-oxobutyl)-6-phenyl-2H-pyran-2-one;

5,6-Dihydro-4-hydroxy-3-[(phenylmethyl)thio]-6-(5-piperazin-1-yl-5-oxopentyl)-6-phenyl-2H-pyran-2-one;

5,6-Dihydro-4-hydroxy-3-[(phenylmethyl)thio]-6-[3-(4-methypiperazin-1-yl)-3-oxopropyl]-6-phenyl-2H-pyran-2-one;

5,6-Dihydro-4-hydroxy-3-[(phenylmethyl)thio]-6-[4-(4-methylpiperazin-1-yl)-4-oxobutyl]-6-phenyl-2H-pyran-2-one;

5,6-Dihydro-4-hydroxy-3-[(phenylmethyl)thio]-6-[5-(4-methylpiperazin-1-yl)-5-oxopentyl]-6-phenyl-2H-pyran-2-one;

Methyl 2-t-butyl-3-[[5,6-dihydro-4-hydroxy-2-oxo-6-phenyl-6-(2-phenylethyl)-2H-pyran-3-yl]thio]benzoate;

5-[3,6-Dihydro-4-hydroxy-5-[[5-methyl-3-(3-pyridinylmethoxy)-2-isopropylphenyl]thio]-6-oxo-2-phenyl-2H-pyran-2-yl]pentanoic acid;

3-[[5-Ethyl-2-(1-methyl-2-hydroxyethyl)phenyl]thio]-5,6-dihydro-4-hydroxy-6,6-diphenyl-2H-pyran-2-one;

5-[5-[(2-cyclopentyl-5-isopropylphenyl)thio]-3,6-dihydro-4-hydroxy-6-oxo-2-phenyl-2H-pyran-2-yl]pentanoic acid;

5,6-Dihydro-4-hydroxy-6-(3-methylbutyl)-6-phenyl-3-[[2-[2-(3-pyridinyl)ethyl]phenyl]thio]-2H-pyran-2-one;
5,6-Dihydro-4-hydroxy-3-[[5-(2-hydroxyethyl)-3-(2-phenylethyl)-2-isopropylphenyl]thio]-6-phenyl-6-(2-phenylethyl)-2H-pyran-2-one;
4-[[5,6-Dihydro-4-hydroxy-2-oxo-6,6-diphenyl-2H-pyran-3-yl]thio]-2-hydroxyindane;
3-[[4,5-Diethyl-2-(1-hydroxyethyl)phenyl]thio]-5,6-dihydro-4-hydroxy-6-phenyl-6-(2-phenylethyl)-2H-pyran-2-one;
5,6-Dihydro-4-hydroxy-3-[(2-isopropyl-5-methylphenyl)methyl]-6-(2-phenylethyl)-6-phenyl-2H-pyran-2-one;
5,6-Dihydro-4-hydroxy-3-[(3-hydroxymethyl-2-isopropyl-5-methylphenyl)methyl]-6,6-diphenyl-2H-pyran-2-one;
5,6-Dihydro-4-hydroxy-3-[[4-(hydroxymethyl)phenyl]methyl]-6-pentyl-6-phenyl-2H-pyran-2-one;
5,6-Dihydro-4-hydroxy-3-[(3-hydroxyphenyl)methyl]-6-(2-phenylethyl)-6-phenyl-2H-pyran-2-one;
5,6-Dihydro-4-hydroxy-6-pentyl-6-phenyl-3-[[4-(pyridin-3-ylmethoxy)phenyl]methyl]-2H-pyran-2-one;
5,6-Dihydro-4-hydroxy-3-[[2-isopropyl-3-[2-(morpholin-4-yl)ethoxy]phenyl]methyl]-6-(2-phenylethyl)-6-phenyl-2H-pyran-2-one;
5,6-Dihydro-4-hydroxy-3-(3-methyl-1-phenyl-but-2-enyl)-6,6-diphenyl-2H-pyran-2-one;
3-[(1,4-Di-tert-butyl-1H-imidazol-2-yl)thio]-5,6-dihydro-4-hydroxy-6-(2-phenylethyl)-6-phenyl-2H-pyran-2-one;
5,6-Dihydro-4-hydroxy-6-(3-methylbutyl)-3-(3-methyl-1-propyl-but-2-enyl)-6-phenyl-2H-pyran-2-one;
5,6-Dihydro-4-hydroxy-3-[[2-(hydroxymethyl)phenyl]methyl]-6-(2-phenylethyl)-6-phenyl-2H-pyran-2-one;
3-Diisobutylamino-5,6-dihydro-4-hydroxy-6,6-diphenyl-2H-pyran-2-one;
5,6-Dihydro-4-hydroxy-6-(2-phenylethyl)-6-phenyl-3-(N-phenyl-N-propylamino)-2H-pyran-2-one;
3-(3,4-Dihydro-2H-quinolin-1-yl)-6-hexyl-5,6-dihydro-4-hydroxy-6-phenyl-2H-pyran-2-one;
5,6-Dihydro-4-hydroxy-3-[(2-isopropyl-5-methylphenyl)amino]-6,6-diphenyl-2H-pyran-2-one;
6-Butyl-3-[(1,4-di-tert-butyl-1H-imidazol-2-yl)amino]-5,6-dihydro-4-hydroxy-6-phenyl-2H-pyran-2-one;
6-Butyl-3-(3,5-dimethylphenyl)-5,6-dihydro-4-hydroxy-6-phenyl-2H-pyran-2-one;
3-[4-[(Phenylmethoxy)methyl]-1-tert-butyl-1H-imidazol-2-yl]-5,6-dihydro-4-hydroxy-6-(2-phenylethyl)-6-phenyl-2H-pyran-2-one;
3-(1-tert-Butyl-4-methyl-1H-pyrrol-2-yl)-5,6-dihydro-4-hydroxy-6,6-diphenyl-2H-pyran-2-one;
6-[2-[4-(5,5-Dimethyl-4,5-dihydro-oxazol-2-yl)phenyl]ethyl]-5,6-dihydro-4-hydroxy-3-[(2-isopropyl-5-methylphenyl) thio]-6-phenyl-2H-pyran-2-one;
6-[2-[4-(4,4-Dimethyl-4,5-dihydro-oxazol-2-yl)phenyl]ethyl]-5,6-dihydro-4-hydroxy-3-[(2-isopropyl-5-methylphenyl) thio]-6-phenyl-2H-pyran-2-one;
6-[2-[4-(1,1-Dioxothiomorpholin-4-yl)phenyl]ethyl]-5,6-dihydro-4-hydroxy-3-[(2-isopropyl-5-methylphenyl)thio]-6-phenyl-2H-pyran-2-one;
1-Hydroxy-4-[2-[4-hydroxy-5-[(2-isopropyl-5-methylphenyl)thio]-6-oxo-2-phenyl-3,6-dihydro-2H-pyran-2-yl]ethyl]-1H-pyridin-2-one;
5,6-Dihydro-4-hydroxy-6-[2-(1H-indol-5-yl)ethyl]-3-[(2-isopropyl-5-methylphenyl)thio]-6-phenyl-2H-pyran-2-one;
5,6-Dihydro-4-hydroxy-6-(2-phenylethyl)-6-phenyl-3-(2-phenyl-[1,3]dithiolan-2-yl)-2H-pyran-2-one;
5,6-Dihydro-4-hydroxy-3-[(2-isopropyl-5-methylphenyl)thio]-6-(2-phenylethyl)-6-[4-[(pyridin-3-yl)methoxy]phenyl]-2H-pyran-2-one;
5,6-Dihydro-4-hydroxy-3-[(2-isopropylphenyl)thio]-6-phenyl-6-[5-(phenylmethyl)amino-2,2-dimethyl-pentyl]-2H-pyran-2-one;
5-[4-Hydroxy-5-[(2-isopropylphenyl)thio]-6-oxo-2-phenyl-3,6-dihydro-2H-pyran-2-yl]-4,4-dimethyl-pentanoic acid benzylamide;
1-[2-[4-Hydroxy-5-[(2-isopropylphenyl)thio]-6-oxo-2-phenyl-3,6-dihydro-2H-pyran-2-yl]-1-phenylethyl]-3-pyridin-2-ylmethylurea;
5,6-Dihydro-4-hydroxy-6-(5-hydroxypentyl)-3-[(2-isopropylphenyl)thio]-6-phenyl-2H-pyran-2-one;
5-[4-Hydroxy-5-[(2-isopropyl-5-methylphenyl)thio]-6-oxo-2-phenyl-3,6-dihydro-2H-pyran-2-yl]pentanoic acid, tert-butyl ester;
6-[4-(4,4-Dimethyl-4,5-dihydro-oxazol-2-yl)butyl]-5,6-dihydro-4-hydroxy-3-[(2-isopropylphenyl)thio]-6-phenyl-2H-pyran-2-one;
1-[[3,5-Dihydro-4-hydroxy-5-[(2-isopropylphenyl)thio]-6-oxo-2-phenyl-2H-pyran-2-yl]methyl]cyclohexyl]methyl carbamic acid phenylmethyl ester;
5,6-Dihydro-4-hydroxy-6-phenyl-3-[(phenylmethyl)thio]-6-[2-(4-pyridyl)ethyl]-2H-pyran-2-one;
5,6-Dihydro-4-hydroxy-6-[2-(5-hydroxy-2-methylphenyl)ethyl]-6-phenyl-3-[(phenylmethyl)thio]-2H-pyran-2-one;
5,6-Dihydro-4-hydroxy-6-[2-(3-(morpholin-4-yl)phenyl)ethyl]-6-phenyl-3-[(phenylmethyl)thio]-2H-pyran-2-one;
5,6-Dihydro-4-hydroxy-6-[2-phenylethyl]-3-[(phenylmethyl)thio]-6-(4-pyridyl)-2H-pyran-2-one;
5,6-Dihydro-4-hydroxy-6-phenyl-3-[(phenylmethyl)thio]-6-[2-(2-thienyl)ethyl]-2H-pyran-2-one;
6-[2-(2-Furyl) ethyl]-5,6-dihydro-4-hydroxy-6-phenyl-3-[(phenylmethyl)thio]-2H-pyran-2-one;
5,6-Dihydro-4-hydroxy-6-phenyl-3-[(phenylmethyl)thio]-6-[2-(1H-pyrrol-2-yl)ethyl]-2H-pyran-2-one;
5-[4-Hydroxy-5-[(2-isopropylphenyl)thio]-6-oxo-2-phenyl-3,6-dihydro-2H-pyran-2-yl]pentanoic acid methyl ester;
5-[4-Hydroxy-5-[(2-isopropylphenyl)thio]-6-oxo-2-phenyl-3,6-dihydro-2H-pyran-2-yl]pentanoic acid ethyl ester;
5-[4-Hydroxy-5-[(2-isopropylphenyl)thio]-6-oxo-2-phenyl-3,6-dihydro-2H-pyran-2-yl]pentanoic acid propyl ester;
5-[4-Hydroxy-5-[(2-isopropylphenyl)thio]-6-oxo-2-phenyl-3,6-dihydro-2H-pyran-2-yl]pentanoic acid isopropyl ester;
5-[4-Hydroxy-5-[(2-isopropylphenyl)thio]-6-oxo-2-phenyl-3,6-dihydro-2H-pyran-2-yl]pentanoic acid tert-butyl ester;
5-[4-Hydroxy-5-[(2-isopropylphenyl)thio]-6-oxo-2-phenyl-3,6-dihydro-2H-pyran-2-yl]pentanoic acid benzyl ester;
[3-[4-Hydroxy-5-[(2-isopropylphenyl)thio]-6-oxo-2-phenyl-3,6-dihydro-2H-pyran-2-yl]propyl]-carbamic acid tert-butyl ester;
[3-[4-Hydroxy-5-[(2-isopropylphenyl)thio]-6-oxo-2-phenyl-3,6-dihydro-2H-pyran-2-yl]-propyl]-carbamic acid benzyl ester;
1-Benzyl-3-{3-[4-hydroxy-5-[(2-isopropylphenyl)thio]-6-oxo-2-phenyl-3,6-dihydro-2H-pyran-2-yl]-propyl}-urea;
4-[4-Hydroxy-5-[(2-isopropylphenyl)thio]-6-oxo-2-phenyl-3,6-dihydro-2H-pyran-2-yl]-butane-1-sulfonic acid benzylamide;
4-[4-Hydroxy-5-[(2-isopropylphenyl)thio]-6-oxo-2-phenyl-3,6-dihydro-2H-pyran-2-yl]-butane-1-sulfonic acid amide;
4-Hydroxy-3-[(2-isopropyl-5-methylphenyl)thio]-6-phenyl-5,6-dihydro-1H-pyridin-2-one;
4-Hydroxy-3-[(2-isopropyl-5-methylphenyl)thio]-6-phenyl-6-(2-phenylethyl)-5,6-dihydro-1H-pyridin-2-one;
3-Hydroxy-2-[(2-isopropyl-5-methylphenyl)thiol]-5-phenyl-5-(2-phenylethyl)-cyclohex-2-enone;

3-Hydroxy-2-[(2-isopropyl-5-methylphenyl)thio]-5-phenyl-cyclohex-2-enone;

4-Hydroxy-3-[(2-isopropyl-5-methylphenyl)sulfonyl]-6-phenyl-6-(2-phenylethyl)-5,6-dihydro-2H-pyran-2-one;

4-Hydroxy-3-(2-isopropylbenzoyl)-6-phenyl-6-(2-phenylethyl)-5,6-dihydro-2H-pyran-2-one;

4-Hydroxy-3-[methoxyimino(phenyl)methyl]-6-phenyl-6-(2-phenylethyl)-5,6-dihydro-2H-pyran-2-one;

4-Hydroxy-3-[methylimino(phenyl)methyl]-6-phenyl-6-(2-phenylethyl)-5,6-dihydro-2H-pyran-2-one;

2,3-Dihydro-4'-hydroxy-3,3-dimethyl-5'-[(2-isopropylphenyl) thio]-spiro[4H-1-benzopyran-4,2'-[2H]pyran]-6'(3'H)-one;

2,3-Dihydro-4'-hydroxy-2,2-dimethyl-5'-[(5-methyl-2-isopropylphenyl)thio]-spiro[1H-indene-1,2'-[2H]pyran]-6'(3'H)-one;

2,3-Dihydro-4'-hydroxy-5'-[(5-methyl-2-isopropylphenyl)thio]-spiro[1H-indene-1,2'-[2H]pyran]-6'(3'H)-one;

4''-Hydroxy-5''-[(5-methyl-2-isopropylphenyl)thio]-dispiro[cyclopropane-1,2'(3'H)-[1H]indene-1',2''-[2H]pyran]-6''(3''H)-one;

3,4-Dihydro-4'-hydroxy-5'-[(5-methyl-2-isopropylphenyl)thio]-spiro[naphthalene-1(2H),2'-[2H]pyran]-6'(3'H)-one;

3,4-Dihydro-4'-hydroxy-2,2-dimethyl-5'-[(5-methyl-2-isopropylphenyl)thio]-spiro[naphthalene-1,2'-[2H]pyran]-6'(3'H)-one;

3',4'-Dihydro-4''-hydroxy-5''-[(5-methyl-2-isopropylphenyl)thio]-dispiro[cyclopropane-1,2'(1'H)-naphthalene-1',2''[2H]pyran]-6''(3''H)-one;

4-Hydroxy-3-(2-isopropylphenoxy)-6-phenyl-6-(2-phenylethyl)-5,6-dihydro-2H-pyran-2-one;

4-Hydroxy-3-(2-isopropyl-5-methylphenoxy)-6-phenyl-6-(2-phenylethyl)-5,6-dihydro-2H-pyran-2-one;

3-(2-tert-Butylphenoxy)-4-hydroxy-6-phenyl-6-(2-phenylethyl)-5,6-dihydro-2H-pyran-2-one;

5-[5-(2-Cyclopentylphenoxy)-4-hydroxy-6-oxo-2-phenyl-3,6-dihydro-2H-pyran-2-yl]pentanoic acid;

4-Hydroxy-3-(2-isopropyl-5-methylphenoxy)-6-(2-phenylethyl)-6-propyl-5,6-dihydro-2H-pyran-2-one;

6-Cyclopentylmethyl-4-hydroxy-3-(2-isopropylphenoxy)-6-phenyl-5,6-dihydro-2H-pyran-2-one;

3-(Cyclopropylphenylamino)-4-hydroxy-6-phenyl-6-(2-phenylethyl)-5,6-dihydro-2H-pyran-2-one;

N-[3-[Cyclopropyl[4-hydroxy-2-oxo-6-phenyl-6-(2-phenylethyl)-5,6-dihydro-2H-pyran-3-yl]amino]phenyl]benzenesulfonamide;

[3-[Cyclopropyl[4-hydroxy-2-oxo-6-(2-phenylethyl)-6-propyl-5,6-dihydro-2H-pyran-3-yl]amino]phenyl]amide quinoline-8-sulfonic acid;

3-(Cyclopropylphenylamino)-4-hydroxy-6-(2-phenylethyl)-6-5 propyl-5,6-dihydro-2H-pyran-2-one;

4-Hydroxy-6-isobutyl-6-(2-phenylethyl)-3-(phenylpropylamino)-5,6-dihydro-2H-pyran-2-one;

N-[4-Hydroxy-2-oxo-6-phenyl-6-(2-phenylethyl)-5,6-dihydro-2H-pyran-3-yl]-N-phenyl-methanesulfonamide;

N-[6-(2-Benzo[1,3]dioxol-5-yl-ethyl)-4-hydroxy-2-oxo-6-phenyl-5,6-dihydro-2H-pyran-3-yl]-N-(3-methylbutyl)benzenesulfonamide;

3-[Cyclopentyl(cyclopentylmethyl)amino]-4-hydroxy-6-phenyl-6-(2-phenylethyl)-5,6-dihydro-2H-pyran-2-one;

4-Hydroxy-3-[methoxy(phenyl)methyl]-6-phenyl-6-(2-phenylethyl)-5,6-dihydro-2H-pyran-2-one;

3-[Cyclopentyl(cyclopentyloxy)methyl]-4-hydroxy-6-(2-phenylethyl)-6-propyl-5,6-dihydro-2H-pyran-2-one;

3-(1-Cyclopentyloxy-3-methylbutyl)-4-hydroxy-6-(3-methylbutyl)-6-phenyl-5,6-dihydro-2H-pyran-2-one;

6-Cyclopentyl-3-[cyclopentyl(isopropoxy)methyl]-4-hydroxy-6-(3-methylbutyl)-5,6-dihydro-2H-pyran-2-one;

4-Hydroxy-3-[(2-isopropylphenyl)thio]-6-(2-phenylethyl)-6-propyl-5,6-dihydro-2H-pyran-2-one;

4-Hydroxy-6-isobutyl-3-[(2-isopropyl-5-methylphenyl)thio]-6-(2-phenylethyl)-5,6-dihydro-2H-pyran-2-one;

3-[(2-tert-Butyl-furan-3-yl)thio]-4-hydroxy-6-phenyl-6-(2-phenylethyl)-5,6-dihydro-2H-pyran-2-one;

4-Hydroxy-3-[(3-isopropyl-pyridin-4-yl)thio]-6-phenyl-6-(2-phenylethyl)-5,6-dihydro-2H-pyran-2-one;

3-[(2-Cyclopentyl-pyridin-3-yl)thio]-4-hydroxy-6-pentyl-6-phenyl-5,6-dihydro-2H-pyran-2-one;

4-Hydroxy-6-isobutyl-3-[(3-isopropyl-isoxazol-4-yl)thio]-6-(2-phenylethyl)-5,6-dihydro-2H-pyran-2-one;

5-[(2-Isopropyl-5-methylphenyl)thio]-6-oxo-2-phenyl-2-(2-phenylethyl)-3,6-dihydro-2H-pyran-4-yl acetic acid ester;

2-[2-(Benzo[1,3]dioxol-5-yl)ethyl]-5-[(2-isopropyl-5-methylphenyl)thio]-6-oxo-2-phenyl-3,6-dihydro-2H-pyran-4-yl propionic acid ester;

5-[4-Isobutyryloxy-5-[(2-isopropylphenyl)thio]-6-oxo-2-phenyl-3,6-dihydro-2H-pyran-2-yl]-pentanoic acid;

N-[3-[Cyclopropyl[4-(acetyloxy)-5,6-dihydro-2-oxo-6-phenyl-(2-phenylethyl)-2H-pyran-3-yl]methyl]phenyl]-benzenesulfonamide;

Propanoic acid 5-[cyclopropyl[3-[(phenylsulfonyl)amino]phenyl]methyl]-3,6-dihydro-6-oxo-2,2-diphenyl-2H-pyran-4-yl ester;

2,2-Dimethylbutanoic acid 3,5-dihydro-6-oxo-2-(2-phenylethyl)-5-(1-phenylpropyl)-2-propyl-2H-pyran-4-yl ester and Benzenacetic acid 5-[cyclopropyl[3-[(ethylsulfonyl)amino]phenyl]methyl]-3,6-dihydro-6-oxo-2-(2-phenylethyl)-2-propyl-2H-pyran-4-yl ester.

4. DETAILED DESCRIPTION OF THE INVENTION

Here, the term "alkyl" means a straight or branched hydrocarbon radical having from 1 to 12 carbon atoms unless otherwise specified and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, undecyl, and dodecyl. The alkyl groups may contain one or more sites of unsaturation such as double or triple carbon-carbon bonds. The alkyl group is unsubstituted or substituted by from 1 to 3 substituents selected from alkyl, alkoxy, thioalkoxy all as defined herein, hydroxy, thiol, nitro, halogen, amino, formyl, carboxyl, nitrile, —NH—CO—R, —CO—NH—, —CO$_2$R, —COR, aryl, or heteroaryl wherein alkyl (R), aryl, and heteroaryl are defined as herein.

The term "cycloalkyl" means a hydrocarbon ring which contains from 3 to 12 carbon atoms unless otherwise specified, for example, cyclopropyl, cyclobutyl, cyclopentyl, cyclohexyl, and adamantyl. Where possible, the cycloalkyl group may contain double bonds. The cycloalkyl ring may be unsubstituted or substituted by from 1 to 3 substituents selected alkyl, alkoxy, thioalkoxy all as defined herein, hydroxy, thiol, nitro, halogen, amino, formyl, carboxyl, nitrile, —NH—CO—R, —CO—NHR—, —CO$_2$R, —COR, aryl, or heteroaryl wherein alkyl (R), aryl, and heteroaryl are defined as herein.

The term alkylcycloalkyl means a cycloalkyl group as defined above attached directly to an alkyl group as defined above.

The terms "alkoxyl" and "thioalkoxy" are O-alkyl or S-alkyl as defined above for alkyl.

The term spirocycle refers to a carbocyclic or heterocyclic ring whose ends meet at a single carbon in a chain or another ring.

The term "aryl" means an aromatic radical which is a phenyl group, a benzyl group, a naphthyl group, a biphenyl group, a pyrenyl group, an anthracenyl group, a fluarenyl group or a fused ring resulting from any two of phenyl, naphthyl, and a 5- or 6-membered ring containing from 0 to 3 heteroatoms selected from quinolones, isoquinolones, indoles, indanes, benzofurans, benzothiophenes, benzoxazoles, benzothiazoles, benzisoxazoles, coumarins, benzimidazoles and the like, unsubstituted or substituted by 1 to 3 substituents selected from alkyl as defined above, alkoxy as defined above, thioalkoxy as defined above, hydroxy, thiol, nitro, halogen, amino, formyl, carboxy, nitrile, —NHCOR, —CONHR, —$CO_2R$, —COR, aryl, or heteroaryl wherein alkyl (R), aryl, and heteroaryl are defined as above.

The terms "heteroaryl" and "heterocycle", represented by an "Ar", mean a heterocyclic radical which is 2- or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isaxazolyl, 3- or 5- 1,2,4-triazolyl, 4- or 5- 1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5 -, 6-, or 7-benzimidazolyl, 2-, 4-, 5-, 6-, or 7-benzothiazolyl, 1- or 2-piperazinyl, 2-, 3-, or 4-morpholinyl, 2-, 3-, or 4-thiomorpholinyl, 1-, 2-, or 3-pyrrolidinyl, 2- or 3-tetrahydrofuranyl, 2-, 3-, or 4-tetrahydropyranyl, 2- 3-, or 4-piperidinyl, 1-, 2-, 4-, 5-, or 6-tetrahydropyrimidinyl, 2-dioxolinyl, 2-, 4-, or 5-imidazolidinyl, 1-, 2-, 3-, 4-, 5-, 6-, or 7-indolinyl, unsubstituted or substituted by 1 to 2 substituents selected from alkyl as defined above, aryl as defined above, alkoxy as defined above, thioalkoxy as defined above, hydroxy, thiol, nitro, halogen, formyl, amino, carboxyl, nitrile, —NHCOR, —$CO_2R$, —COR, wherein alkyl in as defined above or phenyl.

"Halogen" is fluorine, chlorine, bromine or iodine.

Some of the compounds of Formula 1 are capable of further forming pharmaceutically acceptable acid-addition and/or base salts. All of these forms are within the scope of the present invention.

Pharmaceutically acceptable acid addition salts of the compounds of Formula 1 include salts derived from non-toxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinates suberate, sebacate, fumarate, maleate, mandelate, benzoate, chlorobenzoate, methylbenzoate, dinitrobenzoate, phthalate, benzensoulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al., "Pharmaceutical Salts," *Journal of Pharmaceutical Science,* 66: 1–19 (1977).

The acid addition salt of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge, S. M., et al., "Pharmaceutical Salts," *Journal of Pharmaceutical Science,* 66: 1–19 (1977).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula 1 or a corresponding pharmaceutically acceptable salt of a compound of Formula 1.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or, synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as antagonists of a retroviral protease, as agents for the treatment of infections caused by a retrovirus including HIV, or as agents for the treatment of diseases due to AIDS, the compounds utilized in the pharmaceutical method of this invention are administered at the initial dosage of about 0.01 mg to about 100 mg/kg daily. A daily dose range of about 0.01 mg to about 10 mg/kg is preferred. The dosages, however, may be varied depending upon the requirements of the patient, the severity of the condition being treated, the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

4.1 General Synthetic Approaches to 5,6-Dihydropyrone Derivatives

Scheme I, shown below, illustrates the preparation of substituted dihydropyrones III.

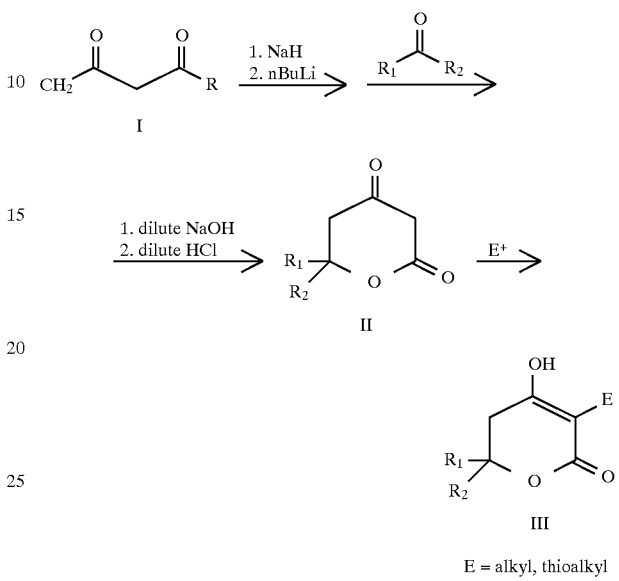

Methyl acetoacetate (I) is treated sequentially with a metal hydride, preferably sodium hydride, in THF or ether at −20° C. to +10° C., and with a stronger base, usually n-BuLi, in a solvent such as THF or ether at −20° C. to +10° C., producing the dianion. The reaction mixture is quenched with an appropriately substituted aldehyde or ketone, allowed to react for an additional 15 minutes to 24 hours, and finally worked up, furnishing the β-keto lactone (dihydropyrone) II. Compound II is elaborated into target pyrones III via treatment with a suitable electrophile, such as a thiotosylate, an alkyl halide or the like, in ethanol or DMF solution containing an inert base such as triethylamine and/or sodium bicarbonate at 25° C. to 80° C.

For purposes of the above and other syntheses of the compounds of the present invention, reactive functional groups present in starting materials, reaction intermediaters, or reaction products may be protected during chemical reactions using protecting groups which render the reactive functional groups substantially inert to the reaction conditions. (See for example, *Protective Groups in Organic Synthesis*, 2 ed., T. W. Green and P. G. Wuts, John Wiley & Sons, New York, N.Y. 1991). Thus, for example, protecting groups such as the following may be utilized to protect suitable amino, hydroxyl, and other groups of related reactivity: carboxylic acyl groups, such as formyl, acetyl, trifluoroacetyl; alkoxycarbonyl groups, such as ethoxycarbonyl, t-butoxycarbonyl (BOC), β,β,β-trichloroethoxycarbonyl (TCEC), β-iodoethoxycarbonyl; aryloxycarbonyl groups, such as benzyloxycarbonyl, p-methoxybenzyloxycarbonyl, phenoxycarbonyl; trialkyl silyl groups, such as trimethylsilyl and t-butyldimethylsilyl (TBDMS); and groups such as trityl, tetrahydropyranyl, vinyloxycarbonyl, o-nitrophenylsulfenyl, diphenylphosphinyl, p-toluenesulfonyl, and benzyl, may all be utilized. The protecting group may be removed, after completion of the synthetic reaction of interest, by procedures known to those skilled in the art. For example, the BOC group may be removed by acidolysis, the trityl group by hydrogenolysis, TBDMS by treatment with fluoride ions, and TCEC by treatment with zinc.

Scheme II describes an alternate synthesis of dihydropyrones which are substituted at C-3.

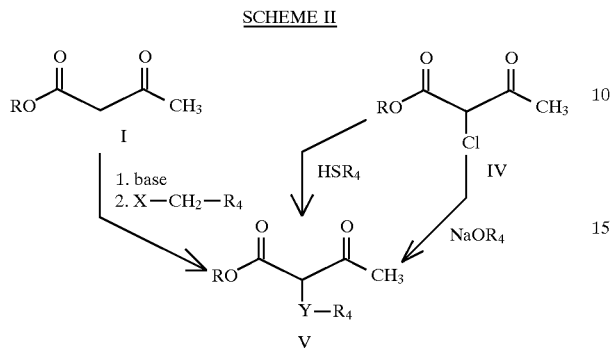

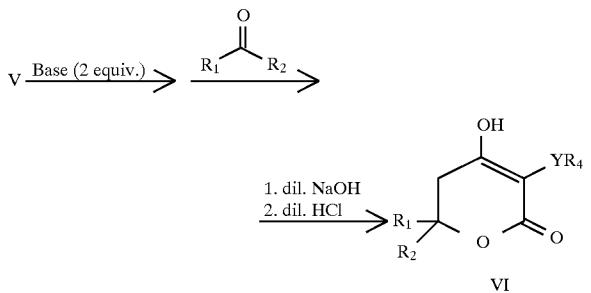

The acetoacetate I is treated with a base, such as sodium hydride or sodium ethoxide, in a suitable solvent such as THF, ether, or alcohol at −20° C. to 10° C., and the resulting anion is quenched with an appropriately substituted alkyl or benzyl halide, usually the bromide or iodide, to give ketoester V (Y=CH$_2$). Alternatively, chloroacetoacetate IV is reacted with a thiol, preferably in the presence of a suitable base such as triethylamine, piperidine, or pyridine, in a suitable solvent such as dichloromethane, at −10° C. to +25° C., affording ketoester V (Y=S) (see Z. Yoshida et al., Tetrahedron 26: 2987 (1970)). The requisite thiols can be prepared from the corresponding phenol via the Newman-Kwart rearrangement (see, for example, H. Kwart and H. Omura, J. Amer. Chem. Soc. 93: 7250 (1971); M. S. Newman and F. W. Hetzel, Org. Syn. Coll. Vol. VI: 824 (1988); M. S. Newman and H. A. Karnes, J. Org. Chem. 31: 3980 (1966)) or from the corresponding iodobenzene via a nucleophilic displacement with thiourea in the presence of a nickel catalyst (K. Takagi, Chem. Letters, 1307 (1985)). similarly, reaction of IV with an alkoxide in a suitable solvent such as benzene, DMF, or mixtures of THF and HMPA, at −10° C. to 25° C., yields acetoacetate V (Y=O) (see T. Sasaki et al., Tetrahedron 38: 85 (1982)). Intermediate V is subsequently elaborated into dihydropyrones VI using the general procedure outlined in Scheme I above.

Analogs possessing amino substituents at the 3-position can be prepared as shown in Scheme III.

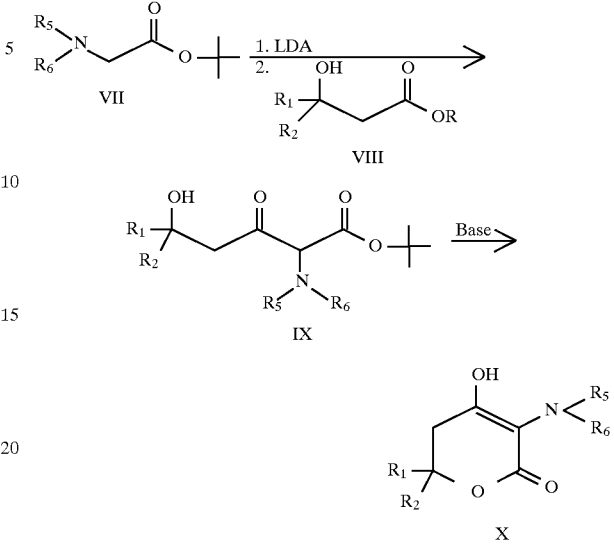

Ester VII is treated with a suitable base, such as lithium diisopropylamide, in a suitable solvent such as THF or ether, at −78° C. to 0° C., and the resulting anion is reacted with an appropriately substituted acylating agent such as ester VIII, producing ketoester IX. Cyclization of IX by e.g. treatment with a suitable base such as sodium hydroxide or sodium alkoxide yields desired dihydropyrones X.

Any of the 4-hydroxy-2H-pyran-2-ones such as III, VI, or X can be constructed to contain an appropriate leaving group (such as halogen, acetate, tosylate, etc.) in one of the $R_1$ or $R_2$ substituents. Such leaving groups can be displaced by primary or secondary amines to further embellish the $R_1$ or $R_2$ substituents. Such displacement would be carried out in alcohol or DMF or DMSO at −10° to 125° C. Likewise, if $R_1$ or $R_2$ contain a carboxylic acid related group, then further chemistry on that group would further embellish the $R_1$ or $R_2$ substituents. Such reactions would include esterification or amide formation using methods well known in the art.

Furthermore, 4-hydroxy-2(1H)-pyridinones such as XI, shown below, are known in the art (e.g. see M. J. Ashton et al., Heterocycles 28:(2) 1015 (1989)), and can be converted to desired protease inhibitors and antiviral agents analogous to the 5,6-dihydropyrones by using reactions similar to that used for conversion of II→III shown in Scheme I above.

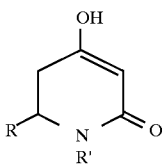

Substituted 1,3-cyclohexandiones can be prepared as described by Werbel (see J. Med. Chem. 35: 3429–47 (1992) and references cited therein). The 1,3-cyclohexandiones can be converted to substituted analogues using reactions similar to those used for conversions II→III.

Tetrahydro(thio)pyran-2,4-dione derivatives can be prepared as described in U.S. Pat. No. 4,842,638 and references cited therein. The tetrahydro(thio)pyran-2,4-diones can be converted to various substituted analogues using reactions similar to those used for conversions of II→III.

Derivatives containing a thio moiety at the 3-position can also be prepared as shown in Scheme IV:

SCHEME IV

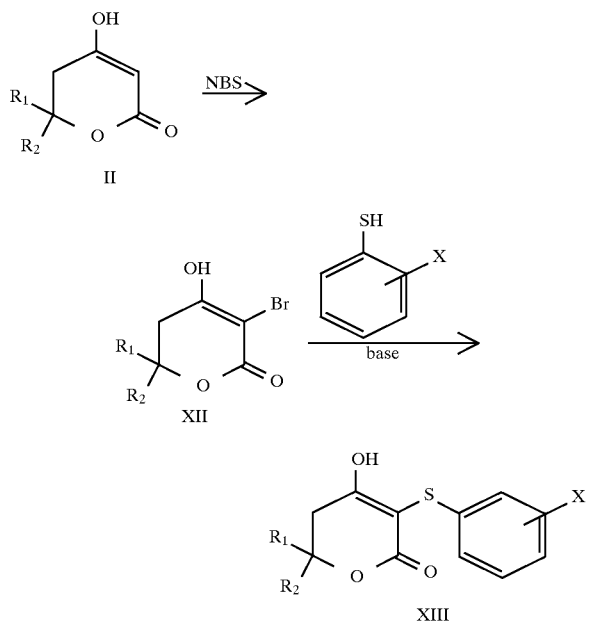

SCHEME V

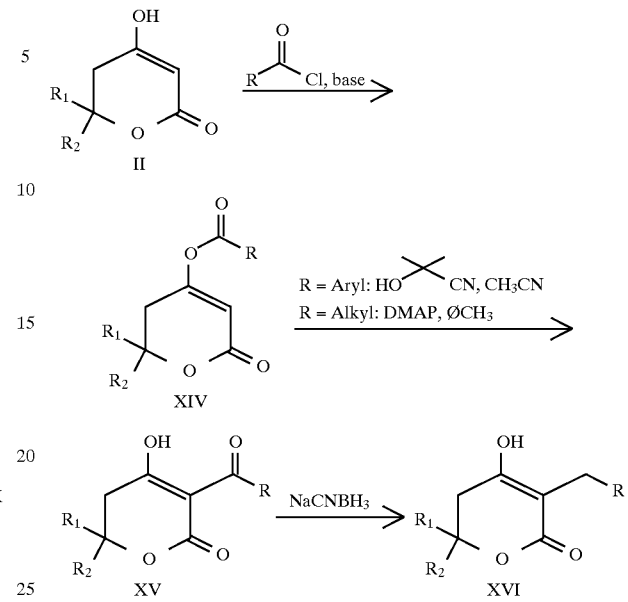

Dihydropyrone II is treated with a suitable brominating agent, such as N-bromosuccinimide, in a suitable solvent, such as t-butanol, for 1 to 18 hours. The resulting bromo intermediate XII is reacted with a thiol, usually in the presence of an appropriate base such as pyridine or piperidine, in a suitable solvent such as dichloromethane at 0° C. to +25° C. to afford desired product XIII.

An alternate synthesis of derivatives containing a carbon substituent at the 3-position is shown in Scheme V.

The dihydropyrone II is reacted with a suitable acid chloride, and the product is rearranged to give intermediate XV according to procedures outlined in U.S. Pat. No. 4,842,638 (1989). The keto group of XV is reduced to the methylene with an appropriate reducing agent, such as sodium cyanoborohydride or hydrogen in the presence of a catalyst, to afford compound XVI.

In Scheme VI, an optional method for preparing certain 4-hydroxy-2H-pryan-2-ones (such as III or VI) with complex amide containing side chains as $R_1$ or $R_2$ is shown.

SCHEME VI

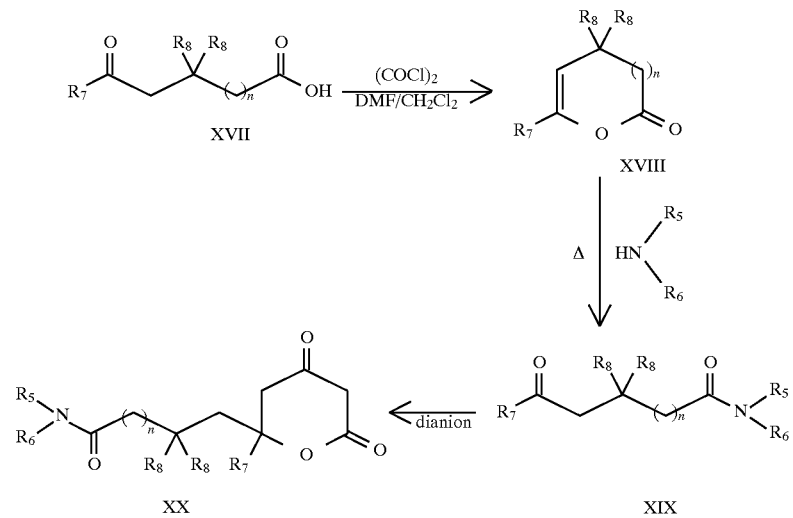

The prerequisite acid XVII prepared by literature conditions is cyclized to the lactone XVIII in DMF and dichloromethane at temperatures of 0° to 75° C. The lactone is ring opened by the appropriately substituted amine either neat or in solvents such as toluene, at 75°–110° C. to produce ketone amide XIX. This amide XIX is treated with the dianion as described in Scheme I to produce the lactone XX which is identical to II where $R_1$ is equal to the new amide containing chain. XX can be converted to the target compounds using conditions described in Scheme I.

The compounds of the present invention can exist in their tautomeric forms, i.e. the enol and keto forms shown in Scheme I. Both such forms as well as their mixtures are preferred aspects of the instant invention.

The substituted phenylpropiophenones were prepared by hydrogenation of the corresponding chalcones in tetrahydrofuran with 5% Pd on $BaSO_4$ as catalyst.

The chalcones were prepared according to Kohler and Chadwell Org. Synth. Coll. Vol. I, 78, 1941.

4.2 PROCEDURES FOR THE PREPARATION OF 5,6-DIHYDROPYRONE DERIVATIVES

GENERAL METHOD 1.

Methyl acetoacetate was added dropwise to a slurry of hexane washed sodium hydride in anhydrous tetrahydrofuran at 0° C. and the reaction stirred at 0° C. (15 minutes to 1 hour). n-Butyl lithium was then added at 0° C. and the reaction stirred at 0° C. (15 minutes to 1 hour). The aldehyde or ketone, in tetrahydrofuran, was added to the dianion and the reaction stirred at 0° C. (15 minutes to 24 hours) and allowed to warm to room temperature (15 minutes to 24 hours). To the reaction mixture was added water and the mixture allowed to stir 15 minutes to overnight. After extracting with diethyl ether, the aqueous layer at 0° C. was acidified with acid(2–6N HCl) to pH 1–2 and the aqueous layer extracted with ethyl acetate or $CH_2Cl_2$. The organic extracts of the acid solution were combined, dried over $MgSO_4$ and concentrated.

EXAMPLE A 5,6-Dihydro-4-hydroxy-6-phenyl-2H-pyran-2-one (±)

The title compound was prepared as described in General Method 1 using 13.67 g methyl acetoacetate, 8.5 g of NaH 60% dispersion in oil, 73.6 mL of 1.6M n-butyl lithium in hexane, 10 g of benzaldehyde, and 300 mL of tetrahydrofuran. After addition of the aldehyde, the reaction was stirred 15 minutes at −78° C. then allowed to warm to room temperature overnight. A solid was filtered off after concentration (m.p. 145°–146° C.). $^1$H NMR (CDCl$_3$) δ 2.8–3.05 (m, 2 H), 3.5 (d, 1 H), 3.7 (d, 1 H), 5.7 (dd, 1 H), 7.3–7.5 (m, 5 H).

EXAMPLE B 5,6-Dihydro-4-hydroxy-6-(2-methylpropyl)-6-phenyl-2H-pyran-2-one (±)

The title compound was prepared as described in General Method 1 using 12 g methyl acetoacetate, 4.3 g of NaH 60% dispersion in oil, 64.5 mL of 1.6M n-butyl lithium in hexane, 10 g of iso-valerophenone, and 300 mL of tetrahydrofuran. After addition of the phenone, the reaction was stirred 15 minutes at −78° C. and 2 hours at room temperature. The crude reaction was flash chromatographed using hexane/ethyl acetate 6/40–40/60 as eluent. The solid was triturated from diethyl ether (m.p. 123.5°–125° C.). $^1$H NMR (CDCl$_3$) δ 0.81 (d, 3 H), 0.89 (d, 3 H), 1.6–1.7 (M, 1 H), 1.91 (m, 2 H), 2.90 (d, 1 H), 2.95 (d, 1 H), 3.25 (d, 1 H), 3.35 (d, 1 H), 7.25–7.45 (m, 5 H).

EXAMPLE C 5,6-Dihydro-4-hydroxy-6-(4-methoxyphenyl)-2H-pyran-2-one, (±)

The title compound was prepared as described in General Method 1 using 5 mL of methyl acetoacetate, 2.0 g of NaH 60% dispersion in oil, 25 mL of 2.0M n-butyl lithium in hexane, 7.0 mL of 4-methoxybenzaldehyde and 150 mL of tetrahydrofuran. After addition of the aldehyde, the reaction was stirred for 15 minutes at 0° C. then allowed to warm to room temperature overnight. The crude product was triturated from diethyl ether to afford a solid (m.p.159°–162° C. (dec.)). $^1$H NMR (CDCl$_3$) δ 2.91 (dd, 2 H), 3.57 (dd, 2 H), 3.83 (s, 3 H), 5.66 (dd, 1 H), 6.93–6.97 (m, 2 H), 7.30–7.34 (m, 2 H).

EXAMPLE D 5,6-Dihydro-4-hydroxy-6-[4-(methylthio)phenyl]-2H-pyran-2-one, (±)

The title compound was prepared as described in General Method 1 using 10 mL of methyl acetoacetate, 4.0 g of NaH 60% dispersion in oil, 60 mL of 1.6M n-butyl lithium in hexane, 18.8 mL of 4-methylthiobenzaldehyde and 200 mL of tetrahydrofuran. After addition of the aldehyde, the reaction was stirred for 15 minutes at 0° C. then allowed to warm to room temperature overnight. The crude product was triturated from diethyl ether to afford a solid (m.p. 139°–141° C.). $^1$H NMR (CDCl$_3$) δ 2.51 (s, 3 H), 2.92 (dd, 2 H), 3.58 (dd, 2 H), 5.68 (dd, 1 H), 7.27–7.31 (m, 4 H).

EXAMPLE E 5,6-Dihydro-4-hydroxy-6-(4-methylphenyl) -2H-pyran-2-one, (±)

The title compound was prepared as described in General Method 1 using 10 mL of methyl acetoacetate, 3.7 g of NaH 60% dispersion in oil, 58 mL of 1.6M n-butyl lithium in hexane, 10.9 mL of p-tolualdehyde and 250 mL of tetrahydrofuran. After addition of the aldehyde, the reaction was stirred for 15 minutes at 0° C. then allowed to warm to room temperature overnight. The crude product was triturated from diethyl ether to afford a solid (m.p. 138°–139° C.). $^1$H NMR (CDCl$_3$) δ 2.39 (s, 3 H), 2.93 (dd, 2 H), 3.58 (dd, 2 H), 5.69 (dd, 1 H), 7.23–7.31 (m, 4 H).

EXAMPLE F

6-[4-(1,1-Dimethylethyl)phenyl]-5,6-dihydro-4-hydroxy-2H-pyran-2-one, (±)

The title compound was prepared as described in General Method 1 using 5.0 mL of methyl acetoacetate, 2.0 g of NaH 60% dispersion in oil, 31.5 mL of 1.6M n-butyl lithium in hexane, 9.0 g of 4-(1,1-dimethylethyl)benzaldehyde and 100 mL of tetrahydrofuran. After addition of the aldehyde, the reaction was stirred for 15 minutes at 0° C. then allowed to warm to room temperature overnight. The crude product was triturated from diethyl ether to afford a solid (m.p. 164°–165° C.). $^1$H NMR (CDCl$_3$) δ 1.33 (s, 9 H), 2.94 (dd, 2 H), 3.59 (dd, 2 H), 5.69 (dd, 1 H), 7.31–7.47 (m, 4 H).

EXAMPLE G 6-(4-Chlorophenyl)-5,6-dihydro-4-hydroxy-2H-pyran-2-one, (±)

The title compound was prepared as described in General Method 1 using 10 mL of methyl acetoacetate, 3.9 g of NaH 60% dispersion in oil, 58 mL of 1.6M n-butyl lithium in hexane, 13.5 g of 4-chlorobenzaldehyde and 250 mL of tetrahydrofuran. After addition of the aldehyde, the reaction was stirred for 15 minutes at 0°0 C. then allowed to warm to room temperature overnight. The crude product was triturated from diethyl ether to afford a solid (m.p. 149°–150° C.). $^1$H NMR (CDCl$_3$) δ 2.83 (dd, 1 H), 2.95 (dd, 1 H), 3.60 (dd, 2 H), 5.67 (dd, 1 H), 7.33–7.44 (m, 4 H).

EXAMPLE H 6-(3-Chlorophenyl)-5,6-dihydro-4-hydroxy-2H-pyran-2-one, (±)

The title compound was prepared as described in General Method 1 using 5.0 mL of methyl acetoacetate, 2.0 g of NaH 60% dispersion in oil, 25 mL of 2.0M n-butyl lithium in hexane, 6.5 mL of 3-chlorobenzaldehyde and 150 mL of tetrahydrofuran. After addition of the aldehyde, the reaction was stirred for 15 minutes at 0° C. then allowed to warm to room temperature overnight. The crude product was triturated from diethyl ether to afford a solid (m.p. 122°–124° C.). $^1$H NMR (CDCl$_3$) δ 2.83 (dd, 1 H), 2.96 (dd, 1 H), 3.60 (dd, 2 H), 5.68 .(dd, 1 H), 7.25–7.42 (m, 4 H).

EXAMPLE I 5,6-Dihydro-4-hydroxy-6-[4-(phenylmethoxy)phenyl]-2H-pyran-2-one, (±)

The title compound was prepared as described in General Method 1 using 5.0 mL of methyl acetoacetate, 2.0 g of NaH 60% dispersion in oil, 25 mL of 2.0M n-butyl lithium in hexane, 12.0 g of 4-benzyloxybenzaldehyde and 150 mL of tetrahydrofuran. After addition of the aldehyde, the reaction was stirred for 15 minutes at 0° C. then allowed to warm to room temperature overnight. The crude product was triturated from diethyl ether to afford a solid (m.p. 165°–166° C). $^1$H NMR (CDCl$_3$) δ 2.91 (dd, 2 H), 3.56 (dd, 2 H), 5.09 (s, 2 H), 5.65 (dd, 1 H), 6.98–7.04 (m, 2 H), 7.30–7.44 (m, 7 H).

EXAMPLE J

6-[1,1'-Biphenyl]-4-yl-5,6-dihydro-4-hydroxy-2H-pyran-2-one, (±)

The title compound was prepared as described in General Method 1 using 13.0 g of ethyl acetoacetate, 5.3 g of NaH 50% dispersion in oil, 60 mL of 1.6M n-butyl lithium in hexane, 16.3 g of 4-biphenylcarboxaldehyde and 300 mL of tetrahydrofuran. After addition of the aldehyde, the reaction was stirred for 15 minutes at 0° C. then allowed to warm to room temperature overnight. The crude product was triturated from diethyl ether to afford a solid (m.p. 150°–152° C.). $_1$H NMR (CDCl$_3$) δ 2.97 (dd, 2 H), 3.60 (dd, 2 H) 5.77 (dd, 1 H), 7.27–7.68 (m, 9 H).

EXAMPLE K

6-[[(1,1'-Biphenyl]-4-yloxy]methyl]-5,6-dihydro-4-hydroxy-2H-pyran-2-one, (±)

The title compound was prepared as described in General Method 1 using 4.76 g of methyl acetoacetate, 1.97 g of NaH 50% dispersion in oil, 19.5 mL of 2.1M n-butyl lithium in hexane, 8.7 g of [[1,1'-biphenyl]-4-yloxy]-acetaldehyde and 200 mL of tetrahydrofuran. After addition of the aldehyde, the reaction was stirred for 60 minutes at 0° C. then allowed to warm to room temperature overnight. The crude product was triturated from diethyl ether to afford a solid (m.p. 152°–154° C.). $^1$H NMR (CDCl$_3$) δ 2.83 (dd, 1 H), 2.95 (dd, 1 H) 3.61 (dd, 2 H), 4.23 (dd, 1 H), 4.38 (dd, 1 H), 5.03–5.07 (m, 1 H), 6.94–6.98 (m, 2 H), 7.30–7.57 (m, 7 H).

EXAMPLE L

6-[1,1'-Biphenyl]-4-yl-6-butyl-5,6-dihydro-4-hydroxy-2H-pyran-2-one (±)

The title compound was prepared as described in General Method 1 using 13 g ethyl acetoacetate, 5.3 g of NaH 60% dispersion in oil, 60 mL of 1.6M n-butyl lithium in hexane, 21 g of 1-[1,1'-biphenyl]-4-yl-1-pentanone and 300 mL of tetrahydrofuran. After addition of the ketone, the reaction was stirred 15 minutes at −78° C. and 2 hours at room temperature. The crude reaction mixture afforded a solid which was washed with CH$_2$Cl$_2$ and two times with ethyl acetate (m.p. 165°–170° C). $^1$H NMR(d$_6$-DMSO) δ 0.7–1.9 (m, 7 H), 2.0 (m, 2 H), 3.0 (s, 2 H), 4.9 (s, 1 H), 7.3–7.8 (m, 9 H), 11.3 (s, 1 H).

EXAMPLE M

4-[2,3-Dihydro-4-hydroxy-6-oxo-2H-pyran-2-yl]-benzonitrile, (±)

The title compound was prepared as described in General Method 1 using 5.0 mL of methyl acetoacetate, 2.0 g of NaH 60% dispersion in oil, 25 mL of 2.0M n-butyl lithium in hexane, 7.6 g of 4-cyanobenzaldehyde and 150 mL of tetrahydrofuran. After addition of the aldehyde, the reaction was stirred for 10 minutes at 0° C. then allowed to warm to room temperature overnight. The crude product was triturated from diethyl ether to afford a solid (m.p. 149°–152° C.). $^1$H NMR (CDCl$_3$) δ 2.80 (dd, 1 H), 2.99 (dd, 1 H), 3.65 (dd, 2 H), 5.75 (dd, 1 H), 7.55 (d, 2 H), 7.75 (d, 2 H).

EXAMPLE N 6-(4-Trifluoromethylphenyl)-5,6-dihydro-4-hydroxy-2-pyran-2-one, (+/−)

The title compound was prepared as described in General Method 1 using 10 mL of methyl acetoacetate, 3.7 g of NaH 60% dispersion in oil, 58 mL of 1.6M n-butyl lithium in hexane, 11.5 g of 4-trifluoromethylbenzaldehyde and 250 mL of tetrahydrofuran. After addition of the aldehyde, the reaction was stirred for 10 minutes at 0° C. then 30 minutes at room temperature. The crude product was triturated from diethyl ether to afford a solid (m.p. 155°–156° C). $^1$H NMR (CDCl$_3$) δ 2.83 (dd, 1 H), 2.99 (dd, 1 H), 3.58 (dd, 2 H), 5.76 (dd, 1 H), 7.50–7.76 (m, 4 H).

EXAMPLE O 6-(3,5-Dichlorophenyl)-5,6-dihydro-4-hydroxy- 2H-pyran-2-one, (+/−)

The title compound was prepared as described in General Method 1 using 2.5 mL of methyl acetoacetate, 1.0 g of NaH 60% dispersion in oil, 12.5 mL of 2.0M n-butyl lithium in hexane, 5.1 g of 3,5-dichlorobenzaldehyde and 75 mL of tetrahydrofuran. After addition of the aldehyde, the reaction was stirred for 10 minutes at 0° C. then allowed to warm to room temperature overnight. The crude product was triturated from diethyl ether to afford a solid (m.p. 135°–137° C.). $^1$H NMR (CDCl$_3$) δ 2.78 (dd, 1 H), 2.97 (dd, 1 H), 3.63 (dd, 2 H), 5.64 (dd, 1 H), 7.31–7.40 (m, 3 H).

EXAMPLE P 5,6-Dihydro-4-hydroxy-6-(pentafluorophenyl)-2H-pyran-2-one, (+/−)

The title compound was prepared as described in General Method 1 using 2.5 mL of methyl acetoacetate, 1.0 g of NaH 60% dispersion in oil, 12.5 mL of 2.0M n-butyl lithium in hexane, 3.4 mL of pentafluorobenzaldehyde and 75 mL of tetrahydrofuran. After addition of the aldehyde, the reaction was stirred for 10 minutes at 0° C. then allowed to warm to room temperature overnight. The crude product was triturated from diethyl ether to afford a solid (m.p. 176°–178° C.). $^1$H NMR (CDCl$_3$) δ 2.89 (dd, 1 H), 3.15 (dd, 1 H), 3.70 (dd, 2 H), 6.02 (dd, 1 H).

EXAMPLE Q 5,6-Dihydro-4-hydroxy-6-(3-methylphenyl)- 2H-pyran-2-one, (+/−)

The title compound was prepared as described in General Method 1 using 2.0 mL of methyl acetoacetate, 0.8 g of NaH 60% dispersion in oil, 10 mL of 2.0M n-butyl lithium in hexane, 2.6 mL of 3-methylbenzaldehyde and 100 mL of tetrahydrofuran. After addition of the aldehyde, the reaction was stirred for 10 minutes at 0° C. then allowed to warm to room temperature overnight. The crude product was triturated from diethyl ether to afford a solid (m.p. 137°–138° C.). $^1$H NMR (CDCl$_3$) δ 2.38 (s, 3 H), 2.88 (dd, 1 H), 2.95 (dd, 1 H), 3.57 (dd, 2 H), 5.68 (dd, 1 H), 7.16–7.33 (m, 4 H).

EXAMPLE R 6-(2-Chlorophenyl)-5,6-dihydro-4-hydroxy- 2H-pyran-2-one, (+/−)

The title compound was prepared as described in General Method 1 using 2.5 mL of methyl acetoacetate, 1.0 g of NaH 60% dispersion in oil, 12.5 mL of 2.0M n-butyl lithium in hexane, 3.3 mL of 2- chlorobenzaldehyde and 75 mL of tetrahydrofuran. After addition of the aldehyde, the reaction was stirred for 10 minutes at 0° C. then stirred for 2 hours at room temperature. The crude product was triturated from diethyl ether to afford a solid (m.p. 124°–125° C.). $^1$H NMR (CDCl$_3$) δ 2.63 (dd, 1 H), 3.10 (dd, 1 H), 3.68 (dd, 2 H), 6.07 (dd, 1 H), 7.3–7.65 (m, 4 H).

EXAMPLE S

6-Butyl-5,6-dihydro-4-hydroxy-6-phenyl-2H-pyran-2-one, (+/−)

The title compound was prepared as described in General Method 1 using 2.7 mL of methyl acetoacetate, 1.1 g of NaH 60% dispersion in oil, 12.5 mL of 2.0M n-butyl lithium in hexane, 5.1 mL of valerophenone and 125 mL of tetrahydrofuran. After addition of the ketone, the reaction was stirred for 10 minutes at 0° C. then allowed to warm to room temperature overnight. The crude product was triturated from diethyl ether to afford a solid (m.p. 124°–126° C.). $^1$H NMR (CDCl$_3$) δ 0.85 (t, 3 H), 1.28 (m, 4 H), 1.97 (m, 2 H), 2.90 (dd, 2 H), 3.30 (dd, 2 H), 7.28–7.42 (m, 5 H).

EXAMPLE T 5,6-Dihydro-4-hydroxy-6-phenyl-6-propyl-2H-pyran-2-one, (+/−)

The title compound was prepared as described in the General Method 1 using 5 mmol of methyl acetoacetate, 5.5 mmol of NaH 60% dispersion in oil, 5.5 mmol of 1.6M n-butyl lithium in hexane, 5.5 mmol of butyrophenone and 14 mL of tetrahydrofuran. After addition of the ketone, the reaction was stirred for 90 minutes at 0° C. The reaction was poured into saturated NH$_4$Cl solution and extracted with ethyl acetate. The organic layer was dried over MgSO$_4$, concentrated, and the residue flash chromatographed using hexane/ethyl acetate 80/20 as eluent. The aldol product was stirred at room temperature in 100 mL of 0.1N NaOH for 3.5 hours. The reaction was worked up as in General Method 1 and the product triturated from diethyl ether to afford a solid (m.p. 131.5°–132° C.). $^1$H NMR (CDCl$_3$) δ 0.88 (t, 3 H), 1.1–1.4 (m, 2 H), 1.95 (m, 2 H), 2.90 (d, 1 H), 2.92 (d, 1 H), 3.25 (d, 1 H), 3.35 (d, 1 H), 7.2–7.4 (m, 5 H).

EXAMPLE U 5,6-Dihydro-6-pentyl-6-phenyl-2H-pyran-2-one, (+/−)

The title compound was prepared as described in General Method 1 using 10 mmol of methyl acetoacetate, 11 mmol of NaH 60% dispersion in oil, 10.5 mmol of 1.6M n-butyl lithium in hexane, 10 mmol of hexanophenone and 28 mL of tetrahydrofuran. Upon concentrating the reaction a solid precipitated out which was triturated with ether and filtered (m.p. 123°–124° C.). $^1$H NMR (CDCl$_3$) δ 0.83 (t, 3 H), 1.1–1.4 (m, 6 H), 1.9–2.0 (m, 2 H), 2.90 (d, 1 H), 2.92 (d, 1 H), 3.25 (d, 1 H), 3.35 (d, 1 H), 7.2–7.5 (m, 5 H).

EXAMPLE V 5,6-Dihydro-6-(3-methylbutyl)-6-phenyl-2H-pyran-2-one, (+/−)

The title compound was prepared as described in General Method 1 using 25 mmol of methyl acetoacetate, 27.5 mmol of NaH 60% dispersion in oil, 26.25 mmol of 1.6M n-butyl lithium in hexane, 25 mmol of isohexanophenone and 70 mL of tetrahydrofuran. Upon concentrating the reaction a solid precipitated out which was triturated with ether and filtered (m.p. 134°–136° C.). $^1$H NMR (CDCl$_3$) δ 0.83 (dd, 6 H), 1.1–1.3 (m, 2 H), 1.4–1.6 (m, 1 H), 1.9–2.1 (m, 2 H), 2.90 (d, 1 H), 2.92 (d, 1 H), 3.25 (d, 1 H), 3.35 (d, 1 H), 7.2–7.5 (m, 5 H).

EXAMPLE W 5,6-Dihydro-6,6-diphenyl-2H-pyran-2-one

The title compound was prepared as described in General Method 1 using 20 mmol of methyl acetoacetate, 22 mmol of NaH 60% dispersion in oil, 21 mmol of 1.6M n-butyl lithium in hexane, 20 mmol of benzophenone and 70 mL of tetrahydrofuran. Upon concentrating the reaction a solid precipitated out which was triturated with ether and filtered (m.p. 170.5°–173° C.). $^1$H NMR (CDCl$_3$) δ 3.18 (s, 2 H), 3.4 (s, 2 H), 7.3–7.5 (m, 10 H).

EXAMPLE X 5,6-Dihydro-6-phenyl-6-(2-phenylethyl)-2H-pyran-2-one, (+/−)

The title compound was prepared as described in General Method 1 using 25 mmol of methyl acetoacetate, 27.5 mmol of NaH 60% dispersion in oil, 26.25 mmol of 1.6M n-butyl lithium in hexane, 25 mmol of 3-phenylpropiophenone and 70 mL of tetrahydrofuran. Upon concentrating the reaction a solid precipitated out which was triturated with ether and filtered (m.p. 130°–130.55,° C.). $^1$H NMR (CDCl$_3$) δ 2.2–2.4 (m, 2 H), 2.4–2.6 (m, 1 H), 2.6–2.8 (m, 1 H), 2.9 (d, 1 H), 3.0 (d, 1 H), 3.3 (d, 1 H), 3.4 (d, 1 H), 7.0–7.5 (m, 15 H).

EXAMPLE Y 5,6-Dihydro-4-hydroxy-6-phenyl-2(1H)-pyridinone (±)

The title compound was prepared by decarboxylation of methyl 6-phenyl-2-,4-dioxopiperidine-3-carboxylate (prepared as per Ashton et al., *Heterocycles* 28: (2) 1015 (1989)) by refluxing in acetonitrile (as per Toda et al., *J. Antibiotics* 23: (2) 173 (1980)). Removal of the solvent gave a solid (m.p. 166°–169° C,). $^1$H NMR (CDCl$_3$) δ 2.77 (dd, 1 H), 2.90 (dd, 1 H), 3.38 (s, 2 H), 4.80 (dd, 1 H), 6.40 (s, 1 H), 7.32–7.46 (m, 5 H).

EXAMPLE Z 5,6-Dihydro-4-hydroxy-6-phenoxymethyl-6-phenyl-2H-pyran-2-one,(+/−)

The title compound was prepared as described in General Method 1 using 0.85 mL of methyl acetoacetate, 350 mg of NaH 60% dispersion in oil, 5 mL of 1.6M n-butyl lithium in hexane, 2.0 g of 2-phenoxy-1-phenyl ethanone and 60 mL of tetrahydrofuran. After addition of the ketone, the reaction was stirred for 15 minutes at 0° C. then allowed to warm to room temperature and stirred for 1 hour. The crude product was triturated from diethyl ether to afford a solid (m.p. 133°–135° C.). $^1$H NMR (DMSO-d$_6$) δ 3.03 (d, 1 H), 3.35 (d, 1 H), 4.18 (dd, 2 H), 4.90 (s, 1 H), 6.92–6.95 (m, 3 H), 7.24–7.49 (m, 7 H), 11.56 (s, 1 H).

EXAMPLE A1

6-(2-Benzo[1,3]dioxol-5-yl-ethyl)-5,6-dihydro-4-hydroxy-6-phenyl-2H-pyran-2-one,(+/−)

The title compound was prepared as described in General Method 1 using 0.22 mL of methyl acetoacetate, 90 mg of NaH 60% dispersion in oil, 1 mL of 2.1M n-butyl lithium in hexane, 500 mg of 3-(3,4-methylenedioxyphenyl) propiophenone and 15 mL of tetrahydrofuran. After addition of the ketone, the reaction was stirred for 15 minutes at 0° C. then allowed to warm to room temperature and stirred for 2 hours. The crude product was triturated from diethyl ether to afford a solid (m.p. 112°–114° C. ). $^1$H NMR (CDCl$_3$) δ 2.20–2.28 (m, 2 H), 2.37–2.44 (m, 1 H), 2.61–2.69 (m, 1 H), 2.95 (dd, 2 H), 3.32 (dd, 2 H), 5.90 (s, 2 H), 6.52–6.70 (m, 3 H), 7.33–7.44 (m, 5 H).

EXAMPLE B1

6-[2-(3,4-Dichlorophenyl)-ethyl]-5,6-dihydro-4-hydroxy-6-phenyl-2H-pyran-2-one,(+/−)

The title compound was prepared as described in General Method 1 using 1.7 mL of methyl acetoacetate, 630 mg of NaH 60% dispersion in oil, 9.85 mL of 1.6M n-butyl lithium in hexane, 4.0 g of 3-(3,4-dichlorophenyl)propiophenone and 150 mL of tetrahydrofuran. After addition of the ketone, the reaction was stirred for 15 minutes at 0° C. then allowed to warm to room temperature and stirred for 4 hours. The crude product was triturated from diethyl ether to afford a solid (m.p. 145°–147° C.). $^1$H NMR (CDCl$_3$) δ 2.18–2.35 (m, 2 H), 2.39–2.50 (m, 1 H), 2.68–2.80 (m, 1 H), 2.96 (dd, 2 H), 3.36 (dd, 2 H), 6.90–7.50 (m, 8 H).

EXAMPLE C1

6-[2-(4-Fluorophenyl)-ethyl]-5,6-dihydro-4-hydroxy-6-phenyl-2H-pyran-2-one (+/−)

The title compound was prepared as described in General Method 1 using 3.1 mL of methyl acetoacetate, 1.2 g of NaH 60% dispersion in oil, 18 mL of 1.6M n-butyl lithium in hexane, 6.0 g of 3-(4-fluorophenyl)propiophenone and 200 mL of tetrahydrofuran. After addition of the ketone, the reaction was stirred for 15 minutes at 0° C. then allowed to warm to room temperature and stirred for 4 hours. The crude product was triturated from diethyl ether to afford a solid (m.p. 155°–157° C. ). $^1$H NMR (CDCl$_3$) δ 2.23–2.29 (m, 2 H), 2.42–2.52 (m, 1 H), 2.67–2.78 (m, 1 H), 2.97 (dd, 2 H), 3.35 (dd, 2 H), 7.34–7.47 (m, 5 H), 6.91–7.07 (m, 4 H).

EXAMPLE D1

5,6-Dihydro-6-hexyl-4-hydroxy-6-phenyl-2H-pyran-2-one (±)

The title compound was prepared as described in General Method 1 using 25 mmol of methyl acetoacetate, 27.5 mmol of NaH 60% dispersion in oil, 26.25 mmol of 1.6M n-butyl lithium in hexane, 25 mmol of heptanophenone and 70 mL of tetrahydrofuran. Upon concentrating the reaction, a solid precipitated out which was triturated with ether and filtered (m.p. 119°–120.5° C.). $^1$H NMR (CDCl$_3$) δ 0.84 (t, 3 H), 1.1–1.4 (m, 8 H), 1.9–2.0 (m, 2 H), 2.89 (d, 1 H), 2.93 (d, 1 H), 3.24 (d, 1 H), 3.35 (d, 1 H), 7.2–7.5 (m, 5 H).

EXAMPLE E1

5,6-Dihydro-4-hydroxy-6-(4-methylpentyl)-6-phenyl-2H-pyran-2-one (±)

The title compound was prepared as described in General Method 1 using 14.2 mmol of methyl acetoacetate, 15.6 mmol of NaH 60% dispersion in oil, 14.9 mmol of 1.6M n-butyl lithium in hexane, 14.2 mmol of isoheptanophenone and 50 mL of tetrahydrofuran. Isoheptanophenone was prepared by reacting the appropriate acid chloride with AlCl$_3$ in benzene as described by Vogel in Practical Organic Chemistry 1978, 770–775. Upon concentrating the reaction, a solid precipitated out which was recrystallized from ethyl acetate (m.p. 124°–125° C.). $^1$H NMR (CDCl$_3$) δ 0.80 (d,d, 6 H), 1.1–1.2 (m, 2 H), 1.15–1.40 (m, 2 H), 1.4–1.5 (m, 1 H), 1.9–2.0 (m, 2 H), 2.88 (d, 1 H), 2.9 (d, 1 H), 3.2 (d, 1 H), 3.3 (d, 1 H), 7.2–7.5 (m, 5 H).

EXAMPLE F1

6-(Cyclopentylmethyl)-5,6-dihydro-4-hydroxy-6-phenyl-2H-pyran-2-one (±)

The title compound was prepared as described in General Method 1 using 25 mmol of methyl acetoacetate, 27.5 mmol of NaH 60% dispersion in oil, 26.25 mmol of 1.6M n-butyl lithium in hexane, 25 mmol of 2-cyclopentyl-1-phenyl-ethanone and 70 mL of tetrahydrofuran. 2-Cyclopentyl-1-phenyl-ethanone was prepared by reacting the appropriate acid chloride with AlCl$_3$ in benzene as described by Vogel in Practical Organic Chemistry 1978, 770–775. Upon concentrating the reaction, a solid precipitated out which was recrystallized from ethyl acetate (m.p. 158°–160° C.). $^1$H NMR (DMSO-d$_6$) δ 0.8–0.9 (m, 1 H), 1.0–1.1 (m, 1 H), 1.2–1.8 (m, 7 H), 1.9–2.1 (m, 2 H), 2.9 (ABq, 2 H), 4.8 (s, 1 H), 7.2–7.4 (m, 5 H), 11.3 (s, 1 H).

EXAMPLE G1

3,4-Dihydro-4'-hydroxy-spiro[naphthalene-1(2H),2'-[2H]pyran]-6'(3'H)-one (±)

The title compound was prepared as described in General Method 1 using 25 mmol of methyl acetoacetate, 27.5 mmol of NaH 60% dispersion in oil, 26.25 mmol of 1.6M n-butyl lithium in hexane, 25 mmol of α-tetralone and 70 mL of tetrahydrofuran. The product was recrystallized from ethyl acetate/diethyl ether (m.p. 117°–119° C.). $^1$H NMR (CDCl$_3$)

δ 1.7–1.9 (m, 1 H), 1.9–2.1 (m, 2 H), 2.1–2.3 (m, 1 H), 2.7–3.0 (m, 2 H), 2.95 (d, 1 H), 3.1 (d, 1 H), 3.5 (s, 2 H), 7.1–7.2 (m, 1 H), 7.2–7.3 (m, 2 H), 7.4–7.5 (m, 1 H).

EXAMPLE H1

3-(3,6-Dihydro-4-hydroxy-6-oxo-2-phenyl-2H-pyran-2-yl)propanoic acid (±)

The title compound was prepared as described in General Method 1 using 25 mmol of methyl acetoacetate, 27.5 mmol of NaH 60% dispersion in oil, 26.25 mmol of 1.6M n-butyl lithium in hexane in 50 mL of tetrahydrofuran and 25 mmol of 3-benzoylpropionic acid sodium salt in 60 mL of tetrahydrofuran. 3-Benzoylpropionic acid sodium salt was prepared by reacting the acid (25 mmol) with hexane washed NaH (26.25 mmol) in tetrahydrofuran at 0° C. for 30 minutes. The crude product was flash chromatographed using $CH_2Cl_2$/MeOH/$CH_3CO_2H$ (90/10/0.2) to give a viscous gum. $^1H$ NMR (CDCl$_3$) δ 2.1–2.6 (m, 4 H), 2.9 (d, 1 H), 3.0 (d, 1 H), 3.3 (d, 1 H), 3.4 (d, 1 H), 7.2–7.5 (m, 5 H).

EXAMPLE I1

4-(3,6-Dihydro-4-hydroxy-6-oxo-2-phenyl-2H-pyran-2-yl) butyricacid (±)

The title compound was prepared as described in General Method 1 using 25 mmol of methyl acetoacetate, 27.5 mmol of NaH 60% dispersion in oil, 26.25 mmol of 1.6M n-butyl lithium in hexane in 50 mL of tetrahydrofuran and 25 mmol of 4-benzoylbutyric acid acid sodium salt in 100 mL of tetrahydrofuran. 4-Benzoylbutyric acid sodium salt was prepared by reacting the acid (25 mmol) with hexane washed NaH (17.5 mmol) in tetrahydrofuran at 0° C. for 25 minutes. The crude product was flash chromatographed using $CH_2Cl_2$/MeOH/$CH_3CO_2H$ (99/1/0.1–97.5/2.5/0.1) to give a solid which was recrystallized from ethyl acetate (m.p. 134°–137° C.). $^1H$ NMR (DMSO-d$_6$) δ 1.1–1.2 (m, 1 H), 1.4–1.6 (m, 1 H), 1.8–2.0 (m, 2 H), 2.0–2.2 (m, 2 H), 2.9 (ABq, 2 H), 4.85 (s, 1 H), 7.2–7.4 (m, 5 H).

EXAMPLE J1

5-(3,6-Dihydro-4-hydroxy-6-oxo-2-phenyl-2H-pyran-2-yl)pentanoic acid (±)

The title compound was prepared as described in General Method 1 using 25 mmol of methyl acetoacetate, 27.5 mmol of NaH 60% dispersion in oil, 26.25 mmol of 1.6M n-butyl lithium in hexane in 50 mL of tetrahydrofuran and 25 mmol of 5-benzoylpentanoic acid sodium salt in 100 mL of tetrahydrofuran. 5-Benzoylpentanoic acid sodium salt was prepared by reacting the acid (25 mmol) with hexane washed NaH (27.5 mmol) in tetrahydrofuran at 0° C. for 25 minutes. The crude solid was recrystallized from ethyl acetate (m.p. 136°–140° C.). $^1H$ NMR (DMSO-d$_6$) δ 0.8–1.0 (m, 1 H), 1.1–1.3 (m, 1 H), 1.3–1.5 (m, 2 H), 1.8–2.0 (m, 2 H), 2.1 (t, 2 H), 2.9 (ABq, 2 H), 4.85 (s, 1 H), 7.2–7.4 (m, 5 H), 11.4 (bs, 1 H), 12.0 (bs, 1 H).

EXAMPLE K1

5,6-Dihydro-4-hydroxy-6-phenyl-6-pyridin-4-yl-2H-pyran-2-one (±)

The title compound was prepared as described in General Method 1 using 90 mmol of ethyl acetoacetate, 99 mmol of NaH 60% dispersion in oil, 95 mmol of 1.6M n-butyl lithium in hexane and 90 mmol of 4-benzoylpyridine and 250 mL of tetrahydrofuran. The reaction mixture was acidified with acetic acid and the crude solid was washed with ice water (m.p. 148°–150° C.).

EXAMPLE L1

5,6-Dihydro-4-hydroxy-6-[(methylphenylamino)methyl]-6-phenyl-2H-pyran-2-one (±)

The 2-(methylphenylamino)-1-phenyl-ethanone was prepared by reacting N-methylaniline (50 mmol), α-bromoacetophenone (50 mmol), triethylamine (55 mmol) in diethyl ether at room temperature overnight. The diethyl ether was evaporated, replaced with p-dioxane, and the mixture ref luxed for 15 hours. The solid triethylamine hydrochloride was filtered. The filtrate was concentrated and the solids were recrystallized from ethyl acetate to afford the desired compound as a solid (m.p. 118°–120° C.).

The title compound was prepared as described in General Method 1 using 6.7 mmol of methyl acetoacetate, 7.3 mmol of NaH 60% dispersion in oil, 7.0 mmol of 1.6M n-butyl lithium in hexane, 6.7 mmol of 2-(methylphenylamino)-1-phenylethanone and 40 mL of tetrahydrofuran. The reaction mixture was acidified to pH 7 with conc. HCl and then taken to pH 3 with acetic acid. The product was flash chromatographed using $CH_2Cl_2$/MeOH (99/1) to give a solid (m.p. 152°–153° C.). $^1H$ NMR (CDCl$_3$) δ 2.9 (d, 1 H), 3.05 (s, 3 H), 3.1 (d, 1 H), 3.2 (d, 1 H), 3.3 (d, 1 H), 3.7 (ABq, 2 H), 6.7–6.8 (m, 3 H), 7.2–7.3 (m, 2 H), 7.3–7.5 (m, 5 H).

EXAMPLE M1

N-Benzyl-4-(3,6-dihydro-4-hydroxy-6-oxo-2-phenyl-2H-pyran-2-yl)-N-methylbutyramide (±)

The 5-oxo-5-phenylpentanoic acid benzyl-methyl amide was prepared by refluxing N-methylbenzylamine (10.5 mmol) and 6-phenyl-3,4-dihydro-pyran-2-one (10.5 mmol) in toluene for one hour. The reaction was allowed to stir overnight at room temperature. It was poured into 100 mL of ethyl acetate and 100 mL of IN HCl. The organic extracts were washed with 100 mL of 1N NaOH, 100 mL of water and dried over MgSO$_4$. The crude product was flash chromatographed ($CH_2Cl_2$/MeOH 98/2) to afford a liquid. $^1H$ NMR (CDCl$_3$) δ 2.0–2.2 (m, 2 H), 2.5 (t, 2 H), 2.93/2.96 (s/s, 3 H), 3.0–3.2 (m, 2 H), 4.5/4.6 (s/s, 2 H), 7.1–7.6 (m, 8 H), 7.8–8.0 (m, 2 H).

The title compound was prepared as described in General Method 1 using 5.6 mmol of methyl acetoacetate, 6.1 mmol of NaH 60% dispersion in oil, 5.9 mmol of 1.6M n-butyl lithium in hexane, 5.6 mmol of 5-oxo-5-phenylpentanoic acid benzyl-methyl amide and 25 mL of tetrahydrofuran. The product was flash chromatographed using $CH_2Cl_2$/MeOH (98/2) to give a solid (m.p. 47°–51° C.). $^1H$ NMR (DMSO-d$_6$) δ 1.1–1.3 (m, 1 H), 1.4–1.6 (m, 1 H), 1.8–2.0 (m, 2 H), 2.2–2.4 (m, 2 H), 2.75/2.81 (s/s 3 H), 2.85–3.1 (m, 2 H), 4.4/4.5 (s/s, 2 H), 4.85/4.9 (s/s 1 H), 7.1–7.4 (m, 10 H), 11.36/11.38 (s/s, 1 H).

GENERAL METHOD 2

The thiotosylate reagents were prepared by reacting equal molar quantities of alkyl halide and potassium thiotosylate in absolute ethanol and refluxing for 24 hours or in DMF and stirring at room temperature for 12 to 72 hours. The solvent was stripped off and the residue was taken up in ethyl acetate and washed with water. Alternatively, water was added and the aqueous layer was extracted with diethyl ether or ethyl acetate. The organic extracts were dried over MgSO$_4$ and concentrated in vacuo.

Alternatively, the thiotosylate reagents were prepared as described by M. G. Ranasinghe and P. L. Fuchs in *Syn. Comm.* 18(3): 227 (1988).

EXAMPLE AA

Benzyl-p-toluenethiosulfonate

The title compound was prepared as described in General Method 2 using 0.05 mol of benzyl chloride, 0.05 moles of potassium thiotosylate in 150 mL of ethanol. The residue was dissolved in hexane and seeded with a crystal of the product to afford 10.8 g (77%) of benzyl-p-toluenethiosulfonate (m.p. 52°–56.5° C.). $^1$H NMR (CDCl$_3$) δ 2.45 (s, 3 H), 4.26 (s, 2 H), 7.18–7.30 (m, 7 H), 7.74 (d, 2 H).

EXAMPLE BB

2-Phenylethyl-p-toluenethiosulfonate

The title compound was prepared according to General Method 2 using phenethyl bromide (0.088 mmol), potassium thiotosylate(0.088 mol), and absolute ethanol (250 mL). A clear liquid was obtained which was used without purification. $^1$H NMR (CDCl$_3$) δ 2.47 (s, 3 H), 2.92 (t, 2 H), 3.24 (t, 2 H), 7.1–7.4 (m, 7 H), 7.84 (d, 2 H).

EXAMPLE CC

3-Phenylpropyl-p-toluenethiosulfonate

The title compound was prepared as described in General Method 2 using 1-bromo-3-phenylpropane (0.044 mmol), potassium thiotosylate (0.044 mmol) and absolute ethanol (125 mL) to give an oil which was used without purification. $^1$H NMR (CDCl$_3$) δ 1.95 (quint., 2 H), 2.459 (s, 3 H), 2.63 (t, 2 H), 2.95 (t, 2 H), 7.0–7.4 (m, 8 H), 7.7 (d, 2 H).

EXAMPLE DD

2-Phenoxyethyl-p-toluenethiosulfonate

The title compound was prepared as described in General Method 2 using 2-phenoxyethyl bromide (0.025 mmol), potassium thiotosylate (0.025 mmol) and DMF (100 mL) to give a solid. $^1$H NMR (CDCl$_3$) δ 2.45 (s, 3 H), 3.34 (t, 2 H), 4.14 (t, 2 H), 6.80 (d, 2 H), 6.95 (t, 1 H), 7.26 (t, 2 H), 7.35 (d, 2 H), 7.82 (d, 2 H).

GENERAL METHOD 3

The 3-bromo-5,6-dihydro-4-hydroxy-2H-pyran-2-one intermediates were prepared by reacting equimolar amounts of the requisite 6-substituted 5,6-dihydro-4-hydroxy-2H-pyran-2-ones (prepared in General Method 1) with N-bromosuccinimide (1.0 equiv.) in dry t-butanol in the dark. The solvent was evaporated, and the residue was partitioned between chloroform and water. The organic layer was washed with brine, dried (MgSO$_4$), and concentrated.

EXAMPLE AAA

3-Bromo-5,6-dihydro-4-hydroxy-6,6-diphenyl-2H-pyran-2-one

The title compound was prepared as described in General Method 3 using 4.0 mmol of 5,6-dihydro-4-hydroxy-6,6-diphenyl-2H-pyran-2-one (prepared in Example W) and 4.0 mmol of NBS. The product was obtained as a solid. $^1$H NMR (DMSO-d$_6$) δ 3.68 (s, 2 H), 7.27–7.40 (m, 10 H).

EXAMPLE BBB

3-Bromo-5,6-dihydro-4-hydroxy-6-phenyl-6-(2-phenylethyl)-2H-pyran-2-one, (+/−)

The title compound was prepared as described in General Method 3 using 2.0 mmol of 5,6-dihydro-4-hydroxy-6-phenyl-6-(2-phenylethyl)-2H-pyran-2-one (prepared in Example X) and 2.0 mmol of NBS. $^1$H NMR (DMSO-d$_6$) δ 2.16–2.58 (m, 4 H), 3.30 (m, 2 H), 7.04–7.60 (m, 10 H).

EXAMPLE CCC

3-Bromo-5,6-dihydro-4-hydroxy-(3-methylbutyl)-6-phenyl-2H-pyran-2-one, (+/−)

The title compound was prepared as described in General Method 3 using 2.0 mmol of 5,6-dihydro-4-hydroxy-6-(3-methylbutyl)-6-phenyl-2H-pyran-2-one (prepared in Example V) and 2.0 mmol of NBS $^1$H NMR (DMSO-d$_6$) δ 0.80 (m, 6 H), 1.00 (m, 1 H), 1.14 (m, 1 H), 1.42 (m, 1 H), 1.95 (m, 2 H), 3.35 (m, 2 H), 7.25–7.52 (m, 5 H).

EXAMPLE DDD

5-[5-Bromo-4-hydroxy-6-oxo-2-phenyl-3,6-dihydro-2H-pyran-2-yl]pentanoic acid, (+/−)

The title compound was prepared as described in General Method 3 using 1.4 mmol of 5-[4-hydroxy-6-oxo-2-phenyl-3,6-dihydro-2H-pyran-2-yl]pentanoic acid (prepared in Example J1) and 1.4 mmol of NBS. $^1$H NMR (DMSO-d$_6$) δ 0.94 (m, 1 H), 1.22–1.40 (m, 3 H), 1.92 (m, 2 H), 2.13 (t, 2 H), 3.28 (q, 2 H), 7.16–7.52 (m, 5 H).

GENERAL METHOD 4

The desired compounds were prepared by adding the 5,6-dihydro-2H-pyran-2-one, absolute ethanol, the p-toluenethiosulfonate reagent, and Et$_3$N to a reaction vessel. The solution was stirred at room temperature to reflux for 4 hours to one week. The solvent was stripped off and the residue partitioned between 1N HCl and CH$_2$Cl$_2$ or ethyl acetate. The layers were separated and the aqueous layer was extracted with CH$_2$Cl$_2$ or ethyl acetate. The organic layers were combined and dried over MgSO$_4$.

EXAMPLE 1

5,6-Dihydro-4-hydroxy-6-phenyl-3-[(phenylmethyl)thio]-2H-pyran-2-one (±).

The title compound was prepared as described in General Method 4 using 2.1 mmol of 5,6-dihydro-4-hydroxy-6-phenyl-2H-pyran-2-one, 10 mL of absolute EtOH, 2.3 mmol of benzyl-p-toluenethiosulfonate and 2.3 mmol of Et$_3$N in 5 mL of absolute EtOH. The solution was stirred for 3 days at room temperature. Concentration in vacuo gave a solid which was broken up and made into a slurry in diethyl ether and ethyl acetate. The solid was filtered off and the mother liquors were concentrated and flash chromatographed on silica gel using CH$_2$Cl$_2$/MeOH (99/1 to 97/3) as eluants. The combined crops gave 0.365 g (55%) of the desired product as a solid (m.p. 150°–151.5° C.). $^1$H NMR (CDCl$_3$) δ 2.65 (dd, 1 H), 2.78 (dd, 1 H), 3.85 (d, 1 H), 3.94 (d, 1 H), 5.29 (dd, 1 H), 7.2–7.4 (m, 11 H).

EXAMPLE 2

5,6-Dihydro-4-hydroxy-6-phenyl-3-[(2-phenylethyl)thio]-2H-pyran-2-one (±).

The title compound was prepared as described in General Method 4 using 2.1 mmol of 5,6-dihydro-4-hydroxy-6- phenyl-2H-pyran-2-one, 6 mL of absolute EtOH, 2.3 mmol) of 2-phenylethyl-p-toluenethiosulfonate in 6 mL of absolute EtOH and 2.3 mmol of triethylamine in 3 mL of absolute EtOH. The reaction was stirred at room temperature for 4 days. The product was purified by flash chromatography using $CH_2Cl_2$/MeOH(99/1 to 97/3) as eluants. The viscous paste which was isolated was triturated from ether to yield a solid (m.p. 98°–99° C.) $^1$H NMR ($CDCl_3$) δ 2.8–3.1 (m, 6 H), 5.3 (dd, 1 H), 7.1–7.7 (m, 11 H).

EXAMPLE 3

5,6-Dihydro-4-hydroxy-6-phenyl-3-[(3-phenylpropyl)thio]-2H-pyran-2-one (±).

The title compound was prepared as described in General Method 4 using 2.63 mmol of 5,6-dihydro-4-hydroxy-6-phenyl-2H-pyran-2-one, 7 mL of absolute EtOH, 2.76 mmol of 3-phenylpropyl-p-toluenethiosulfonate in 6 mL of absolute EtOH and 2.89 mmol of triethylamine in 2 mL of absolute EtOH. The reaction was stirred at room temperature for 2 days. The product was triturated from ethyl acetate as a solid (m.p. 134°–135° C.). $^1$H NMR ($CDCl_3$) δ 1.8 (quint., 2 H), 2.6–2.8 (m, 4 H), 2.87 (dd, 1 H), 3.01 (dd, 1 H), 5.43 (dd, 1 H), 7.1–7.5 (m, 10 H), 7.81 (bs, 1 H).

EXAMPLE 4

5,6-Dihydro-4-hydroxy-6-phenyl-3-[(2-phenoxyethyl) thio]-2H-pyran-2-one (±).

The title compound was prepared as described in General Method 4 using 0.54 mmol of 5,6-dihydro-4-hydroxy-6-phenyl-2H-pyran-2-one, 7 mL of absolute EtOH, 0.57 mmol of 2-phenoxyethyl-p-toluenethiosulfonate in 6 mL of absolute EtOH and 0.06 mmol of triethylamine in 2 mL of absolute EtOH. The reaction was stirred at room temperature for 2 days. The product was flash chromatographed and triturated from diethyl ether to give a solid (m.p. 107°–108° C.). $^1$H NMR (DMSO-$d_6$) δ 2.80(dd, 1 H), 2.9–3.0 (m, 2 H), 3.08 (dd, 1 H), 4.07 (t, 2 H), 5.47 (dd, 1 H), 6.9–7.0 (m, 3 H), 7.2–7.5 (m, 7 H).

EXAMPLE 5

5,6-Dihydro-4-hydroxy-6-(2-methylpropyl)-6-phenyl-3-[(phenylmethyl)thio]-2H-pyran-2-one (±)

The title compound was prepared as described in General Method 4 using 0.61 mmol of 5,6-dihydro-4-hydroxy-6-(2-methylpropyl)-6-phenyl-2H-pyran-2-one, 5 mL of absolute EtOH, 0.67 mmol of benzyl-p-toluenethiosulfonate in 3 mL of absolute EtOH and 0.67 mmol of triethylamine in 2 mL of absolute EtOH. The reaction was stirred at room temperature for 18 hours. The product was flash chromatographed ($CH_2Cl_2$/MeOH 99.5/0.5) to afford a viscous oil. $^1$H NMR ($CDCl_3$) δ 0.72 (d, 3 H), 0.90 (d, 3 H), 1.5–1.7 (m, 1 H), 1.81 (dd, 1 H), 1.91 (dd, 1 H), 2.95 (ABq, 2 H), 3.53 (d, 1 H), 3.75 (d, 1 H), 6.8–6.9 (m, 2 H), 7.1–7.4 (m, 8 H).

EXAMPLE 6

5,6-Dihydro-4-hydroxy-6-(2-methylpropyl)-6-phenyl-3-[(2-phenylethyl)thio]-2H-pyran-2-one (±)

The title compound was prepared as described in General Method 4 using 0.61 mmol of 6-i-butyl-5,6-dihydro-4-hydroxy-6-(2-methylpropyl)-6-phenyl-2H-pyran-2-one, 5 mL of absolute EtOH, 0.67 mmol of 2-phenylethyl-p-toluenethiosulfonate in 3 mL of absolute EtOH and 0.67 mmol of triethylamine in 2 mL of absolute EtOH. The reaction was stirred at room temperature for 18 hours. The product was flash chromatographed $CH_2Cl_2$/MeOH 99.5/0.5) to afford a viscous oil. $^1$H NMR ($CDCl_3$) δ 0.75 (d, 3 H), 0.89 (d, 3 H), 1.5–1.7 (m, 1 H), 1.87 (dd, 1 H), 1.95 (dd, 1 H), 2.2–2.3 (m, 1 H), 2.4–2.5 (m, 1 H), 2.6–2.8 (m, 1 H), 3.13 (ABq, 2 H), 6.90–6.95 (m, 2 H), 7.1–7.4 (m, 8 H).

EXAMPLE 7

5-(3-Chlorophenyl)-2-[(2-phenylethyl)thio-1,3-cyclohexanedione 5-(3-Chlorophenyl)-1,3-cyclohexanedione can be prepared as described in J. Med. Chem. 1992, 35, 19, 3429–3447.

To a 50 mL reaction flask was added 0.30 g (1.35 mmol) of 5-(3-chlorophenyl)-1,3-cyclohexanedione in 5 mL of absolute EtOH, 0.43 g (1.48 mmol) of 2-phenylethyl-p-toluenethiosulfonate in 3 mL of absolute EtOH and 0.16 g (1.62 mmol) of $Et_3N$ in 2 mL of absolute EtOH. The reaction was stirred at room temperature for 27 hours. The EtOH was removed in vacuo and the residue dissolved in 200 mL of diethyl ether and 100 mL of 1N HCl. The aqueous layer was extracted with 2×100 mL of diethyl ether. The organic extracts were combined, dried over $MgSO_4$, and concentrated. The residue was flash chromatographed using $CH_2Cl_2$/MeOH 99/1 to give a solid (m.p.69°–73° C.). $^1$H NMR($CDCl_3$) δ 2.5–3.1 (m, 8 H), 3.3 (m, 1 H), 7.1–7.4 (m, 9 H), 7.9 (bs, 1 H).

EXAMPLE 8

5,6-Dihydro-4-hydroxy-6-(4-methoxyphenyl)-3-[(phenylmethyl)thio]-2H-pyran-2-one, (+/−)

The title compound was prepared as described in General Method 4 using 300 mg of 5,6-dihydro-4-hydroxy-6-(4-methoxyphenyl)-2H-pyran-2-one, 500 mg of benzyl-p-toluenethiosulfonate and 1.0 mL of triethylamine in 10 mL of absolute ethanol. The solution was stirred overnight at room temperature. Purification by flash chromatography using $CH_2Cl_2$/methanol (100/0 to 95/5) as eluent gave a viscous oil which was triturated with diethyl ether to afford a solid (m.p.168°–170° C). $^1$H NMR ($CDCl_3$) δ 2.60 (dd, 1 H), 2.77 (dd, 1 H), 3.82 (s, 3 H), 3.89 (dd, 2 H), 5.23 (dd, 1 H), 6.89–7.33 (m, 10 H).

EXAMPLE 9

5,6-Dihydro-4-hydroxy-6-(4-methylthiophenyl)-3-[(phenylmethyl)thio]-2H-pyran-2-one, (+/−)

The title compound was prepared as described in General Method 4 using 480 mg of 5,6-dihydro-4-hydroxy-6-(4-methylthiophenyl)-2H-pyran-2-one, 620 mg of benzyl-p-toluenethiosulfonate and 0.34 mL of triethylamine in 10 mL of absolute ethanol. The solution was stirred for 3 days at room temperature. Purification by flash chromatography using $CH_2Cl_2$/methanol (100/0 to 95/5) as eluent gave a viscous oil which was triturated with diethyl ether to afford a solid (m.p. 185°–188° C.) $^1$H NMR ($CDCl_3$) δ 2.49 (s, 3 H), 2.62 (dd, 1 H), 2.75 (dd, 1 H), 3.90 (dd, 2 H), 5.25 (dd, 1 H), 7.19–7.32 (m, 10 H).

EXAMPLE 10

5,6-Dihydro-4-hydroxy-6-(4-methylphenyl)-3-[(phenylmethyl)thio]-2H-pyran-2-one, (+/−)

The title compound was prepared as described in General Method 4 using 123 mg of 5,6-dihydro-4-hydroxy-6-(4- methylphenyl)-2H-pyran-2-one, 170 mg of enzyl-p-toluenethiosulfonate and 0.90 mL of triethylamine in 3 mL of absolute ethanol. The solution was stirred for 18 hours at room temperature. The crude product was triturated with diethyl ether to afford a solid (m.p. 166°–167° C.). $^1$H NMR (CDCl$_3$) δ 2.36 (s, 3 H), 2.62 (dd, 1 H), 2.77 (dd, 1 H), 3.94 (dd, 2 H), 5.25 (dd, 1 H), 7.19–7.32 (m, 10 H).

EXAMPLE 11

5,6-Dihydro-4-hydroxy-6-[4-(1,1-dimethylethyl) phenyl]-3-[(phenylmethyl)thio]-2H-pyran-2-one, (+/−)

The title compound was prepared as described in General Method 4 using 445 mg of 5,6-dihydro-4-hydroxy-6-[4-(1,1-dimethylethyl)phenyl]-2H-pyran-2-one, 550 mg of benzyl-p-toluenethiosulfonate and 0.3 mL of triethylamine in 10 mL of absolute ethanol. The solution was stirred for 3 days at room temperature. The crude product was triturated with diethyl ether to afford a solid (m.p. 140°–142° C.). $^1$H NMR (CDCl$_3$) δ 1.32 (s, 9 H), 2.65 (dd, 1 H), 2.79 (dd, 1 H), 3.89 (dd, 2 H), 5.27 (dd, 1 H), 7.18–7.43 (m, 10 H).

EXAMPLE 12

6-(4-Chlorophenyl)-5,6-dihydro-4-hydroxy-3-[(phenylmethyl)thio]-2H-pyran-2-one, (+/−)

The title compound was prepared as described in General Method 4 using 250 mg of 6-(4-chlorophenyl)-5,6-dihydro-4-hydroxy-2H-pyran-2-one, 315 mg of benzyl-p-toluenethiosulfonate and 0.16 mL of triethylamine in 8 mL of absolute ethanol. The solution was stirred overnight at room temperature. Purification by flash chromatography using CH$_2$Cl$_2$/methanol (100/0 to 95/5) as eluent gave a viscous oil which was triturated with diethyl ether to afford a solid (m.p. 167°–170° C.). $^1$H NMR (CDCl$_3$) δ 2.62 (dd, 1 H), 2.74 (dd, 1 H), 3.90 (dd, 2 H), 5.21 (dd, 1 H), 7.23–7.41 (m, 10 H).

EXAMPLE 13

6-(3-Chlorophenyl)-5,6-dihydro-4-hydroxy-3-[(phenylmethyl)thio]-2H-pyran-2-one, (+/−)

The title compound was prepared as described in General Method 4 using 300 mg of 6-(3-chlorophenyl)-5,6-dihydro-4-hydroxy-2H-pyran-2-one, 450 mg of benzyl-p-toluenethiosulfonate and 1.0 mL of triethylamine in 10 mL of absolute ethanol. The solution was stirred overnight at room temperature. Purification by flash chromatography using CH$_2$Cl$_2$/methanol (100/0 to 95/5) as eluent gave a viscous oil which was triturated with diethyl ether to afford a solid (m.p. 139°–142° C.). $^1$H NMR (CDCl$_3$) δ 2.64 (dd, 1 H), 2.73 (dd, 1 H), 3.89 (dd, 2 H), 5.25 (dd, 1 H), 7.18–7.41 (m, 10 H).

EXAMPLE 14

5,6-Dihydro-3-[(2-phenylethyl)thio]-6-[4-(phenylmethoxy)phenyl]-2H-pyran-2-one, (+/−)

The title compound was prepared as described in General Method 4 using 109 mg of 5,6-dihydro-4-hydroxy-6-[4-(phenylmethoxy)phenyl]-2H-pyran-2-one, 114 mg of 2-phenylethyl-p-toluenethiosulfonate and 0.06 mL of triethylamine in 3 mL of absolute ethanol. The solution was stirred overnight at room temperature. Purification by flash chromatography using CH$_2$Cl$_2$/methanol (100/0 to 95/5) as eluent gave a viscous oil which was triturated with diethyl ether to afford a solid (m.p. 99°–101° C.). $^1$H NMR (CDCl$_3$) δ 2.78 (dd, 1 H), 2.85 (dd, 1 H), 2.92–3.11 (m, 4 H), 5.07 (s, 2 H), 5.30 (dd, 1 H), 6.97–7.44 (m, 14 H), 7.62 (s, 1 H).

EXAMPLE 15

5,6-Dihydro-6-(4-methoxyphenyl)-3-[(2-phenylethyl)thio]-2H-pyran-2-one, (+/−)

The title compound was prepared as described in General Method 4 using 300 mg of 5,6-dihydro-4-hydroxy-6-(4-methoxyphenyl)-2H-pyran-2-one, 500 mg of 2-phenylethyl-p-toluenethiosulfonate and 1.0 mL of triethylamine in 10 mL of absolute ethanol. The solution was stirred overnight at room temperature. The crude product was triturated with diethyl ether to afford a solid (m.p. 112°–115° C.). $^1$H NMR (CDCl$_3$) δ 2.78 (dd, 1 H), 2.86 (dd, 1 H), 2.92–3.11 (m, 4 H), 3.81 (s, 3 H), 5.31 (dd, 1 H), 6.91–7.35 (m, 10 H).

EXAMPLE 16

5,6-Dihydro-6-(4-methylthiophenyl)-3-[(2-phenylethyl)thio]-2H-pyran-2-one, (+/−)

The title compound was prepared as described in General Method 4 using 430 mg of 5,6-dihydro-4-hydroxy-6-(4-methylthiophenyl)-2H-pyran-2-one, 585 mg of 2-phenylethyl-p-toluenethiosulfonate and 0.3 mL of triethylamine in 10 mL of absolute ethanol. The solution was stirred for 3 days at room temperature. The crude product was triturated with diethyl ether to afford a solid (m.p. 135°–137° C.). $^1$H NMR (CDCl$_3$) δ 2.48 (s, 3 H), 2.77–3.10 (m, 6 H), 5.32 (dd, 1 H), 7.16–7.33 (m, 9 H), 7.63 (s, 1 H).

EXAMPLE 17

5,6-Dihydro-6-(4-methylphenyl)-3-[(2-phenylethyl)thio]-2H-pyran-2-one, (+/−)

The title compound was prepared as described in General Method 4 using 500 mg of 5,6-dihydro-4-hydroxy-6-(4-methylphenyl)-2H-pyran-2-one, 720 mg of 2-phenylethyl-p-toluenethiosulfonate and 0.4 mL of triethylamine in 12 mL of absolute ethanol. The solution was stirred overnight at room temperature. Purification by flash chromatography using CH$_2$Cl$_2$/methanol (100/0 to 95/5) as eluent gave a viscous oil which was triturated with diethyl ether to afford a solid (m.p. 112°–113° C.). $^1$H NMR (CDCl$_3$) δ 2.36 (s, 3 H), 2.79 (dd, 1 H), 2.84 (dd, 1 H), 2.91–3.10 (m, 4 H), 5.33 (dd, 1 H), 7.16–7.33 (m, 9 H), 7.61 (s, 1 H).

EXAMPLE 18

6-[1,1'-Biphenyl]-4-yl-5,6-dihydro-3-[(2-phenylethyl)thio]-2H-pyran-2-one, (+/−)

The title compound was prepared as described in General Method 4 using 200 mg of 5,6-dihydro-4-hydroxy-6-[1,1'-biphenyl]-4-yl-2H-pyran-2-one, 300 mg of 2-phenylethyl-p-toluenethiosulfonate and 1.0 mL of triethylamine in 10 mL of absolute ethanol. The solution was stirred overnight at room temperature. Purification by flash chromatography using CH$_2$Cl$_2$/methanol (100/0 to 95/5) as eluent gave a viscous oil which was triturated with diethyl ether to afford a solid (m.p. 130°–133° C.). $^1$H NMR (CDCl$_3$) δ 2.84–2.89 (m, 2 H), 2.96–3.12 (m, 4 H), 5.42 (dd, 1 H), 7.08–7.67 (m, 15 H).

EXAMPLE 19

5,6-Dihydro-6-[4-(1,1-dimethylethyl)phenyl]-3-[(2-phenylethyl)thio]-2H-pyran-2-one, (+/−)

The title compound was prepared as described in General Method 4 using 430 mg of 5,6-dihydro-4-hydroxy-6-[4-(1, 1-dimethylethyl)phenyl)-2H-pyran-2-one, 560 mg of 2-phenylethyl-p-toluenethiosulfonate and 0.28 mL of triethylamine in 10 mL of absolute ethanol. The solution was stirred for 3 days at room temperature. The crude product was triturated with diethyl ether to afford a solid (m.p. 130°–131° C.). $^1$H NMR (CDCl$_3$) δ 1.31 (s, 9 H), 2.79–2.88 (m, 2 H), 2.94–3.11 (m, 4 H), 5.34 (dd, 1 H), 7.16–7.43 (m, 9 H), 7.61 (s, 1 H).

EXAMPLE 20

6-(3-Chlorophenyl)-5,6-dihydro-3-[(2-phenylethyl)thio]-2H-pyran-2-one, (+/−)

The title compound was prepared as described in General Method 4 using 300 mg of 6-(3-chlorophenyl)-5,6-dihydro-4-hydroxy-2H-pyran-2-one, 500 mg of 2-phenylethyl-p-toluenethiosulfonate and 1.0 mL of triethylamine in 10 mL of absolute ethanol. The solution was stirred overnight at room temperature. Purification by flash chromatography using CH$_2$Cl$_2$/methanol (100/0 to 95/5) as eluent gave a viscous oil which was triturated with diethyl ether to afford a solid (m.p. 99°–100° C.). $^1$H NMR (CDCl$_3$) δ 2.78–2.91 (m, 2 H), 2.97–3.13 (m, 4 H), 5.32 (dd, 1 H), 7.17–7.43 (m, 9 H), 7.62 (s, 1 H).

EXAMPLE 21

6-[[(1,1'-Biphenyl)-4-yloxy]methyl]-5,6-dihydro-3-[(2-phenylethyl)thio]-2H-pyran-2-one, (+/−)

The title compound was prepared as described in General Method 4 using 150 mg of 6-[[(1,1'-biphenyl)-4-yloxy]methyl]-5,6-dihydro-4-hydroxy-2H-pyran-2-one, 185 mg of 2-phenylethyl-p-toluenethiosulfonate and 1.0 mL of triethylamine in 5 mL of absolute ethanol. The solution was stirred overnight at room temperature. Purification by flash chromatography using CH$_2$Cl$_2$/methanol (100/0 to 95/5) as eluent gave a viscous oil which was triturated with diethyl ether to afford a solid (m.p. 124°–126° C.). $^1$H NMR (CDCl$_3$) δ 2.77 (dd, 1 H), 2.88 (dd, 1 H), 2.95–3.10 (m, 4 H), 4.19–4.28 (m, 2 H), 4.71–4.76 (m, 1 H), 6.96–7.56 (m, 14 H), 7.65 (s, 1 H).

EXAMPLE 22

6-[1,1'-Biphenyl]-4-yl-6-butyl-5,6-dihydro-4-hydroxy-3-[(2-phenylethyl)thio]-2H-pyran-2-one (±)

The title compound was prepared as described in General Method 4 using (0.388 mmol) of 6-[1,1'-biphenyl]-4-yl-6-butyl-5,6-dihydro-4-hydroxy-2H-pyran-2-one, 5 mL of absolute EtOH, (0.407 mmol) of 2-phenylethyl-p-toluenethiosulfonate in 3 mL of absolute EtOH and (0.426 mmol) of triethylamine in 2 mL of absolute EtOH. The reaction was stirred at room temperature overnight. The product was flash chromatographed(CH$_2$Cl$_2$/MeOH 99/1) to afford a solid which was recrystalized from ethyl acetate/diethyl ether. (m.p. 100°–104° C.). $^1$H NMR (CDCl$_3$) δ 0.86 (t, 3 H), 1.15–1.5 (m, 4 H),1.9–2.1(m, 2 H),2.2–2.5 (m, 2 H), 2.5–2.8 (m, 2 H), 3.2 (ABq, 2 H), 6.8–6.9 (m, 2 H),7.1–7.2 (m, 3 H),7.3–7.7 (m, 9 H).

EXAMPLE 23

4-[2,3-Dihydro-4-hydroxy-6-oxo-5-[(phenylmethyl)thio]-2H-pyran-2-yl]benzonitrile, (+/−)

The title compound was prepared as described in General Method 4 using 250 mg of 4-[2,3-dihydro-4-hydroxy-6-oxo-2H-pyran-2-yl]benzonitrile, 385 mg of benzyl-p-toluenethiosulfonate and 1.0 mL of triethylamine in 10 mL of absolute ethanol. The solution was stirred overnight at room temperature. Purification by flash chromatography using CH$_2$Cl$_2$/methanol (100/0 to 95/5) as eluent gave a viscous oil which was triturated with diethyl ether to afford a solid (m.p. 148°–151C.). $^1$H NMR (CDCl$_3$) δ 2.66–2.75 (m, 2 H), 3.91 (dd, 2 H), 5.33 (dd, 1 H), 7.20–7.72 (m, 10 H).

EXAMPLE 24

6-(4-Trifluoromethylphenyl)-5,6-dihydro-4-hydroxy-3-[(phenylmethyl)thio]-2H-pyran-2-one, (+/−)

The title compound was prepared as described in General Method 4 using 211 mg of 6-(4-trifluoromethylphenyl)-5,6-dihydro-4-hydroxy-2H-pyran-2-one, 273 mg of benzyl-p-toluenethiosulfonate and 1.0 mL of triethylamine in 10 mL of absolute ethanol. The solution was stirred overnight at room temperature. Purification by flash chromatography using CH$_2$Cl$_2$/methanol (100/0 to 95/5) as eluent gave a viscous oil which was triturated with diethyl ether to afford a solid (m.p. 183°–186° C.). $^1$H NMR (CDCl$_3$) δ 2.65–2.77 (m, 2 H), 3.92 (dd, 2 H), 5.35 (dd, 1 H), 7.19–7.68 (m, 10 H).

EXAMPLE 25

6-(3,5-Dichlorophenyl)-5,6-dihydro-4-hydroxy-3-[(phenylmethyl)thio]-2H-pyran-2-one, (+/−)

The title compound was prepared as described in General Method 4 using 250 mg of 6-(3,5-dichlorophenyl)-5,6-dihydro-4-hydroxy-2H-pyran-2-one, 320 mg of benzyl-p-toluenethiosulfonate and 1.0 mL of triethylamine in 10 mL of absolute ethanol. The solution was stirred overnight at room temperature. Purification by flash chromatography using CH$_2$Cl$_2$/methanol (100/0 to 95/5) as eluent gave a viscous oil which was triturated with diethyl ether to afford a solid (m.p. 147°–149° C.). $^1$H NMR (CDCl$_3$) δ 2.61–2.74 (m, 2 H), 3.90 (dd, 2 H), 5.21 (dd, 1 H), 7.18–7.36 (m, 9 H).

EXAMPLE 26

6-(Pentafluorophenyl)-5,6-dihydro-4-hydroxy-3-[(phenylmethyl)thio]-2H-pyran-2-one, (+/−)

The title compound was prepared as described in General Method 4 using 226 mg of 6-(pentafluorophenyl)-5,6-dihydro-4-hydroxy-2H-pyran-2-one, 269 mg of benzyl-p-toluenethiosulfonate and 1.0 mL of triethylamine in 10 mL of absolute ethanol. The solution was stirred overnight at room temperature. Purification by flash chromatography using CH$_2$Cl$_2$/methanol (100/0 to 95/5) as eluent gave a viscous oil which was triturated with diethyl ether to afford a solid (m.p. 113°–115° C.). $^1$H NMR (CDCl$_3$) δ 2.50 (dd, 1 H), 3.14 (dd, 1 H), 3.90 (dd, 2 H), 5.57 (dd, 1 H), 7.19–7.365 (m, 6 H).

EXAMPLE 27

5,6-Dihydro-4-hydroxy-6-(3-methylphenyl)-3-[(2-phenylethyl)thio]-2H-pyran-2-one, (+/−)

The title compound was prepared as described in General Method 4 using 300 mg of 5,6-dihydro-4-hydroxy-6-(3-methylphenyl)-2H-pyran-2-one, 515 mg of 2-phenylethyl-p-toluenethiosulfonate and 1.0 mL of triethylamine in 10 mL of absolute ethanol. The solution was stirred overnight at room temperature. Purification by flash chromatography using $CH_2Cl_2$/methanol (100/0 to 95/5) as eluent gave a viscous oil which was triturated with diethyl ether to afford a solid (m.p. 81°–83° C.). $^1H$ NMR ($CDCl_3$) δ 2.38 (s, 3 H), 2.78–3.10 (m, 6 H), 5.35 (dd, 1 H), 7.17–7.34 (m, 9 H), 7.61 (s, 1 H).

EXAMPLE 28

6-(2-chlorophenyl)-5,6-dihydro-4-hydroxy-3-[(phenylmethyl)thio]-2H-pyran-2-one, (+/−)

The title compound was prepared as described in General Method 4 using 200 mg of 6-(2-chlorophenyl)-5,6-dihydro-4-hydroxy-2H-pyran-2-one, 300 mg of benzyl-p-toluenethiosulfonate and 1.0 mL of triethylamine in 10 mL of absolute ethanol. The solution was stirred overnight at room temperature. Purification by flash chromatography using $CH_2Cl_2$/methanol (100/0 to 95/5) as eluent gave a viscous oil which was triturated with diethyl ether to afford a solid (m.p. 89°–91° C.). $^1H$ NMR ($CDCl_3$) δ 2.58 (dd, 1 H), 2.80 (dd, 1 H), 3.92 (dd, 2 H), 5.64 (dd, 1 H), 7.20–7.67 (m, 10 H).

EXAMPLE 29

6-Butyl-5,6-dihydro-4-hydroxy-6-phenyl-3-[(phenylmethyl)thio]-2H-pyran-2-one (+/−)

The title compound was prepared as described in General Method 4 using 400 mg of 6-butyl-5,6-dihydro-4-hydroxy-6-phenyl-2H-pyran-2-one, 540 mg of benzyl-p-toluenethiosulfonate and 1.0 mL of triethylamine in 10 mL of absolute ethanol. The solution was stirred overnight at room temperature. Purification by flash chromatography using $CH_2Cl_2$/methanol (100/0 to 95/5) as eluent gave a viscous oil. $^1H$ NMR ($CDCl_3$) δ 0.82 (t, 3 H), 1.0–1.4 (m, 4 H), 1.83–1.99 (m, 2 H), 2.97 (dd, 2 H), 3.63 (dd, 2 H), 6.83–7.41 (m, 11 H).

EXAMPLE 30

6-[1,1'-Biphenyl]-4-yl-6-butyl-5,6-dihydro-4-hydroxy-3-[(phenylmethyl)thio]-2H-pyran-2-one (±)

The title compound was prepared as described in General Method 4 using (0.388 mmol) of 6-[1,1'-biphenyl]-4-yl-6-butyl-5,6-dihydro-4-hydroxy-2H-pyran-2-one, 5 mL of absolute EtOH, (0.407 mmol) of benzyl-p-toluenethiosulfonate in 3 mL of absolute EtOH and (0.426 mmol) of triethylamine in 2 mL of absolute EtOH. The reaction was stirred at room temperature overnight. The product was flash chromatographed ($CH_2Cl_2$/MeOH 99/1) to afford a solid (m.p. 45°–52° C.). $^1H$ NMR ($CDCl_3$) δ 0.85 (t, 3 H), 1.15–1.7 (m, 5 H), 1.9–2.1 (m, 2 H), 3.0 (ABq, 2 H), 3.5 (d, 1 H), 3.7 (d, 1 H), 6.8–6.9 (m, 2 H), 7.0–7.7 (m, 12 H).

EXAMPLE 31

5,6-Dihydro-4-hydroxy-6-phenyl-3-[(phenylmethyl)thio]-6-propyl-2H-pyran-2-one (±)

The title compound was prepared as described in General Method 4 using 1.08 mmol of 5,6-dihydro-4-hydroxy-6-phenyl-6-propyl-2H-pyran-2-one, 5 mL of absolute EtOH, 1.29 mmol of benzyl-p-toluenethiosulfonate in 10 mL of absolute EtOH and 1.51 mmol of triethylamine in 5 mL of absolute EtOH. The reaction was stirred at room temperature overnight. The product was flash chromatographed (hexane/ethyl acetate 75/25) to afford a viscous oil. $^1H$ NMR ($CDCl_3$) δ 0.83 (t, 3 H), 1.0–1.2 (m, 1 H),1.3–1.5 (m, 1 H),1.8–2.0(m, 2 H),2.97 (ABq, 2 H), 3.5 (d, 1 H), 3.7 (d, 1 H), 6.8–6.9 (m, 2 H),7.0–7.5 (m, 9 H).

EXAMPLE 32

5,6-Dihydro-4-hydroxy-6-phenyl-3-[(2-phenylethyl)thio]-6-propyl-2H-pyran-2-one (±)

The title compound was prepared as described in General Method 4 using 1.08 mmol of 5,6-dihydro-4-hydroxy-6-phenyl-6-propyl-2H-pyran-2-one, 5 mL of absolute EtOH, 1.29 mmol of 2-phenylethyl-p-toluenethiosulfonate in 10 mL of absolute EtOH and 1.51 mmol of triethylamine in 5 mL of absolute EtOH. The reaction was stirred at room temperature overnight. The product was flash chromatographed (hexane/ethyl acetate 60/40) to afford a viscous oil. $^1H$ NMR ($CDCl_3$) δ 0.85 (t, 3 H), 1.1–1.3 (m, 1 H),1.3–1.5 (m, 1 H), 1.8–2.0(m, 2 H),2.2–2.3 (m, 1 H), 2.3–2.5 (m, 1 H), 2.6–2.8 (m, 2 H), 3.1 (ABq, 2 H), 6.9 (d, 2 H), 7.1–7.5 (m, 9 H).

EXAMPLE 33

5,6-Dihydro-4-hydroxy-6-pentyl-6-phenyl-3-[(phenylmethyl)thio]-2H-pyran-2-one (±)

The title compound was prepared as described in General Method 4 using 0.96 mmol of 5,6-dihydro-6-pentyl-6-phenyl-2H-pyran-2-one, 5 mL of absolute EtOH, 1.05 mmol of benzyl-p-toluenethiosulfonate in 10 mL of absolute EtOH and 1.05 mmol of triethylamine in 5 mL of absolute EtOH. The reaction was stirred at room temperature overnight. The product was flash chromatographed (hexane/ethyl acetate 75/25) to afford a viscous oil. $^1H$ NMR ($CDCl_3$) δ 0.81(t, 3 H), 1.0–1.4 (m, 6 H), 1.8–2.0 (m, 2 H), 2.97 (ABq, 2 H), 3.5 (d, 1 H), 3.7 (d, 1 H), 6.8–6.9 (m, 2 H), 7.0–7.4 (m, 9 H).

EXAMPLE 34

5,6-Dihydro-4-hydroxy-6-pentyl-6-phenyl-3-[(2-phenylethyl)thio]-2H-pyran-2-one (±)

The title compound was prepared as described in General Method 4 using 0.96 mmol of 5,6-dihydro-6-pentyl-6-phenyl-2H-pyran-2-one, 5 mL of absolute EtOH, 1.05 mmol of 2-phenethyl-p-toluenethiosulfonate in 10 mL of absolute EtOH and 1.05 mmol of triethylamine in 5 mL of absolute EtOH. The reaction was stirred at room temperature overnight. The product was flash chromatographed (hexane/ethyl acetate 70/30) to afford a viscous oil. $^1H$ NMR ($CDCl_3$) δ 0.82 (t, 3 H), 1.0–1.4 (m, 6 H), 1.8–2.0(m, 2 H), 2.2–2.3 (m, 1 H), 2.3–2.5 (m, 1 H), 2.6–2.8 (m, 2 H) 3.13 (ABq, 2 H), 6.8–6.9 (m, 2 H), 7.1–7.5 (m, 9 H).

EXAMPLE 35

5,6-Dihydro-4-hydroxy-6-(3-methylbutyl)-6-phenyl-3-[(phenylmethyl)thio]-2H-pyran-2-one (±)

The title compound was prepared as described in General Method 4 using 0.96 mmol of 5,6-dihydro-6-(3-methylbutyl)-6-phenyl-2H-pyran-2-one, 5 mL of absolute EtOH, 1.05 mmol of benzyl-p-toluenethiosulfonate in 10 mL of absolute EtOH and 1.15 mmol of triethylamine in 5 mL of absolute EtOH. The reaction was stirred at room temperature overnight. The product was flash chromatographed (hexane/ethyl acetate 80/20) to afford a viscous oil.

¹H NMR (CDCl₃) δ 0.80 (d,d, 6 H), 0.9–1.1 (m, 1 H), 1.2–1.3 (m, 1 H), 1.3–1.5 (m, 1 H), 1.8–2.0 (m, 2 H), 2.97 (ABq, 2 H), 3.5 (d, 1 H), 3.7 (d, 1 H), 6.8–6.9 (m, 2 H), 7.0–7.4 (m, 9 H).

EXAMPLE 36

5,6-Dihydro-4-hydroxy-6-(3-methylbutyl)-6-phenyl-3-[(2-phenylethyl)thio]-2H-pyran-2-one (±)

The title compound was prepared as described in General Method 4 using 0.96 mmol of 5,6-dihydro-6-(3-methylbutyl)-6-phenyl-2H-pyran-2-one, 5 mL of absolute EtOH, 1.05 mmol of 2-phenylethyl-p-toluenethiosulfonate in 10 mL of absolute EtOH and 1.05 mmol of triethylamine in 5 mL of absolute EtOH. The reaction was stirred at room temperature overnight. The product was flash chromatographed (hexane/ethyl acetate 80/20) to afford a viscous oil. ¹H NMR (CDCl₃) δ 0.80(d,d, 6 H), 1.0–1.15 (m, 1 H), 1.2–1.3 (m, 1 H), 1.4–1.5 (m, 1 H), 1.9–2.0 (m, 2 H), 2.2–2.3 (m, 1 H), 2.3–2.5 (m, 1 H), 2.6–2.8 (m, 2 H), 3.15 (ABq, 2 H), 6.8–6.9 (m, 2 H), 7.1–7.5 (m, 9 H).

EXAMPLE 37

5,6-Dihydro-4-hydroxy-6,6-diphenyl-3-[(phenylmethyl)thio]-2H-pyran-2-one

The title compound was prepared as described in General Method 4 using 0.94 mmol of 5,6-dihydro-4-hydroxy-6,6-diphenyl-2H-pyran-2-one, 5 mL of absolute EtOH, 1.13 mmol of benzyl-p-toluenethiosulfonate in 10 mL of absolute EtOH and 1.31 mmol of triethylamine in 5 mL of absolute EtOH. The reaction was stirred at room temperature overnight. The product was flash chromatographed (CH₂Cl₂/MeOH 100/0–98/2) to afford a solid (m.p. 44°–47.5° C.). ¹H NMR (CDCl₃) δ 3.34 (s, 2 H), 3.63 (s, 2 H), 6.8–6.9 (m, 2 H), 7.1–7.5 (m, 14 H).

EXAMPLE 38

5,6-Dihydro-4-hydroxy-6,6-diphenyl-3-[(2-phenylethyl)thio]-2H-pyran-2-one

The title compound was prepared as described in General Method 4 using 0.94 mmol of 5,6-dihydro-4-hydroxy-6,6-diphenyl-2H-pyran-2-one, 5 mL of absolute EtOH, 1.13 mmol of 2-pheylnethyl-p-toluenethiosulfonate in 10 mL of absolute EtOH and 1.31 mmol of triethylamine in 5 mL of absolute EtOH. The reaction was stirred at room temperature overnight. The solid product was triturated from diethyl ether to afford a solid (m.p. 153°–154.5° C.). ¹H NMR (CDCl₃) δ 2.3 (t, 2 H), 2.6 (t, 2 H), 3.49 (s, 2 H), 6.8–6.9 (m, 2 H), 7.1–7.6 (m, 14 H).

EXAMPLE 39

5,6-Dihydro-4-hydroxy-6-phenyl-6-(2-phenylethyl)-3-[(phenylmethyl)thio]-2H-pyran-2-one (±)

The title compound was prepared as described in General Method 4 using 0.85 mmol of 5,6-dihydro-4-hydroxy-6-phenyl-6-(2-phenylethyl)-2H-pyran-2-one, 5 mL of absolute EtOH, 1.02 mmol of benzyl-p-toluenethiosulfonate in 10 mL of absolute EtOH and 1.19 mmol of triethylamine in 5 mL of absolute EtOH. The reaction was stirred at room temperature overnight. The product was flash chromatographed (hexane/ethyl acetate 80/20) to afford a viscous oil. ¹H NMR(CDCl₃) δ 2.1–2.4 (m, 3 H), 2.7–2.8 (m, 1 H), 3.0(ABq, 2 H), 3.5 (d, 1 H), 3.8 (d, 1 H), 6.8–6.9 (m, 2 H), 7.0–7.5 (m, 14 H).

EXAMPLE 40

5,6-Dihydro-4-hydroxy-6-phenyl-6-(2-phenylethyl)-3-[(2-phenylethyl)thio]-2H-pyran-2-one (±)

The title compound was prepared as described in General Method 4 using 0.85 mmol of 5,6-dihydro-4-hydroxy-6-phenyl-6-(2-phenylethyl)-2H-pyran-2-one, 5 mL of absolute EtOH, 1.02 mmol of 2-phenylethyl-p-toluenethiosulfonate in 10 mL of absolute EtOH and 1.19 mmol of triethylamine in 5 mL of absolute EtOH. The reaction was stirred at room temperature overnight. The solid product was triturated from ether to afford a solid (m.p. 56°–58° C.). ¹H NMR(CDCl₃) δ 2.2–2.5 (m, 5 H), 2.6–2.8 (m, 3 H), 3.2 (ABq, 2 H), 6.8–6.9 (m, 2 H), 7.0–7.5 (m, 14 H).

EXAMPLE 41

5,6-Dihydro-4-hydroxy-6-phenyl-3-[(2-phenylethyl)thio]-2(1H)-pyridinone (±)

The title compound was prepared as described in General Method 4 using 105 mg of 5,6-dihydro-4-hydroxy-6-phenyl-2(1H)-pyridinone, 175 mg of 2-phenylethyl-p-toluenethiosulfonate and 0.1 mL of triethylamine in 5 mL of absolute ethanol. The solution was stirred overnight at room temperature. Purification by flash chromatography using CH₂Cl₂/methanol (100/0 to 97/3) as eluent gave a viscous oil which was triturated with diethyl ether to afford a solid (m.p. 111°–113 ° C.). ¹H NMR (CDCl₃) δ 2.80–3.03 (m, 6 H), 4.70 (t, 1 H), 5.75 (s, 1 H), 7.16–7.40 (m, 11 H).

EXAMPLE 42

5,6-Dihydro-4-hydroxy-6-phenoxymethyl-6-phenyl-3-[(phenylmethyl)thio]-2H-pyran-2-one,(+/−)

The title compound was prepared as described in General Method 4 using 200 mg of 5,6-dihydro-4-hydroxy-6-phenoxymethyl-6-phenyl-2H-pyran-2-one, 210 mg of benzyl-p-toluenethiosulfonate and 0.125 mL of triethylamine in 5 mL of absolute ethanol. The solution was stirred overnight at room temperature. Purification by flash chromatography using CH₂Cl₂/methanol (100/0 to 95/5) as eluent gave a solid (m.p. 161°–163° C.) ¹H NMR (CDCl₃) δ 3.10 (d, 1 H), 3.52 (d, 1 H), 3.54 (d, 1 H), 3.75 (d, 1 H), 3.97 (d, 1 H), 4.23 (d, 1 H), 6.84–7.52 (m, 16 H).

EXAMPLE 43

6-[2-(Benzo[1,3]dioxol-5-yl)ethyl]-5,6-dihydro-4-hydroxy-6-phenyl-3-[(phenylmethyl)thio]-2H-pyran-2-one,(+/−)

The title compound was prepared as described in General Method 4 using 165 mg of 6-[2-(benzo[1,3]dioxol-5-yl)ethyl]-5,6-dihydro-4-hydroxy-6-phenyl-2H-pyran-2-one, 150 mg of benzyl-p-toluenethiosulfonate and 0.075 mL of triethylamine in 5 mL of absolute ethanol. The solution was stirred overnight at room temperature. Purification by flash chromatography using CH₂Cl₂/methanol (100/0 to 95/5) as eluent gave a solid (m.p. 45°–50° C.) ¹H NMR (CDCl₃) δ 2.08–2.30 (m, 3 H), 2.62–2.71 (m, 1 H), 2.98 (dd, 2 H), 3.53 (d, 1 H), 3.76 (d, 1 H), 5.89 (s, 2 H), 6.50–6.86 (m, 5 H), 7.06–7.26 (m, 4 H), 7.33–7.44 (m, 5 H).

EXAMPLE 44

6-[2-(3,4-Dichlorophenyl)ethyl]-5,6-dihydro-4-hydroxy-6-phenyl-3-[(phenylmethyl)thio]-2H-pyran-2-one,(+/−)

The title compound was prepared as described in General Method 4 using 365 mg of 6-[2-(3,4-dichlorophenyl)ethyl]

-5,6-dihydro-4-hydroxy-6-phenyl-2H-pyran-2-one, 310 mg of benzyl-p-toluenethiosulfonate and 0.15 mL of triethylamine in 5 mL of absolute ethanol. The solution was stirred overnight at room temperature. Purification by flash chromatography using $CH_2Cl_2$/methanol (100/0 to 95/5) as eluent gave a solid (m.p. 43°–50° C.) $^1H$ NMR ($CDCl_3$) δ 2.07–2.16 (m, 1 H), 2.21–2.28 (m, 2 H), 2.71–2.77 (m, 1 H), 2.99 (dd, 2 H), 3.54 (d, 1 H), 3.78 (d, 1 H), 6.84–6.91 (m, 3 H), 7.10–7.45 (m, 11 H).

EXAMPLE 45

6-[2-(4-Fluorophenyl)ethyl]-5,6-dihydro-4-hydroxy-6-phenyl-3-[(phenylmethyl)thio]-2H-pyran-2-one,(+/−)

The title compound was prepared as described in General Method 4 using 312 mg of 6 [2-(4-fluorophenyl)ethyl]-5,6-dihydro-4-hydroxy-6-phenyl-2H-pyran-2-one, 310 mg of benzyl-p-toluenethiosulfonate and 0.15 mL of triethylamine in 5 mL of absolute ethanol. The solution was stirred overnight at room temperature. Purification by flash chromatography using $CH_2Cl_2$/methanol (100/0 to 95/5) as eluent gave a solid (m.p. 86°–90° C.) $^1H$ NMR ($CDCl_3$) δ 2.08–2.35 (m, 3 H), 2.70–2.77 (m, 1 H), 2.99 (dd, 2 H), 3.54 (d, 1 H), 3.77 (d, 1 H), 6.85–7.44 (m, 15 H).

EXAMPLE 46

5,6-Dihydro-6-hexyl-4-hydroxy-6-phenyl-3-[(phenylmethyl)thio]-2H-pyran-2-one (±)

The title compound was prepared as described in General Method 4 using 0.91 mmol of 5,6-dihydro-6-hexyl-4-hydroxy-6-phenyl-2H-pyran-2-one (±), 5 mL of absolute EtOH, 1.1 mmol of benzyl-p-toluenethiosulfonate in 5 mL of absolute EtOH and 1.27 mmol of triethylamine in 5 mL of absolute EtOH. The reaction was stirred at room temperature overnight. The product was flash chromatographed using $CH_2Cl_2$/MeOH (99.5/0.5) to afford a viscous gum. $^1H$ NMR ($CDCl_3$) δ 0.81 (t, 3 H), 1.0–1.4 (m, 8 H), 1.8–2.0 (m, 2 H), 2.97 (ABq, 2 H), 3.5 (d, 1 H), 3.7 (d, 1 H), 6.8–6.9 (m, 2 H), 7.0–7.4 (m, 9 H).

EXAMPLE 47

5,6-Dihydro-6-hexyl-4-hydroxy-6-phenyl-3-[(2-phenylethyl)thio]-2H-pyran-2-one (±)

The title compound was prepared as described in General Method 4 using 0.91 mmol of 5,6-dihydro-6-hexyl-4-hydroxy-6-phenyl-2H-pyran-2-one (±), 5 mL of absolute EtOH, 1.09 mmol of phenethyl-p-toluenethiosulfonate in 5 mL of absolute EtOH and 1.27 mmol of triethylamine in 5 mL of absolute EtOH. The reaction was stirred at room temperature overnight. The product was flash chromatographed using $CH_2Cl_2$/MeOH (99.75/0.25–99/1) to afford a viscous gum. $^1H$ NMR ($CDCl_3$) δ 0.84 (t, 3 H), 1.0–1.4 (m, 8 H), 1.8–2.0 (m, 2 H), 2.2–2.3 (m, 1 H), 2.3–2.5 (m, 1 H), 2.6–2.8 (m, 2 H) 3.13 (ABq, 2 H), 6.9 (dd, 2 H), 7.1–7.5 (m, 8 H).

EXAMPLE 48

5,6-Dihydro-4-hydroxy-6-(4-methylpentyl)-6-phenyl-3-[(phenylmethyl)thio]-2H-pyran-2-one (±)

The title compound was prepared as described in General Method 4 using 1 mmol of 5,6-dihydro-4-hydroxy-6-(4-methylpentyl)-6-phenyl-2H-pyran-2-one (±), 5 mL of absolute EtOH, 1.2 mmol of benzyl-p-toluenethiosulfonate in 5 mL of absolute EtOH and 4 mmol of $NaHCO_3$ in 5 mL of absolute EtOH.

The reaction was heated to 50° C. for 1.5 hours then stirred at room temperature overnight. The product was flash chromatographed using $CH_2Cl_2$/MeOH (100/0–99/1) to afford a viscous gum. $^1H$ NMR ($CDCl_3$) δ 0.78 (d, 6 H), 1.0–1.5 (m, 5 H), 1.8–2.0 (m, 2 H), 2.97 (ABq, 2 H), 3.5 (d, 1 H), 3.7 (d, 1 H), 6.8–6.9 (m, 2 H), 7.0–7.4 (m, 9 H).

EXAMPLE 49

5,6-Dihydro-4-hydroxy-6-(4-methylpentyl)-6-phenyl-3-[(2-phenylethyl)thio]-2H-pyran-2-one (±)

The title compound was prepared as described in General Method 4 using 1 mmol of 5,6-dihydro-4-hydroxy-6-(4-methylpentyl)-6-phenyl-2H-pyran-2- one (±), 5 mL of absolute EtOH, 1.2 mmol of phenethyl-p-toluenethiosulfonate in 5 mL of absolute EtOH and 1.4 mmol of triethylamine in 5 mL of absolute EtOH. The reaction was stirred for 2 hours at 50° C. The product was flash chromatographed using hexane/ethyl acetate (80/20) to afford a viscous gum. $^1H$ NMR ($CDCl_3$) δ 0.79 (d, 6 H), 1.0–1.5 (m, 5 H), 1.8–2.0 (m, 2 H), 2.2–2.3 (m, 1 H), 2.3–2.5 (m, 1 H), 2.6–2.8 (m, 2 H) 3.14 (ABq, 2 H), 6.9 (.d, 2 H), 7.1–7.5 (m, 8 H).

EXAMPLE 50

6-Cyclopentylmethyl-5,6-dihydro-4-hydroxy-6-phenyl-3-[(phenylmethyl)thio]-2H-pyran-2-one (±)

The title compound was prepared as described in General Method 4 using 1 mmol of 6-cyclopentylmethyl-5,6-dihydro-4-hydroxy-6-phenyl-2H-pyran-2 -one (±), 5 mL of absolute EtOH, 1.2 mmol of benzyl-p-toluenethiosulfonate in 5 mL of absolute EtOH and 4 mmol of $NaHCO_3$ in 5 mL of absolute EtOH. The reaction was heated to 120° C. for 15 minutes. The product was flash chromatographed using hexane/ethyl acetate (75/25) and then $CH_2Cl_{-2}$/MeOH (99.5/0.5) to afford a viscous gum. $^1H$ NMR ($CDCl_3$) δ 0.8–1.0 (m, 1 H), 1.0–1.2 (m, 1 H), 1.3–1.6 (m, 5 35 H), 1.6–1.8 (m, 2 H), 1.97 (dd, 1 H), 2.07 (dd, 1 H), 2.97 (ABq, 2 H), 3.5 (d, 1 H), 3.7 (d, 1 H), 6.8–6.9 (m, 2 H), 7.0–7.4 (m, 9 H).

EXAMPLE 51

6-Cyclopentylmethyl-5,6-dihydro-4-hydroxy-6-phenyl-3-[(2-phenylethyl)thio]-2H-pyran-2-one (±)

The title compound was prepared as described in General Method 4 using 1 mmol of 6-cyclopentylmethyl-5,6-dihydro-4-hydroxy-6-phenyl-2H-pyran -2-one (±), 5 mL of absolute EtOH, 1.2 mmol of phenethyl-p-toluenethiosulfonate in 5 mL of absolute EtOH and 1.4 mmol of triethylamine in 5 mL of absolute EtOH. The reaction was stirred at room temperature for 2 days. The product was flash chromatographed using hexane/ethyl acetate (75/25–60/40) to afford a viscous gum. $^1H$ NMR (DMSO-$d_6$) δ 0.8–1.0 (m, 1 H), 1.0–1.1 (m, 1 H), 1.2–1.8 (m, 7 H), 1.9–2.1 (m, 2 H), 2.3 (t, 2 H), 2.5–2.6 (m, 2 H) 3.25 (s, 2 H), 6.95 (d, 2 H), 7.1–7.4 (m, 8 H).

EXAMPLE 52

3,4-Dihydro-4'-hydroxy-5'-[(phenylmethyl)thio]-spiro[naphthalene-1(2H),2'-[2H]pyran]-6'(3'H)-one (±)

The title compound was prepared as described in General Method 4 using 1.1 mmol of 3,4-dihydro-4'-hydroxy-spiro

[naphthalene-1(2H),2'-[2H]pyran]-6'(3'H)-one (±), 5 mL of absolute EtOH, 1.3 mmol of benzyl-p-toluenethiosulfonate in 5 mL of absolute EtOH and 1.5 mmol of triethylamine in 5 mL of absolute EtOH. The reaction was stirred overnight at room temperature. The product was flash chromatographed using hexane/ethyl acetate (90/10–60/40) and then triturated from ether to afford a solid (m.p. 143°–145° C.). $^1$H NMR (CDCl$_3$) δ 1.5–1.8 (m, 2 H), 1.8–2.1 (m, 2 H), 2.6 (d, 1 H), 2.7–2.9 (m, 2 H), 3.0 (dd, 1 H), 3.9 (ABq, 2 H), 7.0–7.2 (m, 1 H), 7.2–7.4 (m, 7 H), 7.4–7.5 (m, 1 H).

EXAMPLE 53

3,4-Dihydro-4'-hydroxy-5'-[(2-phenylethyl)thio]-spiro[naphthalene-1(2H),2'-[2H]pyran]-6'(3'H)-one (±)

The title compound was prepared as described in General Method 4 using 1.1 mmol of 3,4-dihydro-4'-hydroxy-spiro[naphthalene-1(2 H),2'-[2H]pyran]-6'(3'H)-one (±), 5 mL of absolute EtOH, 1.3 mmol of phenethyl-p-toluenethiosulfonate in 5 mL of absolute EtOH and 1.5 mmol of triethylamine in 5 mL of absolute EtOH. The reaction was stirred at room temperature overnight. The product was flash chromatographed using CH$_2$Cl$_2$/MeOH (100/0–98/2) to afford a solid which was recrystallized from CH$_2$Cl$_2$/diethyl ether to afford a solid (m.p. 125°–126.5° C.). $^1$H NMR (CDCl$_3$) δ 1.6–1.9 (m, 1 H), 1.9–2.1 (m, 1 H), 2.1–2.3 (m, 2 H), 2.7–3.3 (m, 8 H), 7.1–7.4 (m, 7 H), 7.5–7.7 (m, 2 H).

EXAMPLE 54

3-(3,6-Dihydro-4-hydroxy-6-oxo-2-phenyl-S-[(2-phenylethyl)thio]-2H-pyran-2-yl)propanoic acid (±)

The title compound was prepared as described in General Method 4 using 0.95 mmol of 3-(3,6-dihydro-4-hydroxy-6-oxo-2-phenyl-2H-pyran-2-yl)-propanoic acid (±), 5 mL of absolute EtOH, 1.1 mmol of phenethyl-p-toluenethiosulfonate in 5 mL of absolute EtOH and 2.3 mmol of triethylamine in 5 mL of absolute EtOH. The reaction was refluxed for 2 hours. The product was flash chromatographed using CH$_2$Cl$_2$/MeOH/MeCO$_2$H (95/5/0.05) to afford a solid which was recrystallized from ethyl acetate (m.p. 150.5°–152° C.). $^1$H NMR (CDCl$_3$) δ 2.1–2.9 (m, 8 H), 3.15 (ABq, 2 H), 6.9 (d, 2 H), 7.1–7.4 (m, 8 H).

EXAMPLE 55

4-(3,6-Dihydro-4-hydroxy-6-oxo-2-phenyl-5-[(2-phenylethyl)thio]-2H-pyran-2-yl)butyric acid (±)

The title compound was prepared as described in General Method 4 using 1.8 mmol of 4-(3,6-dihydro-4-hydroxy-6-oxo-2-phenyl-2H-pyran-2-yl)-butyric acid (±), 5 mL of absolute EtOH, 2.1 mmol of phenethyl-p-toluenethiosulfonate in 5 mL of absolute EtOH and 4.3 mmol of triethylamine in 5 mL of absolute EtOH. The reaction was refluxed for 3 hours. The product was flash chromatographed using CH$_2$Cl$_2$/MeOH/MeCO$_2$H (95/5/0.05) to afford a amorphous solid. $^1$H NMR (CDCl$_3$) δ 1.4–1.6 (m, 1 H), 1.6–1.8 (m, 1 H), 1.9–2.1 (m, 2 H), 2.2–2.4 (m, 3 H), 2.4–2.5 (m, 1 H), 2.6–2.8 (m, 2 H), 3.15 (ABq, 2 H), 6.9 (d, 2 H), 7.1–7.5 (m, 8 H).

EXAMPLE 56

5-(3,6-Dihydro-4-hydroxy-6-oxo-2-phenyl-5-[(2-phenylethyl)thio]-2H-pyran-2-yl)pentanoic acid (±)

The title compound was prepared as described in General Method 4 using 1.8 mmol of 5-(3,6-dihydro-4-hydroxy-6-oxo-2-phenyl-2H-pyran-2-yl)-pentanoic acid (±), 10 mL of absolute EtOH, 2.2 mmol of phenethyl-p-toluenethiosulfonate in 10 mL of absolute EtOH and 4.3 mmol of triethylamine in 10 mL of absolute EtOH. The reaction was refluxed for 3 hours. The product was flash chromatographed using CH$_2$Cl$_2$/MeOH/MeCO$_2$H (99/1/0.05) to afford a solid (m.p. 113°–119.5° C.). $^1$H NMR (CDCl$_3$) δ 0.8–1.1 (m, 1 H), 1.1–1.3 (m, 1 H), 1.3–1.5 (m, 2 H), 1.8–2.0 (m, 2 H), 2.1 (t, 2 H), 2.2 (t, 2 H), 2.5–2.8 (m, 2 H), 3.2 (ABq, 2 H), 6.9 (d, 2 H), 7.1–7.4 (m, 8 H), 11.5 (bs, 1 H), 11.9 (bs, 1 H).

EXAMPLE 57

5,6-Dihydro-4-hydroxy-6-phenyl-3-[(2-phenylethyl)thio]-6-pyridin-4-yl-2H-pyran-2-one (±)

The title compound was prepared as described in General Method 4 using 0.47 mmol of 5,6-dihydro-4-hydroxy-6-phenyl-6-pyridin-4-yl-2H-pyran-2-one (±), 0.56 mmol of phenethyl-p-toluenethiosulfonate in 5 mL of absolute EtOH, 2 mmol of NaHCO$_3$, and 0.65 mmol of triethylamine in 5 mL of absolute EtOH. The reaction was stirred overnight at room temperature. The solid product was triturated from ethyl acetate (m.p. 203°–205° C.). $^1$H NMR (DMSO-d$_6$) δ 2.1 (t, 2 H), 2.5 (t, 2 H), 3.7 (ABq, 2 H), 6.9 (d, 2 H), 7.1–7.6 (m, 10 H), 8.6 (d, 2 H).

EXAMPLE 58

5,6-Dihydro-4-hydroxy-6-[(methylphenylamino)methyl]-6-phenyl-3-[(2-phenylethyl)thio]-2H-pyran-2-one (±)

The title compound was prepared as described in General Method 4 using 0.55 mmol of 5,6-dihydro-4-hydroxy-6-[(methylphenylamino)methyl]-6-phenyl-2H-pyran-2-one (±), 0.61 mmol of phenethyl-p-toluenethiosulfonate in 5 mL of absolute EtOH, 2.2 mmol of NaHCO$_3$, and 0.61 mmol of triethylamine in 5 mL of absolute EtOH. The reaction was stirred overnight at room temperature then 2 hours at 50° C. The solid product was flash chromatographed using CH$_2$Cl$_2$/MeOH (99/1) to afford a solid (m.p. 48°–57° C.). $^1$H NMR (CDCl$_3$) δ 2.2–2.3 (m, 1 H), 2.3–2.5 (m, 1 H), 2.6–2.8 (m, 2 H), 3.08 (s, 3 H), 3.15 (d, 1 H), 3.35 (d, 1 H), 3.7 (ABq, 2 H), 6.7–6.9 (m, 3 H), 7.1–7.6 15 (m, 12 H).

EXAMPLE 59

4-(3,6-Dihydro-4-hydroxy-6-oxo-2-phenyl-5-[(phenylmethyl)thio]-2H-pyran-2-yl)butyramide (±)

To a 50 mL reaction flask was added 0.75 mmol of 4-(3,6-dihydro-4-hydroxy-6-oxo-2-phenyl-2H-pyran-2-yl)propanoic acid (±), 1.5 mmol of 4-methylmorpholine, and 7.5 mL of CH$_2$Cl$_2$. The reaction was cooled to 0° C. and 1.5 mmol of methyl chloroformate in 3.5 mL of CH$_2$Cl$_2$ was added. The reaction was stirrred at 0° C. for 2 hours. Ammonia was bubbled into the vessel for 10–15 minutes and the reaction allowed to stir for 30 min at 0° C. then 1.5 hours at room temperature. The reaction was poured into ethyl acetate and 1N HCl, the aqueous layer extracted with 2×ethyl acetate, dried over MgSO$_4$, and concentrated. The crude reaction mixture was flash chromatographed using CH$_2$Cl$_2$/MeOH/MeCO$_2$H (98/2/0.05) to afford 4-(3,6-dihydro-4-hydroxy-6-oxo-2-phenyl-2H-pyran-2-yl)butyramide (±) as a solid (m.p. 51°–54° C.). $^1$H NMR (DMSO-d$_6$) δ 1.0–1.2 (m, 1 H), 1.3–1.6 (m, 1 H), 1.8–2.0 (m, 4 H), 2.9 (ABq, 2 H), 4.8 (s, 1 H), 6.6 (s, 1 H), 7.2 (s, 1 H), 7.2-7.5 (m, 5 H), 11.4 (bs, 1 H).

The title compound was prepared as described in General Method 4 using 0.42 mmol of 4-(3,6-dihydro-4-hydroxy-6-oxo-2-phenyl-2H-pyran-2-yl)-butyramide (±) 5 mL of absolute EtOH, 0.58 mmol of benzyl-p-toluenethiosulfonate in 5 mL of absolute EtOH, 1.67 mmol NaHCO$_3$, and 0.42 mmol of triethylamine in 5 mL of absolute EtOH. The reaction was stirred at room temperature overnight. The product was flash chromatographed using CH$_2$Cl$_2$/MeOH (90/10) to afford the desired compound as a solid (m.p. 47.5°–53° C.). $^1$H NMR (DMSO-d$_6$) δ 1.0–1.3 (m, 1 H), 1.3–1.6 (m, 1 H), 1.7–2.1 (m, 4 H), 3.1 (s, 2 H), 3.5 (ABq, 2 H) 6.7 (s, 1 H) 7.0–7.5 (m, 11 H), 11.4 (s, 1 H).

EXAMPLE 60

5-(3,6-Dihydro-4-hydroxy-6-oxo-2-phenyl-5-[(2-phenylethyl)thio]-2H-pyran-2-yl)pentanoic acid amide (±)

To a 50 mL reaction flask was added 1.2 mmol of 5-(3,6-dihydro-4-hydroxy-6-oxo-2-phenyl-2H-pyran-2-yl) pentanoic acid (±), 2.4 mmol of 4-methylmorpholine, and 10 mL of CH$_2$Cl$_2$. The reaction was cooled to 0° C. and 2.4 mmol of methyl chloroformate in 3 mL of CH$_2$Cl$_2$ was added. The reaction was stirrred at 0° C. for 2 hours. Ammonia was bubbled into the vessel for 10–15 minutes and the reaction allowed to stir for 30 minutes at 0° C. The reaction was poured into ethyl acetate and 1N HCl, the aqueous layer extracted with ethyl acetate, dried over MgSO$_4$, and concentrated. The crude solid was triturated using CH$_2$Cl$_2$ to afford 5-(3,6-dihydro-4-hydroxy-6-oxo-2-phenyl-2H-pyran-2-yl)pentanoic acid amide (±) as a solid (m.p. 173°–174° C.). $^1$H NMR (DMSO-d$_6$) δ 0.8–1.0 (m, 1 H), 1.1–1.3 (m, 1 H), 1.3–1.5 (m, 2 H), 1.8–2.0 (m, 4 H), 2.9 (ABq, 2 H), 4.8 (s, 1 H), 6.6 (s, 1 H), 7.2 (s, 1 H), 7.2–7.5 (m, 5 H), 11.4 (s, 1 H).

The title compound was prepared as described in General Method 4 using 0.60 mmol of 5-(3,6-dihydro-4-hydroxy-6-oxo-2-phenyl-2H-pyran-2-yl)pentanoic acid amide (±) 5 mL of absolute EtOH, 0.85 mmol of phenethyl-p-toluenethiosulfonate, 2.4 mmol NaHCO$_3$, and 0.60 mmol of triethylamine in 5 mL of absolute EtOH. The reaction was stirred at room temperature overnight. The product was flash chromatographed using CH$_2$Cl$_2$/MeOH (90/10) then triturated from ether to afford a solid (softened 100°–105° C., melted completely at 120° C.). $^1$H NMR (DMSO-d$_6$) δ 0.9–1.1 (m, 1 H), 1.1–1.3 (m, 1 H), 1.3–1.5 (m, 2 H), 1.8–2.0 (m, 4 H), 2.2 (t, 2 H), 2.5–2.6 (m 2 H), 3.2 (s, 2 H), 6.6 (s, 1 H), 6.9 (d, 2 H), 7.1–7.6 (m, 9 H), 11.5 (bs, 1 H).

EXAMPLE 61

N-Benzyl-4-(3,6-dihydro-4-hydroxy-6-oxo-2-phenyl-5-[(phenylmethyl)thio]-2H-pyran-2-yl) butyramide (±)

To a 50 mL reaction flask was added 0.75 mmol of 4-(3,6-dihydro-4-hydroxy-6-oxo-2-phenyl-2H-pyran-2-yl) propanoic acid (±), 1.5 mmol of 4-methylmorpholine, and 7.5 mL of CH$_2$Cl$_2$. The reaction was cooled to 0° C. and 1.5 mmol of methyl chloroformate in 3.5 mL of CH$_2$Cl$_2$ was added. The reaction was stirrred at 0° C. for 2 hours. Benzyl amine (1.6 mmol) in CH$_2$Cl$_2$ (5 mL) was added and the reaction allowed to stir for 30 min at 0° C. then 1.5 hours at room temperature. The reaction was poured into ethyl acetate and 1N HCl, the aqueous layer extracted with 2×ethyl acetate, dried over MgSO$_4$, and concentrated. The crude reaction mixture was flash chromatographed using CH$_2$Cl$_2$/MeOH (99/1).

The resulting carbamate (200 mg) was hydrolized by treatment with 0.1N HCl (20 mL) in p-dioxane (4 mL) for 1 hour at room temperature to afford N-benzyl-4-(3,6-dihydro-4-hydroxy-6-oxo-2-phenyl-2H-pyran-2-yl)-butyramide (+/−).

The title compound was prepared as described in General Method 4 using 0.33 mmol of N-benzyl-4-(3,6-dihydro-4-hydroxy-6-oxo-2-phenyl-2H-pyran-2-yl)butyramide (±), 5 mL of absolute EtOH, 0.47 mmol of benzyl-p-toluenethiosulfonate in 5 mL of absolute EtOH, 1.33 mmol NaHCO$_3$, and 0.33 mmol of triethylamine in 5 mL of absolute EtOH. The reaction was stirred at room temperature overnight. The product was flash chromatographed using CH$_2$Cl$_2$/MeOH (95/5) to afford the desired compound as a solid (m.p. 48°–52° C.). $^1$H NMR (DMSO-d$_6$)δ 1.1–1.3 (m, 1 H), 1.4–1.6 (m, 1 H), 1.8–1.9 (m, 2 H), 2.0–2.2 (m, 2 H), 3.1 (s, 2 H), 3.6 (ABq, 2 H), 4.2 (d, 2 H), 7.0 (m, 2 H), 7.1–7.5 (m, 13 H), 8.3 (t, 1 H), 11.4 (bs, 1 H).

EXAMPLE 62

5-(3,6-Dihydro-4-hydroxy-6-Oxo-2-phenyl-5-[(2-phenylethyl)thio]-2H-pyran-2-yl)pentanoic acid benzylamide (±)

To a 50 mL reaction flask was added 0.83 mmol of 5-(3,6-dihydro-4-hydroxy-6-oxo-2-phenyl-2H-pyran-2-yl) pentanoic acid (±), 1.65 mmol of 4-methylmorpholine, and 10 mL of CH$_2$Cl$_2$. The reaction was cooled to 0° C. and 1.65 mmol of methyl chloroformate in 5 mL of CH$_2$Cl$_2$ was added. The reaction was stirrred at 0° C. for 2 hours. Benzyl amine (1.7 mmol) in CH$_2$Cl$_2$ (5 mL) was added and the reaction allowed to stir for 2 hours at room temperature. The reaction was poured into ethyl acetate and 1N HCl, the aqueous layer extracted with 2×ethyl acetate, dried over MgSO$_4$, and concentrated. The crude reaction mixture was carried on without purification.

The resulting carbamate (200 mg) was hydrolized by treatment with 0.1N HCl (20 mL) in p-dioxane (4 mL) for 8 hours at room temperature to afford 5-(3,6-dihydro-4-hydroxy-6-oxo-2-phenyl-2H-pyran-2-yl)-pentanoic acid benzylamide (±). $^1$NMR (DMSO-d$_6$) δ 0.8–1.0 (m, 1 H), 1.1–1.3 (m, 1 H), 1.3–1.5 (m, 2 H), 1.8–2.0 (m, 2 H), 2.0–2.2 (m, 2 H), 2.9 (ABq, 2 H), 4.2 (ABq, 2 H), 4.85 (s, 1 H), 7.1–7.5 (m, 10 H), 8.2 (bt, 1 H), 11.4 (s, 1 H).

The title compound was prepared as described in General Method 4 using 0.58 mmol of N-benzyl-5-(3,6-dihydro-4-hydroxy-6-oxo-2-phenyl-2H-pyran-2-yl)-pentanoic acid amide (±), 5 mL of absolute EtOH, 0.82 mmol of benzyl-p-toluenethiosulfonate, 2.34 mmol NaHCO$_3$, and 0.82 mmol of triethylamine in 5 mL of absolute EtOH. The reaction was stirred at room temperature overnight. The product was flash chromatographed using CH$_2$Cl$_2$/MeOH (99/1) to afford the desired compound as a solid (m.p. 47°–49° C.). $^1$H NMR (CDCl$_3$) δ 1.0–1.2 (m, 1 H), 1.3–1.5 (m, 1 H), 1.5–1.7 (m, 2 H), 1.8–2.0 (m, 2 H), 2.0–2.2 (m, 2 H), 2.9 (ABq, 2 H), 3.5 (d, 1 H), 3.7 (d, 1 H), 4.4 (m, 2 H), 5.7 (bt, 1 H), 6.8–6.9 (m, 2 H), 7.0–7.5 (m, 13 H).

EXAMPLE 63

N-Benzyl-4-(3,6-dihydro-4-hydroxy-6-oxo-2-phenyl-5-[(phenylmethyl)thio]-2H-pyran-2-yl)-N-methylbutyramide (±)

The title compound was prepared as described in General Method 4 using 0.66 mmol of N-benzyl-4-(3,6-dihydro-4-hydroxy-6-oxo-2-phenyl-2H-pyran-2-yl)-N- methylbutyramide (±), 0.92 mmol of benzyl-p-toluenethiosulfonate in 5 mL of absolute EtOH, 2.63 mmol of NaHCO$_3$, and 0.92 mmol of triethylamine in 5 mL of absolute EtOH. The reaction was heated for 2 hours at 50° C. The solid product was flash chromatographed using CH$_2$Cl$_2$/MeOH (99/1–98/2) to afford a solid (m.p. 47°–49° C.). $^1$H NMR (CDCl$_3$) δ 1.5–1.8 (m, 2 H), 1.9–2.1 (m, 2 H), 2.3 (ABq, 2 H), 2.84/2.91 (s/s 3 H), 2.98–3.02 (m, 2 H), 3.5 (dd, 1 H), 3.7 (dd, 1 H), 4.46/4.55 (s/s, 2 H), 6.8–6.9 (m, 2 H), 7.0–7.5 (m, 13 H).

GENERAL METHOD 5

The desired compounds were prepared by adding the appropriate acid chloride (1.05 equiv.) to a solution of the 5,6-dihydro-2H-pyran-2-one (1.0 equiv.), triethylamine (1.05 equiv.), and THF at 5° C. The suspension was stirred overnight at room temperature and then diluted with ethyl acetate and water. The organic phase was washed with ice-cold 1N HCl and brine, dried over MgSO$_4$, and concentrated. The residue was dissolved in toluene, treated with catalytic DMAP, and heated at 80°–85° C. for 4 to 8 hours. The solution was cooled to room temperature and diluted with water. The organic phase was washed with ice-cold 1N HCl and brine, dried (MgSO$_4$), and concentrated. The product was chromatographed on silica gel, eluting with 5:1 hexane:ethyl acetate, to give the 3-acylated intermediate. This material was dissolved in glacial acetic acid, treated with sodium cyanoborohydride (2 equiv), and stirred at room temperature for two hours. The reaction mixture was diluted with water, acidified with conc. HCl, and extracted with ethyl acetate. The extract was washed with brine, dried (MgSO$_4$), and concentrated to afford the desired compound.

EXAMPLE 64

5,6-Dihydro-4-hydroxy-6,6-diphenyl-3-(2-phenylethyl)-2H-pyran-2-one

The title compound was prepared as described in General Method 5 using 2.0 mmol of 5,6-dihydro-4-hydroxy-6,6-diphenyl-2H-pyran-2-one, 2.1 mmol of phenylacetyl chloride, 2.1 mmol of triethylamine, and 10 mL of THF, followed by 10 mL of toluene and catalytic DMAP. Chromatography of the residue afforded 1.5 mmol of the intermediate 3-acyl compound. Reduction of this acyl derivative was accomplished with 3 mmol of sodium cyanoborohydride. The product was triturated from ether (m.p. 158°–159° C.). $^1$H NMR (DMSO-d$_6$) 2.31 (m, 4 H), 3.37 (m, 2 H), 6.93 (d, 1 H), 7.07–7.17 (m, 3 H), 7.24–7.28 (m, 2 H), 7.35 (m, 8 H).

Alternatively, the title compound could be prepared as follows. A suspension of 0.25 g (6.2 mmol) of sodium hydride in 5 mL of dry THF was cooled to 0° C. under nitrogen and treated with a solution of 1.40 g (6.0 mmol) of ethyl 2-(2-phenylethyl)acetoacetate in THF (2 mL). The solution was stirred at 0° C. for ten minutes, treated with 4.3 mL of 1.4M n-butyllithium, and stirred for another fifteen minutes. A solution of 0.55 g (3.0 mmol) of benzophenone in THF (3 mL) was added all at once, and the reaction mixture was stirred at room temperature for two hours. Water (75 mL) was added, and the mixture was stirred overnight at room temperature. The solution was washed with ether. The aqueous layer was acidified to pH 2 with 6N HCl and extracted with ethyl acetate; the extract was washed with brine, dried over magnesium sulfate, and concentrated. The residue was triturated with ether : hexane 1:1, and the solids were filtered and dried to give the title compound.

EXAMPLE 65

5,6-Dihydro-4-hydroxy-6-(3-methylbutyl)-6-phenyl-3-(2-phenylethyl)-2H-pyran-2-one, (+/−)

The title compound was prepared as described in General Method 5 using 2.0 mmol of 5,6-dihydro-4-hydroxy-6-(3-5 methylbutyl)-6-phenyl-2H-pyran-2-one, 2.1 mmol of phenylacetyl chloride, 2.1 mmol of triethylamine, and 10 mL of THF, followed by 10 mL of toluene and catalytic DMAP. Chromatography of the residue afforded 1.0 mmol of the intermediate acyl compound. Reduction of this intermediate was effected with 2 mmol of sodium cyanoborohydride. The product was obtained as a solid (m.p. 125°–126° C.). $^1$H NMR (DMSO-d$_6$) 6 0.76 (m, 7 H), 1.12 (m, 1 H), 1.38 (m, 1 H), 1.87 (m, 2 H), 2.27–2.46 (m, 4 H), 2.97 (q, 2 H), 6.98–7.38 (m, 10 H).

EXAMPLE 66

5,6-Dihydro-4-hydroxy-6,6-diphenyl-3-(3-phenylpropyl)-2H-pyran-2-one

The title compound was prepared as described in General Method 5 using 2.5 mmol of 5,6-dihydro-4-hydroxy-6,6-diphenyl-2H-pyran-2-one, 2.7 mmol of phenylacetyl chloride, 2.8 mmol of triethylamine, and 20 mL of THF, followed by 20 mL of toluene and catalytic DMAP. Chromatography of the residue afforded 1.0 mmol of the intermediate 3-acyl compound. Reduction of this acyl derivative was accomplished with 3 mmol of sodium cyanoborohydride. The product was triturated from ether to give the title compound (m.p. 61°–63° C.). $^1$H NMR (DMSO-d$_6$) δ 1.35 (m, 2 H), 2.05 (t, 2 H), 2.14 (t, 2 H), 3.42 (bs, 2 H), 6.92 (m, 2 H), 7.17–7.40 (m, 13 H).

EXAMPLE 67

5,6-Dihydro-4-hydroxy-6-phenyl-3,6-bis(2-phenylethyl)-2H-pyran-2-one, (+/−)

The title compound was prepared as described in General Method 5 using 3.0 mmol of 5,6-dihydro-4-hydroxy-6-phenyl-6-(2-phenylethyl)-2H-pyran-2-one, 3.2 mmol of hydrocinnamoyl chloride, 3.2 mmol of triethylamine, and 30 mL of THF, followed by 30 mL of toluene and catalytic DMAP. Chromatography of the residue afforded 1.5 mmol of the intermediate 3-acyl compound. Reduction of this acyl derivative was accomplished with 3 mmol of sodium cyanoborohydride. The product was triturated from ether:hexane (1:5) to give the title compound (m.p. 68°–70° C.). $^1$H NMR (DMSO-d$_6$) 2.20 (m, 2 H), 2.35 (m, 2 H), 2.42–2.59 (m, 4 H plus DMSO), 3.06 (q, 2 H), 7.00 (dd, 2 H), 7.07–7.43 (m, 13 H).

General Method 6

The desired compounds were prepared by adding piperidine (1.05 equiv) to a cold (ice bath) solution of the 3-bromo-5,6-dihydro-4-hydroxy-2H-pyran-2-ones (1.0 mmol, prepared in General Method 3), the requisite thiol (1.05 mmol), and dichloromethane (20 mL). The mixture was stirred at room temperature for 8 to 48 hours. Water was added, and the organic phase was separated, dried over MgSO$_4$, and concentrated.

EXAMPLE 68

4-Hydroxy-3-(2-isopropylphenylthio)-5,6-dihydro-6,6-diphenyl-2H-pyran-2-one

The title compound was prepared as described in General Method 6 from 1.0 mmol of 3-bromo-5,6-dihydro-4- hydroxy-6,6-diphenyl-2H-pyran-2-one (prepared in example AAA), 1.05 mmol of 2-isopropylbenzenethiol, and 1.05 mmol of piperidine in 20 mL of dichloromethane. The product was triturated with ether to afford a solid (m.p. 216°–217° C.). $^1$H NMR (DMSO-d$_6$) δ 1.17 (d, J=6.8 Hz, 6 H), 3.20 (m, 1 H), 3.77 (bs, 2 H), 5.64 (d, 1 H), 6.45 (t, 1 H), 6.92 (t, 1 H), 7.12 (d, 1 H), 7.32 –7.48 (m, 10 H).

EXAMPLE 69

5,6-Dihydro-4-hydroxy-6,6-diphenyl-3-phenylthio-2H-pyran-2-one

The title compound was prepared as described in General Method 6 from 0.96 mmol of 3-bromo-5,6-dihydro-4-hydroxy-6,6 -diphenyl-2H-pyran-2-one (prepared in example AAA), 1.0 mmol of benzenethiol, and 1.0 mmol of piperidine in 20 mL of dichloromethane. The product was triturated with hexane:ether (1:1) to afford a solid (m.p. 78°–80° C.). $^1$H NMR (DMSO-d$_6$) δ 3.37 (bs, 2 H), 6.35 (m, 2 H), 6.93 (m, 3 H), 7.29–7.49 (m, 10 H).

EXAMPLE 70

5,6-Dihydro-4-hydroxy-3-(3-methylphenylthio)-6,6-diphenyl-2H-pyran-2-one

The title compound was prepared as described in General Method 6 from 1.3 mmol of 3-bromo-5,6-dihydro-4-hydroxy-6,6-diphenyl-2H-pyran-2-one (prepared in example AAA), 1.4 mmol of 3-methylbenzenethiol, and 1.4 mmol of piperidine in 25 mL of dichloromethane. The product was triturated with hexane:ether (1:1) to afford a solid which was dissolved in 2N NaOH, washed with ether, acidified to pH 2, and extracted with ethyl acetate. The extract was washed with water, dried over MgSO$_4$, and concentrated to give a solid (m.p. 58 –60° C.). $^1$H NMR (DMSO-d$_6$) δ 2.07 (s, 3 H), 3.77 (s, 2 H), 6.06 (m, 1 H), 6.45 (s, 1 H), 6.78 (m, 2 H), 7.25–7.47 (m, 10 H).

EXAMPLE 71

5,6-Dihydro-4-hydroxy-6-phenyl-6-(2-phenylethyl)-3-phenylthio-2H-pyran-2-one (+/–)

The title compound was prepared as described in General Method 6 from 1.50 mmol of 3-bromo-5,6-dihydro-4-hydroxy-6-phenyl-6-(2-phenylethyl)-2H-pyran-2-one (prepared in example BBB), 1.60 mmol of benzenethiol, and 1.60 mmol of piperidine in 30 mL of dichloromethane. The product was triturated with hexane:ether (1:1) to afford a solid. The crude product was chromatographed on silica gel, eluting first with chloroform and then with 5% methanol in chloroform, to give the title compound (m.p. 58°–60° C.). $^1$H NMR (DMSO-d$_6$) δ 2.22–2.39 (m, 3 H), 2.62 (m, 1 H), 3.46 (q, 2 H), 6.48 (m, 2 H), 6.98 (m, 3 H), 7.15 (m, 3 H), 7.25 (m, 2 H), 7.46 (m, 5 H).

EXAMPLE 72

5,6-Dihydro-4-hydroxy-3-(2-isopropylphenylthio) -6-phenyl-6-(2-phenylethyl)-2H-pyran-2-one (+/–)

The title compound was prepared as described in General Method 6 from 1.50 mmol of 3-bromo-5,6-dihydro-4-hydroxy-6-phenyl-6-(2-phenylethyl)-2H-pyran-2-one (prepared in example BBB), 1.60 mmol of 2-isopropylbenzenethiol, and 1.60 mmol of piperidine in 30 mL of dichloromethane. The product was triturated with hexane:ether (1:1) to afford a solid. The crude product was chromatographed on silica gel, eluting first with chloroform and then with 5% methanol in chloroform, to give the title compound (m.p. 66°–67° C.). $^1$H NMR (DMSO-d$_6$) δ 1.16 (t, 6 H), 2.21–2.35 (m, 3 H), 2.60 (m, 1 H), 3.21 (m, 1 H), 3.42 (q, 2 H), 5.88 (d, 1 H), 6.56 (t, 1 H), 6.94 (t, 1 H), 7.13 (m, 4 H), 7.25 (m, 2 H), 7.45 (m, 5 H).

EXAMPLE 73

5,6-Dihydro-4-hydroxy-3-(3-methylphenylthio)-6-phenyl-6-(2-phenylethyl)-2H-pyran-2-one (+/–)

The title compound was prepared as described in General Method 6 from 2.0 mmol of 3-bromo-5,6-dihydro-4-hydroxy-6-phenyl-6-(2-phenylethyl)-2H-pyran-2-one (prepared in example BBB), 2.2 mmol of 3-methylbenzenethiol, and 2.2 mmol of piperidine in 30 mL of dichloromethane. The crude product was chromatographed on silica gel, eluting first with chloroform and then with 5% methanol in chloroform, to give the title compound (m.p. 68°–70° C.). $^1$H NMR (DMSO-d$_6$) δ 2.06 (s, 3 H), 2.18–2.36 (m, 3 H), 2.60 (m, 1 H), 3.38 (2 H+H$_2$O), 6.26 (d, 1 H), 6.46 (s, 1 H), 6.75 (m, 1 H), 6.83 (t, 1 H), 7.15 (m, 3 H), 7.24 (m, 2 H), 7.45 (m, 5 H).

EXAMPLE 74

5-[3,6-Dihydro-4-hydroxy-5-(2-isopropylphenyl-thio)-6-oxo-2-phenyl-2H-pyran-2-yl]pentanoic acid (+/–)

The title compound was prepared as described in General Method 6 from 1.1 mmol of 5-[5-bromo-3,6-dihydro-4-hydroxy-6-oxo-2-phenyl-2H-pyran-2-yl]pentanoic acid (prepared in example DDD), 1.3 mmol of 2-isopropylbenzenethiol, and 1.3 mmol of piperidine in 20 mL of dichloromethane. The crude product was chromatographed on silica gel, eluting first with 5% methanol in chloroform and then with 9:1:0.5 chloroform:methanol:acetic acid, to give the title compound, (m.p. 145°–146° C.). $^1$H NMR (DMSO-d$_6$) δ 1.07–1.19 (t plus m, 7 H), 1.25 (m, 1 H), 1.43 (m, 2 H), 1.91 (m, 2 H), 2.15 (t, 2 H), 3.19 (m, 1 H), 3.41 (2 H+H$_2$O), 5.81 (d, 1 H), 6.54 (t, 1 H), 6.93 (t, 1 H), 7.12 (d, 1 H), 7.29–7.44 (m, 5 H).

EXAMPLE 75

5,6-Dihydro-4-hydroxy-6-(3-methylbutyl)-6-phenyl-3-(2-isopropyl-phenylthio)-2H-pyran-2-one, (+/–)

The title compound was prepared as described in General Method 6 from 2.0 mmol of 3-bromo-5,6-dihydro-4-hydroxy-6-(3-methylbutyl)-6-phenyl-2H-pyran-2-one (prepared in example CCC), 2.2 mmol of 2-isopropylbenzenethiol, and 2.2 mmol of piperidine in 30 mL of dichloromethane. The crude product was chromatographed on silica gel, eluting first with chloroform and then with 5% methanol in chloroform, to give the title compound (m.p. 64°–66° C.). $^1$H NMR (DMSO-d$_6$) δ 0.80 (m, 6 H), 0.95 (m, 1 H), 1.17 (t, 7 H), 1.42 (m, 1 H), 1.93 (m, 2 H), 3.20 (m, 1 H), 3.45 (2 H+H$_2$O), 5.84 (d, 1 H), 6.55 (t, 1 H), 6.93 (t, 1 H), 7.12 (d, 1 H), 7.40 (m, 5 H).

EXAMPLE 76

5,6-Dihydro-4-hydroxy-6-(3-methylbutyl)-6-phenyl-3-phenylthio-2H-pyran-2-one, (+/–)

The title compound was prepared as described in General Method 6 from 1.5 mmol of 3-bromo-5,6-dihydro-4- hydroxy-6-(3-methylbutyl)-6-phenyl-2H-pyran-2-one (prepared in example CCC), 1.6 mmol of benzenethiol, and 1.6 mmol of piperidine in 20 mL of dichloromethane. The crude product was chromatographed on silica gel, eluting first with chloroform and then with 5% methanol in chloroform, to give the title compound, (m.p. 154°–155° C.). $^1$H NMR (DMSO-d$_6$) δ 0.80 (m, 6 H), 0.97 (m, 1 H), 1.16 (m, 2 H), 1.42 (m, 1 H), 1.91 (m, 2 H), 3.40 (2 H+H$_2$O), 6.45 (m, 2 H), 6.93 (m, 3 H), 7.37 (m, 5 H).

EXAMPLE 77

Methyl 2-[[5,6-dihydro-4-hydroxy-6-(3-methylbutyl)-2-oxo-6-phenyl-2H-pyran-3-yl]thio]benzoate The title compound was prepared as described in General Method 6 from 1.9 mmol of 3-bromo-5,6-dihydro-4-hydroxy-6-(3-methylbutyl)-6-phenyl-2H-pyran-2-one (prepared in example CCC), 2.2 mmol of methyl thiosalicylate and 2.1 mmol of piperidine in 30 mL of dichloromethane. The crude product was chromatographed on silica gel, eluting first with chloroform and then with 5% methanol in chloroform, to give the title compound (m.p. 115°–116° C.). $^1$H NMR (DMSO-d$_6$) δ 0.80 (m, 6 H), 1.0 (m, 1 H), 1.17 (m, 1 H), 1.43 (m, 1 H), 1.96 (m, 2 H), 3.4 (2 H+H$_2$O), 3.81 (s, 3 H), 6.02 (bd, 1 H), 6.88 (t, 1 H), 7.05 (t, 1 H), 7.42 (m, 5 H), 7.80 (dd, 1 H).

EXAMPLE 78

2-[[5,6-Dihydro-4-hydroxy-6-(3-methylbutyl)-2-oxo-6-phenyl-2H-pyran-3-yl]thio]benzoic acid (+/−)

A solution of 0.3 mmol of the compound prepared in Example 77 in 15 mL of 1N sodium hydroxide was stirred at room temperature for 3 hours. The solution was washed with ether and then acidified to pH 2.0 with 6N hydrochloric acid. The solution was extracted with ethyl acetate, and the extract was washed with brine, dried over magnesium sulfate, and concentrated to give the title compound (m.p. 99°–101° C.). $^1$H NMR (DMSO-d$_6$) δ 0.80 (m, 6 H), 0.95 (m, 1 H), 1.15 (m, 1 H), 1.43 (m, 1 H), 1.91 (m, 2 H), 3.4 (2 H+H$_2$O), 6.05 (d, 1 H), 6.85 (bt, 1 H), 7.03 (t, 1 H), 7.42 (m, 5 H), 7.79 (dd, 1 H).

EXAMPLE 79

5,6-Dihydro-3-(2-sec-butylphenylthio)-4-hydroxy-6,6-diphenyl-2H-pyran-2-one (+/−)

The title compound was prepared as described in General Method 6 from 1.6 mmol of 3-bromo-5,6-dihydro-4-hydroxy-6,6-diphenyl-2H-pyran-2-one (prepared in example AAA), 1.7 mmol of 2-sec-butylbenzenethiol, and 1.7 mmol of piperidine in 25 mL of dichloromethane. The product was chromatographed on silica gel, eluting first with chloroform and then with 5% methanol in chloroform, to give the title compound (m.p. 161°–162° C.). $^1$H NMR (DMSO-d$_6$) δ 0.81 (t, 3 H), 1.15 (d, 3 H), 1.43–1.64 (m, 2 H), 2.98 (m, 1 H), 3.77 (s, 2 H), 5.65 (dd, 1 H), 6.47 (t, 1 H), 6.92 (t, 1 H), 7.07 (d, 1 H), 7.34–7.48 (m, 10 H), 12.4 (bs, 1 H).

EXAMPLE 80

5,6-Dihydro-4-hydroxy-3-(2-methoxyphenylthio)-6,6-diphenyl-2H-pyran-2-one

The title compound was prepared as described in General Method 6 from 1.5 mmol of 3-bromo-5,6-dihydro-4-hydroxy-6,6-diphenyl-2H-pyran-2-one (prepared in example AAA), 1.6 mmol of 2-methoxybenzenethiol, and 1.6 mmol of piperidine in 25 mL of dichloromethane. The product was chromatographed on silica gel, eluting first with chloroform and then with 5% methanol in chloroform, to give the title compound (m.p. 170°–172° C. dec.). $^1$H NMR (DMSO-d$_6$) δ 3.76 (bs, 5 H), 5.44 (dd, 1 H), 6.26 (t, 1 H), 6.85 (m, 1 H), 6.91 (t, 1 H), 7.34–7.50 (m, 10 H).

EXAMPLE 81

5,6-Dihydro-3-(2-sec-butylphenylthio)-4-hydroxy-6-phenyl-6-(2-phenylethyl)-2H-pyran-2-one (+/−)

The title compound was prepared as described in General Method 6 from 2.0 mmol of 3-bromo-5,6-dihydro-4-hydroxy-6-phenyl-6-(2-phenylethyl)-2H-pyran-2-one (prepared in example BBB), 2.1 mmol of 2-sec-butylbenzenethiol, and 2.1 mmol of piperidine in 25 mL of dichloromethane. The product was chromatographed on silica gel, eluting first with chloroform and then with 5% methanol in chloroform, to give the title compound (m.p. 67°–68° C.). $^1$H NMR (DMSO-d$_6$) δ 0.82 (q, 3 H), 1.09 (t, 3 H), 1.46–1.61 (m, 2 H), 2.26 (m, 2 H), 2.35 (m, 1 H), 2.62 (m, 1 H), 2.98 (m, 1 H), 3.47 (q, 2 H), 5.90 (t, 1 H), 6.56 (t, 1 H), 6.94 (t, 1 H), 7.07–7.18 (m, 4 H), 7.25 (m, 2 H), 7.45 (m, 5 H).

EXAMPLE 82

5,6-Dihydro-4-hydroxy-3-(4-methyl-2-isopropylphenylthio)-6,6-dipbenyl-2H-pyran-2-one The title compound was prepared as described in General Method 6 from 2.0 mmol of 3-bromo-5,6-dihydro-4-hydroxy-6,6-diphenyl-2H-pyran-2-one (prepared in example AAA), 2.1 mmol of 4-methyl-2-isopropylbenzenethiol, and 2.1 mmol of piperidine in 30 mL of dichloromethane. The product was chromatographed on silica gel, eluting first with chloroform and then with 5% methanol in chloroform (m.p. 185°–186° C.). $^1$H NMR (DMSO-d$_6$) δ 1.17 (d, J=10 Hz, 6 H), 2.15 (s, 3 H), 3.17 (m, 1 H), 3.76 (bs, 2 H), 5.56 (d, 1 H), 6.29 (d, 1 H), 6.94 (s, 1 H), 7.32–7.47 (m, 10 H).

EXAMPLE 83

5,6-Dihydro-4-hydroxy-3-(3-methoxyphenylthio)-6,6-diphenyl-2H-pyran-2-one

The title compound was prepared as described in General Method 6 from 1.8 mmol of 3-bromo-5,6-dihydro-4-hydroxy-6,6-diphenyl-2H-pyran-2-one (prepared in example AAA), 2.0 mmol of 3-methoxybenzenethiol, and 2.0 mmol of piperidine in 25 mL of dichloromethane. The product was chromatographed on silica gel, eluting first with chloroform and then with 5% methanol in chloroform (m.p. 61°–62° C.). $^1$H NMR (DMSO-d$_6$) δ 3.63 (s, 3 H), 3.76 (s, 2 H), 5.64 (bd, 1 H), 6,42 (s, 1 H), 6.54 (d, 1 H), 6.74 (t, 1 H), 7.32–7.47 (m, 10 H).

EXAMPLE 84

5,6-Dihydro-4-hydroxy-3-(5-methyl-2-isopropylphenylthio)-6,6-diphenyl-2H-pyran-2-one The title compound was prepared as described in General Method 6 from 2.0 mmol of 3-bromo-5,6-dihydro-4-hydroxy-6,6-diphenyl-2H-pyran-2-one (prepared in example AAA), 2.1 mmol of 5-methyl-2- isopropylbenzenethiol, and 2.1 mmol of piperidine in 30 mL of dichloromethane. The product was chromatographed on silica gel, eluting first with chloroform and then with 5% methanol in chloroform (m.p. 183°–184° C.). $^1$H NMR (DMSO-$d_6$) δ 1.15 (d, 6 H), 1.85 (s, 3 H), 3.22 (m, 1 H), 3.80 (bs, 2 H), 5.88 (bs, 1 H), 6.77 (d, 1 H), 7.03 (d, 1 H), 7.32–7.47 (m, 10 H).

EXAMPLE 85

5,6-Dihydro-4-hydroxy-3-(5-methyl-2-isopropylphenylthio)-6-phenyl-6-(2-phenylethyl)-2H-pyran-2-one (+/−)

The title compound was prepared as described in General Method 6 from 2.0 mmol of 3-bromo-5,6-dihydro-4-hydroxy-6-phenyl-6-(2-phenylethyl)-2H-pyran-2-one (prepared in example BBB), 2.1 mmol of 5-methyl-2-isopropylbenzenethiol, and 2.1 mmol of piperidine in 30 mL of dichloromethane. The product was chromatographed on silica gel, eluting first with chloroform and then with 5% methanol in chloroform (m.p. 66°–67° C.). $^1$H NMR (DMSO-$d_6$) δ 1.16 (m, 6 H), 1.87 (s, 3 H), 2.26 (m, 3 H), 2.57 (m, 1 H), 3.23 (m, 1 H), 3.43 (q, 2 H), 6.01 (bs, 1 H), 6.78 (d, 1 H), 7.03–7.27 (m, 6 H), 7.37–7.47 (m, 5 H).

EXAMPLE 86

5,6-Dihydro-3-(4-chloro-2-isopropylphenylthio)-4-hydroxy-6,6-diphenyl-2H-pyran-2-one The title compound was prepared as described in General Method 6 from 2.0 mmol of 3-bromo-5,6-dihydro-4-hydroxy-6,6-diphenyl-2H-pyran-2-one (prepared in example AAA), 2.1 mmol of 4-chloro-2-isopropylbenzenethiol, and 2.1 mmol of piperidine in 30 mL of dichloromethane. The product was chromatographed on silica gel, eluting first with chloroform and then with 5% methanol in chloroform (m.p. 95°–96° C.). $^1$H NMR (DMSO-$d_6$) δ 1.16 (d, 6 H), 3.23 (m, 1 H), 3.73 (bs, 2 H), 5.60 (d, 1 H), 6.45 (d, 1 H), 7.14 (d, 1 H), 7.32–7.48 (m, 10 H).

EXAMPLE 87

5,6-Dihydro-4-hydroxy-3-(4-methyl-2-isopropylphenylthio)-6-phenyl-6-(2-phenylethyl)-2H-pyran-2-one (+/−)

The title compound was prepared as described in General Method 6 from 2.0 mmol of 3-bromo-5,6-dihydro-4-hydroxy-6-phenyl-6-(2-phenylethyl)-2H-pyran-2-one (prepared in example BBB), 2.1 mmol of 4-methyl-2-isopropylbenzenethiol, and 2.1 mmol of piperidine in 30 mL of dichloromethane. The product was chromatographed on silica gel, eluting first with chloroform and then with 5% methanol in chloroform (m.p.75°–76 ° C.). $^1$H NMR (DMSO-$d_6$) δ 1.15 (m, 6 H), 2.16 (s, 3 H), 2.19–2.36 (m, 3 H), 2.62 (m, 1 H), 3.21 (m, 1 H), 3.44 (q, 2 H), 5.82 (d, 1 H), 6.40 (dd, 1 H), 6.95 (d, 1 H), 7.10–7.18 (m, 3 H), 7.25 (m, 2 H), 7.44 (m, 5 H).

EXAMPLE 88

Methyl 2-[[5,6-dihydro-4-hydroxy-2-oxo-6-(2-phenylethyl)-6-phenyl-2H-pyran-3-yl]thio]benzoate (+/−)

The title compound was prepared as described in General Method 6 from 1.9 mmol of 3-bromo-5,6-dihydro-4-hydroxy-6-phenyl-6-(2-phenylethyl)-2H-pyran-2-one (prepared in example BBB), 2.2 mmol of methyl thiosalicylate and 2.1 mmol of piperidine in 30 mL of dichloromethane. The crude product was chromatographed on silica gel, eluting first with chloroform and then with 5% methanol in chloroform, to give the title compound (m.p. 91°–92° C.). $^1$H NMR (DMSO-$d_6$) δ 2.25 (m, 2 H), 2.38 (m, 1 H), 2.62 (m, 1 H), 3.44 (q, 2 H), 3.82 (s, 3 H), 6.06 (bd, 1 H), 6.90 (t, 1 H), 7.05–7.52 (m, 11 H), 7.81 (dd, 1 H).

GENERAL METHOD 7

The desired compounds were prepared by adding the 5,6-dihydropyro-2H-pyran-2-one, absolute ethanol, the p-toluenethiosulfonate reagent (prepared in general method 2), sodium bicarbonate, and $Et_3N$ to a reaction vessel. The mixture was then subsequently heated to 40° C. for 4 to 48 h. The mixture was then diluted with $H_2O$, acidified with conc. HCl, and the product extracted with diethyl ether, $CH_2Cl_2$, or ethyl acetate. The organic layers were combined and dried with $Na_2SO_4$.

EXAMPLE 89

5,6-Dihydro-4-hydroxy-6-phenyl-6-(2-phenylethyl)-3-[(2-rifluoromethylphenyl)methylthio]-2H-pyran-2-one (+/−)

The title compound was prepared as described in General Method 1 using the following: 5,6-dihydro-4-hydroxy-6-phenyl-6-(2-phenylethyl)-2H-pyran-2-one (0.250 g, 0.850 mmol), (2-trifluoromethyl)benzyl-p-toluenethiosulfonate (0.350 g, 1.02 mmol), $Et_3N$ (0.280 mL, 2.00 mmol), $NaHCO_3$ (0.68 mmol), (0.50 g), absolute ethanol (3.0 mL). The mixture was heated to 40° C. for 16 h then diluted with diethyl ether (100 mL), and washed with $H_2O$. The solvent was then removed in vacuo and the residue submitted to column chromatography ($SiO_2$, 100% $CH_2Cl_2$ to 2% methanol in $CH_2Cl_2$) to provide a solid (0.316 g, m.p. 59°–62° C.). $^1$H NMR (400 MHz, DMSO-$d_6$) δ 7.603–7.581 (m, 1 H), 7.432–7.026 (m, 13 H), 3.780 (d, 1 H, J=14 Hz), 3.69 (d, 1 H, J=14 Hz), 3.310 (d, 1 H, J=17.5 Hz), 3.220 (d, 1 H, J=17.5 Hz), 2.5677–2.505 (m, 1 H), 2.253–2.157 (m, 3 H).

EXAMPLE 90

5,6-Dihydro-4-hydroxy-3-[(2,5-dimethylphenyl)methylthio]-6-phenyl-6-(2-phenylethyl)-2H-pyran-2-one (+/−).

The title compound was prepared as described in General Method 7 using the following: 5,6-dihydro-4-hydroxy-6-phenyl-6-(2-phenylethyl)-2H-pyran-2-one (0.250 g, 0.850 mmol), 2,5-dimethylbenzyl-p-toluenethiosulfonate (0.312 g, 1.02 mmol), $Et_3N$ (0.230 mL, 1.60 mmol), $NaHCO_3$ (0.071 g, 0.85 mmol), absolute ethanol (3.0 mL). The mixture was heated to 40° C. for 16 h then diluted with diethyl ether (100 mL), and washed with $H_2O$. The solvent was then removed in vacuo and the residue submitted to column chromatography ($SiO_2$, 100% $CH_2Cl_2$ to 2% methanol in $CH_2Cl_2$) to provide a solid (0.116 g, m.p. 54°–56° C.) which was dried in vacuo. $^1$H NMR (400 MHz, DMSO-$d_6$) δ 11.498 (bs, 1 H), 7.405–7.380 (m, 4 H), 7.327–7.285 (m, 1 H), 7.258–7.221 (m, 2 H), 7.168–7.128 (m, 1 H), 7.090 (d, 2 H, J=7.5 Hz), 6.970 (d, 1 H, J=8 Hz), 6.890 (d, 1 H, J=8 Hz), 6.821 (s, 1 H), 3.600 (d, 1 H , J=11 Hz), 3.505 (d, 1 H, J=11 Hz), 3.250 (d, 1 H, J=17 Hz), 3.176 (d, 1 H, J=17), 2.619–2.564 (m, 1 H), 2.235–2.168 (m, 9 H).

EXAMPLE 91

5,6-Dihydro-4-hydroxy-3-(naphthalen-1-ylmethylthio)-6-phenyl-6-(2-phenylethyl)-2H-pyran-2-one (+/−).

The title compound was prepared as described in General Method 7 using the following: 5,6-dihydro-4-hydroxy-6- phenyl-6-(2-phenylethyl)-2H-pyran-2-one (0.20 g, 0.68 mmol), (1-naphthalen-1-ylmethyl)-p-toluenethiosulfonate (0.27 g, 0.82 mmol), Et$_3$N (0.18 mL, 1.3 mmol), NaHCO$_3$ (0.68 mmol) absolute ethanol (3.0 mL). The mixture was heated to 40° C. for 16 h then diluted with diethyl ether (100 mL), and washed with H$_2$O. The solvent was then removed in vacuo and the residue submitted to column chromatography (SiO$_2$, 100% CH$_2$Cl$_2$ ) to provide a solid (0.158 g, m.p. 132°–134° C/). $^1$H NMR (400 MHz, DMSO-d$_6$) δ 11.533 (bs, 1 H), 8.177 (d, 1 H, J=8 Hz), 7.886 (dd, 1 H, J=2 Hz, J=7 Hz), 7.761 (d, 1 H, J=8 Hz), 7.501–7.05 ( m, 14 H), 4.120 (d, 1 H, J=12 Hz), 3.995 (d, 1 H, J=12 Hz), 3.274 (d, 1 H, J=18 Hz), 3.194 ( d, 1 H, J=18 Hz), 2.636–2.581 (m, 1 H), 2.288–2.169 (m, 3 H).

EXAMPLE 92

3-(Biphenyl-2-ylmethylthio)-5,6-dihydro-4-hydroxy-6-phenyl-6-(2-phenylethyl)-2H-pyran-2-one (+/−).

The title compound was prepared as described in General Method 7 using the following: 5,6-dihydro-4-hydroxy-6-phenyl-6-(2-phenylethyl) -2H-pyran-2-one (0.250 g, 0.85 mmol), (biphen-2-ylmethyl)-p-toluenethiosulfonate (0.360 g, 1.02 mmol), Et$_3$N (0.14 mL, 1.0 mmol), NaHCO$_3$ (0.85 mmol) absolute ethanol (5.0 mL). The mixture was heated to 40° C. for 16 h then diluted with diethyl ether (100 mL), and washed with H$_2$O. The solvent was then removed in vacuo and the residue submitted to column chromatography (SiO$_2$, 100% CH$_2$Cl$_2$ to 1% methanol in CH$_2$Cl$_2$) to provide a solid (0.317 g, m.p. 58°–60° C.). $^1$H NMR (400 MHz, DMSO-d$_6$) δ 11.569 (bs, 1 H), 7.429–7.066 (m, 19 H), 3.528 (d, 1 H, J=12 Hz), 3.477 (d, 1 H, J=12 Hz), 3.280 (dd, 1 H, J=17 Hz), 3.183 (d, 1 H, J=17 Hz), 2.607–2.502 (m, 1 H), 2.246–2.144 (m, 3 H).

EXAMPLE 93

3-(2-Chlorophenylmethylthio)-5,6-dihydro-4-hydroxy-6-phenyl-6-(2-phenylethyl)-2H-pyran-2-one (+/−).

The title compound was prepared as described in General Method 7 using the following: 5,6-dihydro-4-hydroxy-6-phenyl-6-(2-phenylethyl)-2H-pyran-2-one (0.250 g, 0.85 mmol), (2-cholorbenzyl)-p-toluenethiosulfonate (0.320 g, 1.02 mmol), Et$_3$N (0.14 mL, 1.0 mmol), absolute ethanol (5.0 mL). The mixture was heated to 40° C. for 16 h then diluted with diethyl ether (100 mL), and washed with H$_2$O. The solvent was then removed in vacuo and the residue submitted to column chromatography (SiO$_2$, 100% CH$_2$Cl$_2$ to 2% methanol in CH$_2$Cl$_2$) to provide a solid (0.317 g, m.p. 53°–55° C.). $^1$H NMR (400 MHz, DMSO-d$_6$) δ 11.551 (bs, 1 H), 7.435–7.005 (m, 13 H), 6.800 (dd, 1 H, J=1.5 Hz, J=7.5 Hz) , 3.750 (d, 1 H, J=13 Hz), 3.620 (d, 1 H, J=13 Hz), 3.251 (d, 1 H, J=17 Hz), 3.171 (d, 1 H, J=17 Hz) 2.595–2.542 (m, 1 H), 2.233–2.125 (m, 3 H).

EXAMPLE 94

3-(2-Chlorophenylmethylthio)-5,6-dihydro-4-hydroxy-6-(3-methylbutyl) -6-phenyl-2H-pyran-2-one (+/−).

The title compound was prepared as described in General Method 7 using the following: 5,6-dihydro-4-hydroxy-6-phenyl-6-(3-methylbutyl)-2H-pyran-2-one (0.250 g, 0.85 mmol), (2-chlorobenzyl)-p-toluenethiosulfonate (0.390 g, 1.24 mmol), Et$_3$N (0.17 mL, 1.24 mmol), absolute ethanol (5.0 mL), NaHCO$_3$ (0.5 g). The mixture was heated to 40° C. for 16 h then diluted with diethyl ether (100 mL), and washed with H$_2$O. The solvent was then removed in vacuo and the residue submitted to column chromatography (SiO$_2$, 100% CH$_2$Cl$_2$ to 2% methanol in CH$_2$Cl$_2$) to provide a thick oil (0.36 g) which was dried in vacuo. $^1$H NMR (400 MHz, DMSO-d$_6$) δ 7.388–7.267 (m, 6 H), 7.181 (td, 1 H, J =1.5 Hz, J=7.5 Hz), 7.052 (t, 1 H, J=7.5 Hz), 6.800 (dd, 1 H, J=1.5 Hz, J=7.5 Hz), 3.718 (d, 1 H, J=13 Hz), 3.596 (d, 1 H, J=13 Hz), 3.112 (s, 2 H), 1.921–1.797 (m, 2 H), 1.402–1.320 (m, 1 H), 1.156–1.065 (m, 1 H), 0.844–0.739 (m, 7 H).

EXAMPLE 95

3-(Biphen-2-ylmethylthio)-5,6-dihydro-4-hydroxy-6-(3-methylbutyl) -6-phenyl-2H-pyran-2 -one (+/−).

The title compound was prepared as described in General Method 7 using the following: 5,6-dihydro-4-hydroxy-6-phenyl-6-(3-methylbutyl)-2H-pyran-2-one (0.250 g, 0.96 mmol), (2-methylbiphenyl)-p-toluenethiosulfonate (0.439 g, 1.24 mmol), Et$_3$N (0.17 mL, 1.24 mmol), absolute ethanol (3.0 mL), NaHCO$_3$ (0.5 g). The mixture was heated to 40° C. for 16 h then diluted with diethyl ether (100 mL), and washed with H$_2$O. The solvent was then removed in vacuo and the residue submitted to column chromatography (SiO$_2$, 100% CH$_2$Cl$_2$ to 2% methanol in CH$_2$Cl$_2$) to provide a solid (0.33 g, m.p. 49°–51° C.). $^1$H NMR (400 MHz, DMSO-d$_6$) δ 7.425–7.153 (m, 13 H), 7.74 (dd, 1 H, J=1 Hz, J=7 Hz), 3.480 (dd, 2 H, J=12 Hz, J=17 Hz), 3.149 (dd, 2 H, J=17 Hz, J=22 Hz), 1.921–1.821 (m, 2 H), 1.402–1.336 (m, 1 H), 1.161–1.071 (m, 1 H), 0.847–0.707 (m, 7 H).

EXAMPLE 96

5,6-Dihydro-3-(2,5-dimethylphenylmethylthio) -4-hydroxy-6-(3-methylbutyl)-6-phenyl-2H-pyran-2-one (+/−).

The title compound was prepared as described in General Method 7 using the following: 5,6-dihydro-4-hydroxy-6-(3-methylbutyl) -6-phenyl-2H-pyran-2-one (0.250 g, 0.96 mmol), (2,5-dimethylbenzyl) -p-toluenethiosulfonate (0.380 g, 1.24 mmol), Et$_3$N (0.17 mL, 1.24 mmol), absolute ethanol (3.0 mL), NaHCO$_3$ (0.5 g). The mixture was heated to 40° C. for 16 h then diluted with diethyl ether (100 mL), and washed with H$_2$O. The solvent was then removed in vacuo and the residue submitted to column chromatography (SiO$_2$, 100% CH$_2$Cl$_2$ to 2% methanol in CH$_2$Cl$_2$) to provide a thick oil (0.286 g). $^1$H NMR (400 MHz, DMSO-d$_6$) δ 11.433 (bs, 1 H), 7.380–7.251 (m, 5 H), 6.973 (d, 1 H, J=7.5 Hz), 6.905 (d, 1 H, J=7.5 Hz), 6.187 (s, 1 H), 3.584 (d, 1 H, J=11.5 Hz), 3.481 (d, 1 H, J=11.5 Hz), 3.133 (s, 2 H), 2.209 (s, 3 H), 2.184 (s, 3 H), 1.933–1.858 (m, 2 H), 1.421–1.355 (m, 1 H), 1.177–1.086 (m, 1 H), 0.870–0.751 (m, 7 H).

EXAMPLE 97

5,6-Dihydro-4-hydroxy-3-(3-methoxyphenylmethylthio)-6-phenyl-6-(2-phenylethyl)-2H-pyran-2-one (+/−).

The title compound was prepared as described in General Method 7 using the following: 5,6-dihydro-4-hydroxy-6-phenyl-(2-phenylethyl)-2H-pyran-2-one (0.250 g, 0.85 mmol), (3-methoxybenzyl) -p-toluenethiosulfonate (0.340 g, 1.11 mmol), Et$_3$N (0.25 mL, 1.81 mmol), absolute ethanol (3.0 mL), NaHCO$_3$ (0.5 g). The mixture was heated to 40° C. for 16 h then diluted with diethyl ether (100 mL), and washed with H₂O. The solvent was then removed in vacuo and the residue submitted to column chromatography (SiO₂, 100% CH₂Cl₂ to 2% methanol in CH₂Cl₂) to provide a thick oil (0.286 g). $^1$H NMR (400 MHz, DMSO-d₆) δ 77.411–7.376 (m, 4 H), 7.361–7.280 (m, 1 H), 7.235 (t, 2 H, J=7 Hz), 7.146 (t, 1 H, J=7 Hz), 7.078–7.019 (m, 3 H), 6.769 (d, 1 H, J=2 H), 6.762–6.698 (m, 1 H), 6.555 (d, 1 H, J=7 Hz), 3.694 (s, 3 H), 3.670 (d, 1 H, J=13 Hz), 3.585 (d, 1 H, J=13 Hz), 3.220 (d, 1 H, J=17 Hz), 3.158 (d, 1 H, J=17), 2.590–2.525 (m, 1 H), 2.219–2.141 (m, 3 H).

EXAMPLE 98

3-(Biphenyl-2-ylmethylthio)-5,6-dihydro-4-hydroxy-6,6-diphenyl-2H-pyran-2-one.

The title compound was prepared as described in General Method 7 using the following: 5,6-dihydro-4-hydroxy-6,6-diphenyl-2H-pyran-2-one (0.250 g, 0.94 mmol), (2-methylbiphenyl) -p-toluenethiosulfonate (0.389 g, 1.1 mmol), Et₃N (0.26 ML, 1.9 mmol), absolute ethanol (5.0 mL), NaHCO₃ (0.5 g). The mixture was heated to 40° C. for 16 h, then diluted with diethyl ether (100 mL) and washed with H₂O. The solvent was then removed in vacuo and the residue submitted to column chromatography (SiO₂, 100% CH₂Cl₂ to 2% methanol in CH₂Cl₂) to provide a thick oil (0.286 g). $^1$H NMR (400 MHz, DMSO-d₆) δ 11.770 (bs, 1 H), 7.434–7.148 (m, 18 H), 6.969 (d, 1 H, J=7 Hz), 3.595 (s, 2 H), 3.407 (s, 2 H).

EXAMPLE 99

3-(3-Chlorophenylmethylthio)-5,6-dihydro-4-hydroxy-6-phenyl-6-(2-phenylethyl)-2H-pyran-2-one (+/−).

The title compound was prepared as described in General Method 7 using the following: 5,6-dihydro-4-hydroxy-6-phenyl-(2-phenylethyl)-2H-pyran-2-one (0.250 g, 0.85 mmol), [(3-chlorophen-1-yl)methyl]-p-toluenethiosulfonate (0.340 g, 1.11 mmol), Et₃N (0.25 mL, 1.81 mmol), absolute ethanol (3.0 mL), NaHco₃ (0.5 g). The mixture was heated to 40° C. for 16 h, then diluted with diethyl ether (100 mL) and washed with H₂O. The solvent was then removed in vacuo and the residue submitted to column chromatography (SiO₂, 100% CH₂Cl₂to 2% methanol in CH₂Cl₂) to provide a thick oil (0.155 g). $^1$H NMR (400 MHz, DMSO-d₆) δ 7.420–7.060 (m, 13 H), 6.848 (d, I H, J=7 Hz), 3.688 (d, 1 H, J=13 Hz), 3.597 (d, 1 H, J=13 Hz), 3.219 (d, 1 H, J=17 Hz), 3.153 (d, 1 H, J=17 Hz), 2.592–2.526 (m, 1 H), 2.241 −2.120 (m, 3 H).

EXAMPLE 100

5,6-Dihydro-4-hydroxy-6-(2-phenylethyl)-6-phenyl-3-[((3-trifluoromethyl)phenyl)methylthio]-2H-pyran-2-one (+/−).

The title compound was prepared as described in General Method 7 using the following: 5,6-dihydro-4-hydroxy-6-phenyl-(2-phenylethyl)-2H-pyran-2-one (0.250 g, 0.85 mmol), [(3-trifluoromethylphen-1-yl)methyl]-p-toluenethiosulfonate (0.380 g, 1.11 mmol), Et₃N (0.25 mL, 1.81 mmol), absolute ethanol (3.0 mL), NaHCO₃ (0.5 g). The mixture was heated to 40° C. for 16 h, then diluted with diethyl ether (100 mL) and washed with H₂O.

The solvent was then removed in vacuo and the residue submitted to column chromatography (SiO₂, 100% CH₂Cl₂ to 2% methanol in CH₂Cl₂) to provide a thick oil (0.273 g). $^1$H NMR (400 MHz, DMSO-d₆) δ 11.60 (bs, 1 H), 7.523–7.481 (m, 2 H), 7.392–7.124 (m, 9 H), 7.064 (d, 2 H, J=8 Hz), 3.794 (d, 1 H, J=13 Hz), 3.703 (d, 1 H, J=13 Hz), 3.162 (s, 2 H), 2.583–2.525 (m, 1 H), 2.233–2.124 (m, 3 H).

EXAMPLE 101

5,6-Dihydro-4-hydroxy-3-(3-methylphenylmethylthio)-6-phenyl-6-(2-phenylethyl)-2H-pyran-2-one (+/−).

The title compound was prepared as described in General Method 7 using the following: 5,6-dihydro-4-hydroxy-6-phenyl-(2-phenylethyl)-2H-pyran-2-one (0.250 g, 0.85 mmol), [(3-methylphen-1-yl)methyl]-p-toluenethiosulfonate (0.298 g, 1.02 mmol), Et₃N (0.25 mL, 1.81 mmol), absolute ethanol (5.0 mL), NaHCO₃ (0.5 g). The mixture was heated to 40° C. for 16 h, then diluted with diethyl ether (100 mL) and washed with H₂O. The solvent was then removed in vacuo and the residue submitted to column chromatography (SiO₂, 100% CH₂Cl₂ to 2% methanol in CH₂Cl₂) to provide a thick oil (0.242 g). $^1$H NMR (400 MHz, DMSO-d₆) δ 11.427 (bs, 1 H), 7.423–7.374 (m, 4 H), 7.330–7.288 (m, 1 H), 7.238 (t, 2 H, J=7 Hz), 7.145 (t, 1 H, J=8 Hz), 7.086–7.007 (m, 2 H), 6.952 (d, 2 H, J=6 Hz), 6.790 (d, 1 H, J=7 Hz), 3.630 (d, 1 H, J=12.5 Hz), 3.544 (d, 1 H, J=12.5 Hz), 3.227 (d, 1 H, J=17.5 Hz), 3.153 (d, 1 H, J=17.5 Hz), 2.567 (bt, 1 H, J=12 Hz), 2.244–2.132 (m, 3 H).

EXAMPLE 102

3-[4-Hydroxy-2-oxo-6-(2-phenylethyl) -6-phenyl-5, 6-dihydro-2H-pyran-3-ylthiomethyl]benzonitrile (+/−).

The title compound was prepared as described in General Method 7 using the following: 5,6-dihydro-4-hydroxy-6-phenyl-(2-phenylethyl)-2H-pyran-2-one (0.250 g, 0.85 mmol), [(3-cyanophen-1-yl)methyl]-p-toluenethiosulfonate (0.309 g, 1.02 mmol), Et₃N (0.25 mL, 1.81 mmol), absolute ethanol (5.0 mL), NaHCO₃ (0.5 g). The mixture was heated to 40° C. for 16 h, then diluted with diethyl ether (100 mL), and washed with H₂O. The solvent was then removed in vacuo and the residue submitted to column chromatography (SiO₂, 100% CH₂Cl₂ to 2% methanol in CH₂Cl₂) to provide a solid (0.242 g, m.p. 58°–60° C.). $^1$H NMR 400 MHz, DMSO-d₆) δ 11.572 (bs, 1 H), 7.585 (d, 1 H, J=7 Hz), 7.499 (s, 1 H), 7.426–7.078 (m, 10 H), 7.066 (d, 2 H, J=7 Hz), 3.736 (d, 1 H, J=13.5 Hz), 3.637 (d, 1 H, J=13.5 Hz), 3.185 (AB, 2 H, $J_{AB}$=17.5 Hz), 2.57–2.511 (m, 1 H), 2.207–1.074 (m, 3 H).

EXAMPLE 103

3-(2-Chlorophenylmethylthio)-5,6-dihydro-4-hydroxy-6,6-diphenyl-2H-pyran-2-one.

The title compound was prepared as described in General Method 7 using the following: 5,6-dihydro-4-hydroxy-6,6-diphenyl-2H-pyran-2-one (0.250 g, 0.94 mmol), [(2-chlorophen-1-yl)methyl]-p-toluenethiosulfonate (0.304 g, 1.10 mmol), Et₃N (0.26 mL, 1.9 mmol), absolute ethanol (5.0 mL), NaHCO₃ (0.5 g). The mixture was heated to 40° C. for 16 h then diluted with diethyl ether (100 mL), and washed with H₂O. The solvent was then removed in vacuo and the residue submitted to column chromatography (SiO₂, 100% CH₂Cl₂to 2% methanol in CH₂Cl₂) to provide a solid (0.123 g, m.p. 153°–155° C.). $^1$H NMR (400 MHz, DMSO-d₆) δ 7.415–7.271 (m, 11 H), 7.187 (td, 1 H, J=1.3 Hz, J=7

Hz), 7.047 (td, 1 H, J=1.3 Hz, J=7 Hz), 6.658 (dd, 1 H, J=1.5 Hz, J=7 Hz), 3.610 (s, 2 H), 3.582 (s, 2 H).

EXAMPLE 104

5,6-Dihydro-4-hydroxy-6-(3-methylbutyl)-6-phenyl-3-[(trifluoromethylphenyl)methylthiol]-2H-pyran-2-one (+/−).

The title compound was prepared as described in General Method 7 using the following: 5,6-dihydro-4-hydroxy-6-phenyl-6-(3-methylbutyl)-2H-pyran-2-one (0.250 g, 0.94 mmol), (3-trifluoromethylbenzyl)-p-toluenethiosulfonate (0.43 g, 1.24 mmol), Et$_3$N (0.17 mL, 1.24 mmol), absolute ethanol (5.0 mL), NaHCO$_3$ (0.5 g). The mixture was heated to 40° C. for 16 h, then diluted with diethyl ether (100 mL) and washed with H$_2$O. The solvent was then removed in vacuo and the residue submitted to column chromatography (SiO$_2$, 100% CH$_2$Cl$_2$ to 1.5% methanol in CH$_2$Cl$_2$) to provide a thick oil (0.364 g). $^1$H NMR (400 MHz, DMSO-d$_6$) δ 7.523–7.503 (m, 2 H), 7.318–7.232 (m, 6 H), 7.188 (d, 1 H, J=7.5 Hz), 3.781 (d, 1 H, J=13 Hz), 3.689 (d, 1 H, J=13 Hz), 3.076 (AB, 2 H, J$_{AB}$=14 Hz), 1.869–1.783 (m, 2 H), 1.380–1.314 (m, 1 H), 1.141–1.040 (m, 1 H), 0.828–0.727 (m, 7 H).

EXAMPLE 105

5,6-Dihydro-4-hydroxy-3-(methoxyphenylmethylthio)-6-(3-methylbutyl)-6-phenyl-2H-pyran-2-one (+/−).

The title compound was prepared as described in General Method 7 using the following: 5,6-dihydro-4-hydroxy-6-phenyl-6-(3-methylbutyl)-2H-pyran-2-one (0.250 g, 0.94 mmol), (3-methoxybenzyl)-p-toluenethiosulfonate (0.385 g, 1.24 mmol), Et$_3$N (0.17 mL, 1.24 mmol), absolute ethanol (3.0 mL), NaHCO$_3$ (0.5 g). The mixture was heated to 40° C. for 16 h, then diluted with diethyl ether (100 mL) and washed with H$_2$O. The solvent was then removed in vacuo and the residue submitted to column chromatography (SiO$_2$, 100% CH$_2$Cl$_2$ to 1.5% methanol in CH$_2$Cl$_2$) to provide a thick oil (0.364 g). $^1$H NMR (400 MHz, DMSO-d$_6$) δ 7.365–7.243 (m, 5 H), 7.071 (t, 1 H, J=8 Hz), 7.754–6.715 (m, 2 H), 6.562 (d, 1 H, J=7.5 Hz), 3.699 (s, 3 H), 3.651 (d, 1 H, J=12 Hz), 3.567 (d, 1 H, J=12 Hz), 3.098 (s, 2 H), 1.869–1.819 (m, 2 H), 1.387–1.321 (m, 1 H), 1.125–1.066 (m, 1 H), 0.809–0.702 (m, 7 H).

EXAMPLE 106

5,6-Dihydro-4-hydroxy-3-(3-methylphenylmethylthio)-6-(3-methylbutyl)-6-phenyl-2H-pyran-2-one (+/−).

The title compound was prepared as described in General Method 7 using the following: 5,6-dihydro-4-hydroxy-6-phenyl-6-(3-methylbutyl)-2H-pyran-2-one (0.250 g, 0.94 mmol), [(3-methylphen-1-yl)methyl]-p-toluenethiosulfonate (0.36 g, 1.24 mmol), Et$_3$N (0.17 mL, 1.24 mmol), absolute ethanol (3.0 mL), NaHCO$_3$ (0.5 g). The mixture was heated to 40° C. for 16 h, then diluted with diethyl ether (100 mL) and washed with H$_2$O. The solvent was then removed in vacuo and the residue submitted to column chromatography (SiO$_2$, 100% CH$_2$Cl$_2$ to 1.5% methanol in CH$_2$Cl$_2$) to provide a thick oil (0.290 g). $^1$H NMR (400 MHz, DMSO-d$_6$) δ 7.384–7.262 (m, 5 H), 7.054 (t, 1 H, J=7.5 Hz), 6.979 (d, 1 H, J=7.5 Hz), 6.937 (s, 1 H), 6.782 (d, 1 H, J=7.5 Hz), 3.609 (d, 1 H, J=12.5 Hz), 3.524 (d, 1 H, J=12.5 Hz), 3.108 (s, 2 H), 2.226 (s, 3 H), 1.902–1.803 (m, 2 H), 1.398–1.332 (m, 1 H), 1.149–1.059 (m, 1 H), 0.849–0.709 (m, 7 H).

EXAMPLE 107

3-(Benzo[1,3]dioxol-5-ylmethylthio)-5,6-dihydro-4-hydroxy-6-phenyl-6-(2-phenylethyl)-2H-pyran-2-one (+/−).

The title compound was prepared as described in General Method 7 using the following: 5,6-dihydro-4-hydroxy-6-phenyl-6-(2-phenylethyl)-2H-pyran-2-one (0.250 g, 0.85 mmol), benzo[1,3]dioxol-5-ylmethyl-p-toluenethiosulfonate (0.36 g, 1.02 mmol), Et$_3$N (0.25 mL, 1.81 mmol), absolute ethanol (3.0 mL), NaHCO$_3$, (0.5 g). The mixture was heated to 40° C. for 16 h then diluted with diethyl ether (100 mL), and washed with H$_2$O. The solvent was then removed in vacuo and the residue submitted to column chromatography (SiO$_2$, 100% CH$_2$Cl$_2$ to 1.5% methanol in CH$_2$Cl$_2$) to provide a solid (0.290 g, m.p. 53°–55° C.). $^1$H NMR (400 MHz, DMSO-d$_6$) δ 11.404 (bs, 1 H), 7.449–7.249 (m, 5 H), 7.239–7.216 (m, 2 H), 7.168–7.124 (m, 1 H), 7.077 (d, 2 H, J=7 Hz), 6.683 (d, 1 H, J=1.5 Hz), 6.607 (d, 1 H, J=8 Hz), 6.390 (dd, 1 H, J=1.5 Hz, J=8 Hz), 5.942 (d, 2 H, J=2 Hz), 3.600 (d, 1 H, J=13 Hz), 3.509 (d, 1 H, J=13 Hz), 3.195 (AB, 2 H, J$_{AB}$=17 Hz), 2.595–2.511 (m, 1 H), 2.244–2.094 (m, 3 H).

GENERAL METHOD 8

The desired compounds were prepared by adding the 5,6-dihydro-2H-pyran-2-one and dry dichloromethane to a reaction vessel followed by the addition of the acid chloride and Et$_3$N. The mixture was allowed to stir for 15 min. and then diluted with diethyl ether. The mixture was then washed with sat'd NaHCO$_3$ (2×) and the organic layer dried with MgSO$_4$. The solvent was then removed in vacuo, the residue redissolved in CH$_3$CN and then treated with Et$_3$N and acetone cyanohydrin. The mixture was allowed to stir for 18 h and then diluted with diethyl ether. The mixture was then washed with 1.0N HCl, dried with Na$_2$SO$_4$, and the solvent removed in vacuo. The residue was then dissolved in glacial acetic acid and treated with NaBH$_3$CN. The reaction was allowed to proceed for 30 min then treated with brine. The mixture was then extracted with ethyl acetate, the organic layers combined, dried with MgSo$_4$, and the solvent removed in vacuo.

EXAMPLE 108

5,6-Dihydro-4-hydroxy-6,6-diphenyl-3-phenylmethyl-2H-pyran-2-one.

The title compound was prepared as described in General Method 8 using the following: 5,6-dihydro-4-hydroxy-6,6-diphenyl-2H-pyran-2-one (0.250 g, 0.940 mmol), Et$_3$N (0.13 mL, 0.94 mmol), benzoyl chloride (0.109 mL, 0.94 mmol), CH$_2$Cl$_2$ (2.0 mL), acetonitrile (5.0 mL), acetone cyanohydrin (0.01 mL, 0.09 mmol), Et$_3$N (0.27 mL, 1.9 mmol), glacial acetic acid (10.0 mL), sodium cyanoborohydride (0.133 g, 2.11 mmol). Purification was achieved by submitting the final residue to column chromatograpy (SiO$_2$, 4/1 hexane/ethyl acetate to 3/2 hexane /ethyl acetate) to provide a solid (0.105 g, 63°–65° C.). $^1$H NMR (400 MHz, DMSO-d$_6$) δ 11.136 (s, 1 H), 7.501–7.280 (m, 11 H), 6.997–6.932 (m, 2 H), 6.566 (d, 2 H, J=7 Hz), 3.530 (s, 2 H), 3.432 (s, 2 H).

EXAMPLE 109

5,6-Dihydro-4-hydroxy-6-phenyl-6-(2-phenylethyl)-3-phenylmethyl-2H-pyran-2-one (+/−).

The title compound was prepared as described in General Method 8 using the following: 5,6-dihydro-4-hydroxy-6- phenyl-6-(2-phenylethyl)-2H-pyran-2-one (0.250 g, 0.850 mmol), Et$_3$N (0.26 mL, 1.94 mmol), benzoyl chloride (0.109 mL, 0.94 mmol), CH$_2$Cl$_2$ (2.0 mL), acetonitrile (5.0 mL), acetone cyanohydrin (0.04 mL, 0.43 mmol), Et$_3$N (0.26 mL, 1.9 mmol), glacial acetic acid (10.0 mL), sodium cyanoborohydride (0.151 g, 2.4 mmol). Purification was achieved by submitting the final residue to column chromatography (SiO$_2$, 100% CH$_2$Cl$_2$ to 2% MeOH in CH$_2$Cl$_2$) to provide a thick oil (0.384 g). $^1$H NMR (400 MHz, DMSO-d$_6$) δ 10.922 (bs, 1 H), 7.395–7.315 (m, 5 H), 7.297–7.126 (m, 3 H), 7.084–7.028 (m, 5 H), 6.775–6.611 (m, 2 H), 3.423 (s, 2 H), 3.248 (d, 1 H, J=17 Hz), 3.175 (d, 1 H, J=17 Hz), 2.619–2.551 (m, 1 H), 2.292–2.227 (m, 3 H).

EXAMPLE 110

5,6-Dihydro-4-hydroxy-3-[ (2-methylphenyl)methyl]-6-phenyl-6-(2-phenylethyl)-2H-pyran-2-one (+/−).

The title compound was prepared as described in General Method 8 using the following: 5,6-dihydro-4-hydroxy-6-phenyl-6-(2-phenylethyl)-2H-pyran-2-one (0.250 g, 0.850 mmol), Et$_3$N (0.12 mL, 0.85 mmol), 2-methylbenzoyl chloride (0.11 mL, 0.85 mmol), CH$_2$Cl$_2$ (5.0 mL), acetonitrile (4.0 mL), acetone cyanohydrin (0.04 mL, 0.43 mmol), Et$_3$N (0.24 mL, 1.7 mmol), glacial acetic acid (10.0 mL), sodium cyanoborohydride (0.151 g, 2.4 mmol). Purification was achieved by submitting the final residue to column chromatograpy (SiO$_2$, 100% CH$_2$Cl$_2$ to 2% MeOH in CH$_2$Cl$_2$) to provide a solid (0.195 g, m.p. 109°–111° C.). $^1$H NMR (400 MHz, DMSO-d$_6$) δ 10.886 (bs, 1 H), 7.457–7.359 (m, 5 H), 7.242 (t, 2 H, J=7 Hz), 7.169–7.130 (m, 1 H), 7.097 (d, 2 H, J=7.5 Hz), 7.001 (d, 1 H, J=7.5 Hz), 6.937 (t, 1 H, J=7.5 Hz), 6.695 (t, 1 H, J=7 Hz), 6.215 (d, 1 H, J=7.5 Hz), 3.292 (d, 1 H, J=17 Hz), 3.169 (d, 1 H, J=17 Hz), 2.643–2.584 (m, 1 H), 2.50–2.475 (2 H+solvent) 2.296–2.182 (m, 3 H), 2.125 (s, 3 H).

EXAMPLE 111

5,6-Dihydro-4-hydroxy-3-[(3-methylphenyl)methyl]-6-phenyl-6-(2-phenylethyl)-2H-pyran-2-one (+/−).

The title compound was prepared as described in General Method 8 using the following: 5,6-dihydro-4-hydroxy-6-phenyl-6-(2-phenylethyl)-2H-pyran-2-one (0.250 g, 0.850 mmol), Et$_3$N (0.12 mL, 0.85 mmol), 3-methylbenzoyl chloride (0.12 mL, 0.89 mmol), CH$_2$Cl$_2$ (3.0 mL), acetonitrile (5.0 mL), acetone cyanohydrin (0.037 mL, 0.40 mmol), Et$_3$N (0.24 mL, 1.8 mmol), glacial acetic acid (5.0 mL), sodium cyanoborohydride (0.16 g, 2.6 mmol). Purification was achieved by submitting the final residue to column chromatograpy (SiO$_2$, 100% CH$_2$Cl$_2$ to 2% MeOH in CH$_2$Cl$_2$) to provide a solid (0.250 g, m.p. 53°–55° C.). $^1$H NMR (400 MHz, DMSO-d$_6$) δ 10.884 (bs, 1 H), 7.418–7.310 (m, 5 H), 7.231 (t, 2 H, J=7.5 Hz), 7.148–7.122 (m, 1 H), 7.071 (d, 2 H, J=7 Hz), 6.929 (t, 1 H, J=7.5 Hz), 6.843 (d, 1 H, J=7.5 Hz), 6.587 (d, 1 H, J=7.5 Hz), 6.545 (s, 1 H), 3.398 (AB, 2 H, JAB =15.5 Hz), 3.248 (d, 1 H, J=17 Hz), 3.125 (d, 1 H, J=17 Hz), 2.607–2.511 (m, 1 H), 2.338–2.159 (m, 3 H), 2.094 (s, 3 H).

EXAMPLE 112

5,6-Dihydro-4-hydroxy-3-[(3-methylphenyl)methyl]-6,6-diphenyl-2H-pyran-2-one.

The title compound was prepared as described in General Method 8 using the following: 5,6-dihydro-4-hydroxy-6,6-diphenyl-2H-pyran-2-one (0.300 g, 1.13 mmol), Et$_3$N 0.16 mL, 1.15 mmol), 3-methylbenzoyl chloride (0.15 mL, 1.13 mmol), CH$_2$Cl$_2$ (4.0 mL), acetonitrile (4.0 mL), acetone cyanohydrin (0.05 mL, 0.58 mmol), Et$_3$N (0.32 mL, 2.3 mmol), glacial acetic acid (4.0 mL), sodium cyanoborohydride (0.28 g, 4.5 mmol). Purification was achieved by submitting the final residue to column chromatography (SiO$_2$, 100% CH$_2$Cl$_2$ to 1% MeOH in CH$_2$Cl$_2$) to provide a solid (0.223 g, m.p. 57°–59° C.). $^1$H NMR (400 MHz, DMSO-d$_6$) δ 11.112 (bs, 1 H), 7.414–7.270 (m, 10 H), 6.875–6.812 (m, 2 H), 6.429–6.392 (m, 2 H), 3.527 (s, 2 H), 3.409 (s, 2 H), 2.060 (s, 3 H).

EXAMPLE 113

5,6-Dihydro-4-hydroxy-3-[(2-methylphenyl)methyl]-6,6-diphenyl-2H-pyran-2-one.

The title compound was prepared as described in General Method 8 using the following: 5,6-dihydro-4-hydroxy-6,6-diphenyl-2H-pyran-2-one (0.300 g, 1.13 mmol), Et$_3$N (0.16 mL, 1.15 mmol), 2-methylbenzoyl chloride (0.15 mL, 1.13 mmol), CH$_2$Cl$_2$ (4.0 mL), acetonitrile (4.0 mL), acetone cyanohydrin (0.05 mL, 0.58 mmol), Et$_3$N (0.32 mL, 2.3 mmol), glacial acetic acid (4.0 mL), sodium cyanoborohydride (0.28 g, 4.5 mmol). Purification was achieved by submitting the final residue to column chromatography (SiO$_2$, 100% CH$_2$Cl$_2$ to 1% MeOH in CH$_2$Cl$_2$) to provide a solid (0.135 g, m.p. 169°–171° C.). $^1$H NMR (400 MHz, DMSO-d$_6$) δ 11.102 (bs, 1 H), 7.444–7.260 (m, 10 H), 6.981 (d, 1 H, J=7.5 Hz), 6.900 (t, 1 H, J=7.5 Hz), 6.577 (t, 1 H, J=7 Hz), 5.897 (d, 1 H, J=7.5 Hz), 3.557 (s, 2 H), 3.341 (s, 2 H), 2.115 (s, 3 H).

EXAMPLE 114

5,6-Dihydro-4-hydroxy-6-phenyl-6-(2-phenylethyl)-3-[(2-trifluoromethylphenyl)methyl]-2H-pyran-2-one.

The title compound was prepared as described in General Method 8 using the following: 5,6-dihydro-4-hydroxy-6-phenyl-6-(2-phenylethyl)-2H-pyran-2-one (0.300 g, 1.02 mmol), Et$_3$N (0.15 mL, 1.1 mmol), 2-trifluoromethylbenzoyl chloride (0.21 mL, 1.02 mmol), CH$_2$Cl$_2$ (4.0 mL), acetonitrile (4.0 mL), acetone cyanohydrin (0.04 mL, 0.47 mmol), Et$_3$N (0.29 mL, 2,1 mmol), glacial acetic acid (3.0 mL), sodium cyanoborohydride (0.20 g, 3.1 mmol). Purification was achieved by submitting the final residue to column chromatography (SiO$_2$, 100% CH$_2$Cl$_2$ to 1% MeOH in CH$_2$Cl$_2$) to provide an oil (0.102 g). $^1$H NMR (400 MHz, DMSO-d$_6$) δ 11.21 (bs, 1 H), 7.584 (d, 1 H, J=8 Hz), 7.457–7.030 (m, 12 H), 6.179 (d, 1 H, J=7.5 Hz), 3.594 (s, 2 H), 3.362 (d, 1 H, J=17 Hz), 3.249 (d, 1 H, J=17 Hz), 2.686–2.603 (m, 1 H), 2.374–2.182 (m, 3 H).

EXAMPLE 115

5,6-Dihydro-4-hydroxy-3-[(2-isopropylphenyl)methyl]-6,6-diphenyl-2H-pyran-2-one.

The title compound was prepared as described in General Method 8 using the following: 5,6-dihydro-4-hydroxy-6,6-diphenyl-2H-pyran-2-one (0.300 g, 1.15 mmol), Et$_3$N (0.17 mL, 1.2 mmol), 2-isopropylbenzoyl chloride (1.02 mmol), CH$_2$Cl$_2$ (4.0 mL), acetonitrile (4.0 mL), acetone cyanohydrin (0.05 mL, 0.5 mmol), Et$_3$N (0.35 mL, 2.5 mmol), glacial acetic acid (5.0 mL), sodium cyanoborohydride (0.50 g, 8.5 mmol). Purification was achieved by submitting the final residue to column chromatography (SiO$_2$, 100% CH$_2$Cl$_2$ to 1% MeOH in CH$_2$Cl$_2$) to provide a solid (0.128 g, 224°–226° C.). $^1$H NMR (400 MHz, DMSO-d$_6$) δ 11.180 (bs, 1 H), 7.445–7.235 (m, 10 H), 7.109 (d, 1 H, J=7.5 Hz), 6.970 (t, 1 H, J =7.5 Hz), 6.515 (t, 1 H, J=7.5 Hz), 5.841 (d, 1 H, J=7.5 Hz), 3.560 (s, 2 H), 3.463 (s, 2 H), 1.174–1.094 (m, 7 H).

EXAMPLE 116

5,6-Dihydro-4-hydroxy-6-(3-methylbutyl)-3-[(3-methylphenyl)methyl]-6-phenyl-2H-pyran-2-one (+/−).

The title compound was prepared as described in General Method 8 using the following: 5,6-dihydro-4-hydroxy-6-phenyl-6-(3-methylbutyl)-2H-pyran-2-one (0.300 g, 1.15 mmol), Et$_3$N (0.17 mL, 1.2 mmol), 3-methylbenzoyl chloride (0.15 mL, 1.15 mmol), CH$_2$Cl$_2$ (4.0 mL), acetonitrile (4.0 mL), acetone cyanohydrin (0.05 mL, 0.5 mmol), Et$_3$N (0.35 mL, 2.5 mmol), glacial acetic acid (4.0 mL), sodium cyanoborohydride (0.51 g, 8.1 mmol). Purification was achieved by submitting the final residue to column chromatograpy (SiO$_2$, 100% CH$_2$Cl$_2$ to 0.5% MeOH in CH$_2$Cl$_2$) to provide a solid (0.252 g, 53°–55° C.). $^1$H NMR (400 MHz, DMSO-d$_6$) δ 7.376–7.244 (m, 5 H), 6.915 (t, 1 H, J=7.5 Hz), 6.831 (d, 1 H, J=7.5 Hz), 6.549 (d, 1 H, J=7.5 Hz), 6.509 (s, 1 H), 3.369 (AB, 2 H, J$_{AB}$=14.4 Hz), 3.112 (AB, 2 H, J$_{AB}$=17.5 Hz), 2.088 (s, 3 H), 1.962 (m, 2 H), 1.416–1.333 (m, 1 H), 1.152–1.061 (m, 1 H), 0.898–0.726 (m, 7 H).

EXAMPLE 117

5,6-Dihydro-4-hydroxy-6-(3-methylbutyl)-6-phenyl-3-phenylmethyl-2H-pyran-2-one (+/−).

The title compound was prepared as described in General Method 8 using the following: 5,6-dihydro-4-hydroxy-6-(3-methylbutyl)-6-phenyl-2H-pyran-2-one (0.300 g, 1.15 mmol), Et$_3$N (0.17 mL, 1.2 mmol), benzoyl chloride (0.13 mL, 1.15 mmol), CH$_2$Cl$_2$ (4.0 mL), acetonitrile (4.0 mL), acetone cyanohydrin (0.05 mL, 0.5 mmol), Et$_3$N (0.35 mL, 2.5 mmol), glacial acetic acid (4.0 mL), sodium cyanoborohydride (0.51 g, 8.1 mmol). Purification was achieved by submitting the final residue to column chromatograpy (SiO$_2$, 100% CH$_2$Cl$_2$ to 1% MeOH in CH$_2$Cl$_2$) to provide a solid (0.215 g, 46°–48° C.). $^1$H NMR (400 MHz, DMSO-d$_6$) δ 10.864 (bs, 1 H), 7.375–7.248 (m, 7 H), 7.026–7.000 (m, 2 H), 6.737–6.713 (m, 1 H), 3.393–3.332 (2 H, obscured by solvent), 3.110 (AB, 2 H, J$_{AB}$=17 Hz), 1.933–1.870 (m, 2 H), 1.402–1.353 (m, 1 H), 1.132–1.084 (m, 1 H), 0.891–0.710 (m, 7 H).

EXAMPLE 118

5,6-Dihydro-4-hydroxy-6-(3-methylbutyl)-3-[(2-methylphenyl) methyl]-6-phenyl-2H-pyran-2-one (+/−).

The title compound was prepared as described in General Method 8 using the following: 5,6-dihydro-4-hydroxy-(3-methylbutyl)-6-phenyl-2H-pyran-2-one (0.300 g, 1.15 mmol), Et$_3$N (0.17 mL, 1.2 mmol), 2-methylbenzoyl chloride (0.15 mL, 1.15 mmol), CH$_2$Cl$_2$ (4.0 mL), acetonitrile (4.0 mL), acetone cyanohydrin (0.05 mL, 0.5 mmol), Et$_3$N (0.35 mL, 2.5 mmol), glacial acetic acid (4.0 mL), sodium cyanoborohydride (0.51 g, 8.1 mmol). Purification was achieved by submitting the final residue to column chro-matograpy (SiO$_2$, 100% CH$_2$Cl$_2$ to 1% MeOH in CH$_2$Cl$_2$) to provide a solid (0.215 g, 46°–48° C.). $^1$H NMR (400 MHz, DMSO-d$_6$) δ 10.829 (bs, 1 H), 7.395–7.303 (m, 5 H), 6.994 (d, 1 H, J=7 Hz), 6.927 (t, 1 H, J=7 Hz), 6.674 (t, 1 H, J =7 Hz), 6.149 (d, 1 H, J=7 Hz), 3.305 (AB, 2 H, J$_{AB}$=17 Hz), 3.158 (AB, 2 H, J$_{AB}$=17.5 Hz), 2.115 (s, 3 H), 1.988–1.854 (m, 2 H), 1.439–1.356 (m, 1 H), 1.177–1.087 (m, 1 H), 0.943–0.852 (m, 1 H), 0.792–0.767 (m, 6 H).

EXAMPLE 119

5,6-Dihydro-4-hydroxy-3-[(3-methoxyphenyl) methyl]-6-phenyl-6-(2-phenylethyl)-2H-pyran-2-one (+/−).

The title compound was prepared as described in General Method 8 using the following: 5,6-dihydro-4-hydroxy-6-phenyl-6-(2-phenylethyl)-2H-pyran-2-one (0.300 g, 1.02 mmol), Et$_3$N (0.15 mL, 1.1 mmol), 2-methoxybenzoyl chloride (0.17 g, 1.02 mmol), CH$_2$Cl$_2$ (4.0 mL), acetonitrile (4.0 mL), acetone cyanohydrin (0.05 mL, 0.5 mmol), Et$_3$N (0.35 mL, 2.5 mmol), glacial acetic acid (5.0 mL), sodium cyanoborohydride (0.47 g, 7.5 mmol).

Purification was achieved by submitting the final residue to column chromatography (SiO$_2$, 100% CH$_2$Cl$_2$ to 1% MeOH in CH$_2$Cl$_2$) to provide a solid (0.227 g, 62°–64° C.). $^1$H NMR (400 MHz, DMSO-d$_6$) δ 10.823 (bs, 1 H), 7.436–7.362 (m, 5 H), 7.265 (t, 2 H, 7.176–7.098 (m, 3 H), 7.022 (td, 1 H, J=1 Hz, J=8 Hz), 6.815 (d, 1 H, J=7.5 Hz), 6.400 (td, 1 H, J=1 Hz, J=7.5 Hz), 5.952 (dd, 1 H, J=1 Hz, J=7 Hz), 3.716 (S, 3 H), 3.391–3.169 (m, 4 H), 2.650–2.582 (m, 1 H), 2.354–2.182 (m, 3 H).

EXAMPLE 120

5,6-Dihydro-4-hydroxy-3-[ (naphthalen-1-yl) methyl]-6,6-diphenyl-2H-pyran-2-one.

The title compound was prepared as described in General Method 8 using the following: 5,6-dihydro-4-hydroxy-6,6-diphenyl-2H-pyran-2-one (0.300 g, 1.13 mmol), Et$_3$N (0.160 mL, 1.15 mmol), l-naphthoyl chloride (1.13 mmol), CH$_2$Cl$_2$ (6.0 mL), acetonitrile (4.0 mL), acetone cyanohydrin (0.05 mL, 0.5 mmol), Et$_3$N (0.35 mL, 2.5 mmol), glacial acetic acid (6.0 mL), sodium cyanoborohydride (0.50 g, 7.9 mmol). Purification was achieved by submitting the final residue to column chromatograpy (SiO$_2$, 100% CH$_2$Cl$_2$ to 1.5% MeOH in CH$_2$Cl$_2$) to provide a solid (0.120 g, 203°–205° C.(dec.)). $^1$H NMR (400 MHz, DMSO-d$_6$) δ 11.223 (bs, 1 H), 8.057 (d, 1 H, J=7 Hz), 7.855–7.821 (m, 1 H), 7.603 (d, 1 H, J=8 Hz), 7.514–7.302 (m, 12 H), 6.866 (dd, 1 H, J=6.5 Hz, J=8 Hz), 5.975 (d, 1 H, J=7 Hz), 3.874 (s, 2 H), 3.621 (s, 2 H).

EXAMPLE 121

5,6-Dihydro-4-hydroxy-3-[(2-isopropylphenyl) methyl]-6-(3-methylbutyl)-6-phenyl-2H-pyran-2-one (+/−).

The title compound was prepared as described in General Method 8 using the following: 5,6-dihydro-4-hydroxy-6-(3-methylbutyl)-6-phenyl-2H-pyran-2-one (0.300 g, 1.15 mmol), Et$_3$N (0.17 mL, 1.2 mmol), 2-isopropylbenzoyl chloride (1.15 mmol), CH$_2$Cl$_2$ (4.0 mL), acetonitrile (4.0 mL), acetone cyanohydrin (0.05 mL, 0.5 mmol), Et$_3$N (0.35 mL, 2.5 mmol), glacial acetic acid (5.0 mL), sodium cyanoborohydride (0.50 g, 8.1 mmol). Purification was achieved by submitting the final residue to column chromatograpy (SiO$_2$, 100% CH$_2$Cl$_2$) to provide a solid (0.118 g, 124°–126° C.). $^1$H NMR (400 MHz, DMSO-d$_6$) δ 10.855 (bs, 1 H), 7.395–7.306 (m, 5 H), 7.115 (dd, 1 H, J=1 Hz, J=7.5 Hz), 6.991 (t, 1 H, J=7 Hz), 6.622 (td, I H, J=1 Hz, J=7 Hz), 6.123 (d, 1 H, J=7 Hz), 3.422 (s, 2 H), 3.210–3.102 (m, 3 H), 1.975–1.871 (m, 2 H), 1.437–1.371 (m, 1 H), 1.142–1.084 (m, 7 H), 0.938–0.807 (m, 1 H), 0.791–0.766 (m, 6 H).

EXAMPLE 122

5,6-Dihydro-4-hydroxy-3-[(2-isopropylphenyl) methyl])-6-phenyl-6-(2-phenylethyl)-2H-pyran-2-one (+/−).

The title compound was prepared as described in General Method 8 using the following: 5,6-dihydro-4-hydroxy-6-phenyl-6-(2-phenylethyl)-2H-pyran-2-one (0.300 g, 1.02 mmol), Et$_3$N (0.17 mL, 1.2 mmol), 2-isopropylbenzoyl chloride (1.02 mmol), CH$_2$Cl$_2$ (4.0 mL), acetonitrile (4.0 mL), acetone cyanohydrin (0.05 mL, 0.5 mmol), Et$_3$N (0.35 mL, 2.5 mmol), glacial acetic acid (4.0 mL), sodium cyanoborohydride (0.45 g, 7.1 mmol). Purification was achieved by submitting the final residue to column chromatograpy (SiO$_2$, 100% CH$_2$Cl$_2$) to provide a solid (0.130 g, 73 °–74° C.). $^1$H NMR (400 MHz, DMSO-d$_6$) δ 7.424–7.328 (m, 6 H), 7.259–7.222 (m, 2 H), 7.197–7.082 (m, 3 H), 6.996 (t, 1 H, J=7 Hz), 6.638 (td, 1 H, J=1.5 Hz, J=8 Hz), 6.195 (d, 1 H, J=7 Hz), 3.440 (s, 2 H), 3.268–3.133 (m, 2 H), 2.630–2.528 (m, 1 H), 2.332–2.147 (m, 3 H), 2.332–2.147 (m, 7 H).

EXAMPLE 123

3-[(2-Chlorophenyl)methyl]-5,6-dihydro-4-hydroxy-6-(3-methylbutyl)-6-phenyl-2H-pyran-2-one (+/−).

The title compound was prepared as described in General Method 8 using the following: 5,6-dihydro-4-hydroxy-6-(3-methylbutyl)-6-phenyl-2H-pyran-2-one (0.300 g, 1.15 mmol), Et$_3$N (0.17 mL, 1.2 mmol), 2-chlorobenzoyl chloride (0.15 mL, 1.15 mmol), CH$_2$Cl$_2$ (4.0 mL), acetonitrile (4.0 mL), acetone cyanohydrin (0.05 mL, 0.5 mmol), Et$_3$N (0.35 mL, 2.5 mmol), glacial acetic acid (4.0 mL), sodium cyanoborohydride (0.720 g, 11.5 mmol). Purification was achieved by submitting the final residue to column chromatograpy (SiO$_2$, 100% CH$_2$Cl$_2$) to provide a solid (0.165 g, 51°–53° C.). $^1$H NMR (400 MHz, DMSO-d$_6$) δ 11.062 (bs, 1 H), 7.425–7.275 (m, 6 H), 7.072 (td, 1 H, J=1.5 Hz, J=7.5 Hz), 6.774 ( td, 1 H, J=1.2 Hz, J=7.5 Hz), 6.059 (dd, 1 H, J=1.2 Hz, J=7.5 Hz), 3.428 (AB, 2 H, J$_{AB}$=16.5 Hz), 3.191 (AB, 2 H, JAB=17 Hz), 1.964–1.884 (m, 2 H), 1.450–1.384 (m, 1 H), 1.163–1.118 (m, 1 H), 0.951 (m, 1 H), 0.802–0.776 (m, 6 H).

EXAMPLE 124

3-[(2-Chlorophenyl)methyl]-5,6-dihydro-4-hydroxy-6,6-diphenyl-2H- pyran-2-one (+/−).

The title compound was prepared as described in General Method 8 using the following: 5,6-dihydro-4-hydroxy-6,6-diphenyl-2H-pyran-2-one (0.300 g, 1.13 mmol), Et$_3$N (0.17 mL, 1.2 mmol), 2-chlorobenzoyl chloride (0.14 mL, 1.15 mmol), CH$_2$Cl$_2$ (4.0 mL), acetonitrile (4.0 mL), acetone cyanohydrin (0.05 mL, 0.5 mmol), Et$_3$N (0.35 mL, 2.5 mmol), glacial acetic acid (4.0 mL), sodium cyanoborohydride (0.50 g, 7.9 mmol). Purification was achieved by submitting the final residue to column chromatograpy (SiO$_2$, 100% CH$_2$Cl$_2$ to 0.5% MeOH in CH$_2$Cl$_2$) to provide a solid (0.130 g, 185°–187° C.). $^1$H NMR (400 MHz, DMSO-d$_6$) δ 11.351 (bs, 1 H), 7.464–7.282 (m, 11 H), 7.054 (t, 1 H, J=7 Hz), 6.679 (td, 1 H, J=1 Hz, J=7.5 Hz), 5.797 (d, 1 H, J=7 Hz), 3.586 (s, 2 H), 3.472 (s, 2 H).

EXAMPLE 125

6-Cyclopentylmethyl-5,6-dihydro-4-hydroxy-6-phenyl-3-phenylmethyl -2H-pyran-2-one (+/−).

The title compound was prepared as described in General Method 8 using the following: 6-cyclopentylmethyl-5,6-dihydro-4-hydroxy-6-phenyl-2H-pyran-2-one (0.300 g, 1.10 mmol), Et$_3$N (0.17 mL, 1.2 mmol), benzoyl chloride (0.13 mL, 1.10 mmol), CH$_2$Cl$_2$ (4.0 mL), acetonitrile (4.0 mL), acetone cyanohydrin (0.05 mL, 0.5 mmol), Et$_3$N (0.35 mL, 2.5 mmol), glacial acetic acid (4.0 mL), sodium cyanoborohydride (0.50 g, 7.9 mmol). Purification was achieved by submitting the final residue to column chromatograpy (SiO$_2$, 100% CH$_2$Cl$_2$) to provide a solid (0.188 g, 53°–55° C.). $^1$H NMR (400 MHz, DMSO-d$_6$) δ 10.849 (bs, 1 H), 7.371–7.284 (m, 5 H), 7.040–7.004 (m, 3 H), 6.747–6.724 (m, 2 H), 3.395 (s, 2 H), 3.117 (AB, 2 H, JAB=17.5 Hz), 2.059–1.950 (m, 2 H), 1.652–1.578 (m, 2 H), 1.561–1.289 (m, 5 H), 1.021–0.844 (m, 2 H).

EXAMPLE 126

5,6-Dihydro-4-hydroxy-6-pentyl-6-phenyl-3-phenylmethyl-2H-pyran-2-one (+/−).

The title compound was prepared as described in General Method 8 using the following: 5,6-dihydro-4-hydroxy-6-n-pentyl-6-phenyl-2H-pyran-2-one (0.300 g, 1.15 mmol), Et$_3$N (0.17 mL, 1.2 mmol), benzoyl chloride (0.13 mL, 1.15 mmol), CH$_2$Cl$_2$ (4.0 mL), acetonitrile (4.0 mL), acetone cyanohydrin (0.05 mL, 0.5 mmol), Et$_3$N (0.35 mL, 2.5 mmol), glacial acetic acid (4.0 mL), sodium cyanoborohydride (0.50 g, 7.9 mmol). Purification was achieved by submitting the final residue to column chromatograpy (SiO$_2$, 100% CH$_2$Cl$_2$) to provide an oil (0.215 g). $^1$H NMR (400 MHz, DMSO-d6) δ 10.850 (bs, 1 H), 7.367–7.287 (m, 5 H), 7.018–7.002 (m, 3 H), 6.724–6.700 (m, 2 H), 3.380 (AB, 2 H, J$_{AB}$=14 Hz), 3.096 (AB, 2 H, J$_{AB}$=17 Hz), 1.950–1.820 (m, 2 H), 1.230–1.100 (m, 5 H), 1.080–0.920 (in, 1 H), 0.775 (t, 3 H, J=7 Hz).

EXAMPLE 127

3-[(3-Chloromethylphenyl)methyl]-5,6-dihydro-4-hydroxy-6,6-diphenyl-2H-pyran-2-one.

The title compound was prepared as described in General Method 8 using the following: 5,6-dihydro-4-hydroxy-6,6-diphenyl-2H-pyran-2-one (0.300 g, 1.13 mmol), Et$_3$N (0.17 mL, 1.2 mmol), 3-(chloromethyl)benzoyl chloride (0.13 mL, 1.13 mmol), CH$_2$Cl$_2$ (5.0 mL), acetonitrile (5.0 mL), acetone cyanohydrin (0.05 mL, 0.5 mmol), Et$_3$N (0.35 mL, 2.5 mmol), glacial acetic acid (6.0 mL), sodium cyanoborohydride (0.50 g, 7.9 mmol). Purification was achieved by submitting the final residue to column chromatograpy (SiO$_2$, 4/1 hexane/ethyl acetate to 3/2 hexane/ethyl acetate) to provide a solid (0.118 g, 135°–137° .C). $^1$H NMR (400 MHz, DMSO-d$_6$) δ 11.211 (s, 1 H), 7.418–7.280 (m, 10 H), 7.088 (d, 1 H, 7.5 Hz), 6.975 (t, 1 H, J=7.5 Hz), 6.689 (s, 1 H), 6.513 (d, 1 H, J=7.5 Hz), 4.498 (s, 2 H), 3.540 (s, 2 H), 3.447 (s, 2 H).

EXAMPLE 128

5,6-Dihydro-3-(benzoylcarbonyl)-4-hydroxy-6,6-diphenyl-2H-pyran-2-one.

The desired compounds were prepared by adding 5,6-dihydro-4-hydroxy-6,6-diphenyl-2H-pyran-2-one (0.500 g, 1.88 mmol) and dry dichloromethane (10.0 mL) to a reaction vessel followed by the addition of the benzoyl chloride (0.22 mL, 1.88 mmol) and Et$_3$N (0.28 mL, 2.0 mmol). The mixture was allowed to stir for 15 min. and then diluted with diethyl ether. The mixture was then washed with sat'd NaHCO$_3$ (2×) and the organic layer dried with MgSO$_4$. The solvent was then removed in vacuo, the residue redissolved in CH$_3$CN and then treated with Et$_3$N (0.56 mL, 4.0 mmol) and acetone cyanohydrin. The mixture was allowed to stir for 18 h and then diluted with diethyl ether. The mixture was then washed with 1.0N HCl, dried with NaSO$_4$, and the solvent removed in vacuo. Purification was achieved by submitting the final residue to column chromatograpy (SiO$_2$, 3/2 hexane/ethyl acetate) to provide a solid (0.357 g, 66°–68° C.). $^1$H NMR (400 MHz, CDCl$_3$) δ 7.495–7.208 (m, 15 H), 3.558 (s, 2 H).

EXAMPLE 129

5,6-Dihydro-4-hydroxy-6,6-dipentyl-3-phenylmethylthio-2H-pyran-2-one.

The title compound was prepared as described in General Method 4 to provide an oil. $^1$H NMR (400 MHz, CDCl$_3$) δ 7.3–7.14 (m, 5 H), 3.8 (s, 2 H), 2.54 (s, 2 H), 1.5–1.35 (m, 4 H), 1.26–1.11 (m, 12 H), 0.87–0.80 (t, 6 H).

EXAMPLE 130

5,6-Dihydro-4-hydroxy-6-phenyl-3-[(2-isopropyl-5-methylphenyl)thio]-2(1H)-pyridinone (±).

The title compound was prepared as described in General Method III using 95.6 mg of 5,6-dihydro-4-hydroxy-6-phenyl-2(1H)-pyridinone, 180 mg of toluene-4-thiosulfonic acid S-(2-isopropyl-5-methylphenyl) ester (prepared as per Ranasinghe and Fuchs, *Synthetic Communications* 18: 227 (1988)) and 0.08 ml of triethylamine in 5 ml of absolute ethanol. The solution was stirred overnight at room temperature. Purification by flash chromatography using CH$_2$Cl$_2$/isopropanol (99/1 to 95/5) as eluent gave a solid (m.p. 184°–186° C). $^1$H NMR (CDCl$_3$) δ 1.28 (d, 3 H), 1.29 (d, 3 H), 2.23 (s, 3 H), 2.98 (d, 2 H), 3.52 (qn, 1 H), 4.85 (t, 1 H), 5.63 (s, 1 H), 6.78 (s, 1 H), 6.96 (m, 1 H), 7.14 (d, 1 H), 7.35–7.44 (m, 5 H), 7.55 (s, 1 H).

EXAMPLE 131

4-Hydroxy-3-[(1-isopropyl-4,4-dimethyl-4,5-dihydro-1H-imidazol-2-yl) thio]-6-phenyl-5,6-dihydro-2H-pyran-2-one.

The desired compounds were prepared by adding 4-hydroxy-6,6-diphenyl-5,6-dihydro-2H-pyran-2-one (0.250 g, 0.85 mmol) and dry t-butanol (4.5 mL) to a reaction vessel followed by the addition of n-bromosuccinimide (0.151 g, 0.850 mmol). The mixture was allowed to stir for 1 h in the dark and the solvent then removed in vacuo. The residue was then dissolved in CH$_2$Cl$_2$ and the mixture washed with H$_2$O. The organic layer was then dried with Na$_2$SO$_4$ and the solvent removed in vacuo. The resulting residue was then redissolved in CH$_2$Cl$_2$ (6.0 mL) and treated with 1-isopropylimidazolidine-2-thione (0.184 g, 1.28 mmol, prepared by the method described by A. F. McKay et al., *J. Am. Chem. Soc.*, 78: 1618 (1956))) followed by piperidine (0.084 mL, 0.85 mmol). The mixture was allowed to stir for 14 h in the dark then diluted with additional CH$_2$Cl$_2$ and the mixture washed with H$_2$O. The organic layer was then dried with Na$_2$SO$_4$ and the solvent removed in vacuo. the resulting solid was then submitted to column chromatography (SiO$_2$, 1/1 CH$_2$Cl$_2$/ethyl acetate to 14 /4 /1 CH$_2$Cl$_2$ /ethyl acetate /methanol) to provide a solid which was redissolved in CH$_2$Cl$_2$, filtered through a fiberglass filter, and the solvent removed in vacuo to provide the title compound (0.234 g, m.p. 160°–162° C. (dec.)). $^1$H NMR (400 MHz, DMSO-d$_6$) δ 7.732 (s, 1 H), 7.420–7.336 (m, 4 H), 7.277–7.212 (m, 3 H), 7.137 (t, 1 H, J=7 Hz), 7.080–7.060 (m, 2 H), 3.970–3.904 (m, 1 H), 3.842 (t, 2 H, J=10 Hz), 3.602–3.517 (m, 2 H), 2.925 (AB, 2 H, JAB=16 Hz), 2.617–2.540 (m, 1 H), 2.315–2.240 (m, 1 H), 2.160–2.025 (m, 2 H), 1.206–1.180 (m, 6 H).

EXAMPLE 132

4-Hydroxy-3-[(1-isopropyl-1,4,5,6-tetrahydro-pyrimidine-2-yl)thio]-6-phenyl-5,6-dihydro-2H-pyran-2-one.

The title compound was prepared as described in example 41 using the following: 5,6-dihydro-4-hydroxy-6-phenyl-6-(2-phenylethyl)-2H-pyran-2-one (0.250 g, 0.850 mmol), t-butanol (3.5 mL), n-bromosuccinimide (0.151 g, 0.85 mmol), CH$_2$Cl$_2$ (6.0 mL), 1-isopropyltetrahydropyrimidine-2-thione (0.270 g, 1.70 mmol, prepared by the method described by A. F. McKay et al., *J. Am. Chem. Soc.*, 78: 1618 (1956)), piperidine (0.084 mL, 0.85 mmol). Purification was achieved by submitting the final residue to column chromatograpy (SiO$_2$, 1/1 CH$_2$Cl$_2$/ethyl acetate to 2/14/1 ethyl acetate/CH$_2$Cl$_2$/methanol) to provide a solid which was redissolved in CH$_2$Cl$_2$, filtered through a fiberglass filter, and the solvent removed in vacuo to provide the title compound (0.356 g, m.p. 103°–105° C). $^1$H NMR (400 MHz, DMSO-d$_6$) δ 7.440–7.371 (m, 4 H), 7.296 (t, 1 H, J=7 Hz), 7.233 (t, 2 H, J=7 Hz), 7.139 (t, 1 H, J=7 Hz), 7.077 (d, 2 H, J=7 Hz), 6.515 (bs, 1 H), 4.365–4.300 (m, 1 H), 3.335–3.308 (m, 2 H), 3.024 –2.924 (m, 4 H), 2.624–2.548 (m, 1 H), 2.341–2.265 (m, 1 H), 2.156–2.061 (m, 2 H), 1.763–1.737 (m, 2 H), 1.201–1.180 (m, 6 H).

EXAMPLE 133

6-(2-Benzo[1,3]dioxol-5-yl-ethyl)-5,6-dihydro-4-hydroxy-6-phenyl-3-[(2-isopropyl-5-methyl-phenylthio]-2H-pyran-2-one (+/–), The title compound was prepared as described in General Method iii using 400 mg of 6-(2-benzo[1,3]dioxol-5.-yl-ethyl)-5,6-dihydro-4-hydroxy-6-phenyl-2H-pyran-2-one, 415 mg of toluene-4-thiosulfonic acid S-(2-isopropyl-5-methylphenyl) ester and 0.17 ml of triethylamine in 20 ml of absolute ethanol. The solution was stirred overnight at room temperature. Purification by flash chromatography using hexanes/isopropanol (90/10 to 50/50) as eluent gave a solid (mp=83°–85° C.) $^1$H NMR (CDCl$_3$) d 1.21 (d, 3 H), 1.25 (d, 3 H), 1.93 (s, 3 H), 2.20–2.40 (m, 3 H), 2.60–2.75 (m, 1 H), 3.30 (dd, 2 H), 3.42 (q, 1 H), 5.89 (s, 2 H), 6.11 (s, 1 H), 6.52 (d, 1 H), 6.56 (s, 1 H), 6.69 (d, 1 H), 6.87 (d, 1 H), 7.07 (d, 1 H), 7.30–7.50 (m, 5 H), 7.64 (br.s, 1 H).

4.3 DETERMINATION OF HIV PROTEASE INHIBITION

4.3.1 STARTING MATERIALS

DTT Buffer 1.0 mM dithiothreitol (DTT) was prepared fresh daily in 0.1% polyethylene glycol (mw 8000) 80 mM NaOAc, 160 mM NaCl, 1.0 mM EDTA, and brought to pH 4.7 with HCl.

HIV-1 Protease

The enzyme is obtained from Bachem Bioscience Inc. The undiluted enzyme is thawed from −80° C. and diluted 50-fold with DTT buffer. The solution is always kept at 0° C. on ice water and used in the experiment within 20 minutes after thawing.

Enzyme Substrate

Substrate III from Bachem Bioscience Inc. is the undecapeptide H-His-Lys-Ala-Arg-Val-Leu-p-Nitrophenylalanine-Glu-Ala-Norleucine-Ser-NH2 (>97% purity). A 200 μM stock solution in DTT buffer is prepared and stored on ice. Substrate solution is prepared fresh daily.

Test Compound 10 mM inhibitor (I) in dimethyl sulfoxide (DMSO) is diluted to 200 μM with DTT buffer. From the 200 μM stock solution is made a 10 μM stock solution with 2% DMSO in DTT buffer. The two inhibitor solutions are used to make final [I]=100, 50, 20, 10, 5, 2, 1, 0.5 and 0 μM with 2% DMSO in DTT buffer in each reaction well (total inhibitor volume of 50 μl).

4.3.2 ASSAY

To each reaction well is added 20 μl of substrate (final concentration of 40 μM), 50 μl of inhibitor (at a concentration such that final dilution will produce the test concentration) and 20 μl of DTT buffer. The reaction plate (96 wells) is incubated at 37° C. for at least 5 minutes.

10 μl of the diluted protease is added to the reaction well while the reaction plate is shaking. Once shaken for 10 is returned to the heating block at 37° C. (final reaction volume 100 μl.)

The reaction is incubated for 5 minutes at 37° C. The reaction is stopped by placing the reaction plate on the shaker and adding 20 μl of 10% trifluoroacetic acid (TFA) and shaking for 10 seconds. The amount of proteolysis is then determined by separation of noncleaved substrate and two cleaved products with reverse-phase HPLC, while measuring absorbance at 220 nm to determine the relative peak areas of the three components. The relative peak areas are used to calculate % conversion to product as a function of inhibitor concentration. The data are plotted as % Control (the ratio of % conversion in the presence and absence of inhibitor×100) versus inhibitor concentration and fitted with the equation $Y=100/1+(X/IC_{50})^A$, where $IC_{50}$ is the inhibitor concentration 50% inhibition and A is the slope of the inhibition curve. The results are listed in Table I.

TABLE I

HIV PROTEASE INHIBITION RESULTS

| EXAMPLE | 50% INHIBITION CONCENTRATION [μM] |
|---|---|
| 2 | 1.9 |
| 5 | 0.40 |
| 14 | 2.5 |
| 22 | 1.1 |
| 29 | 0.26 |
| 35 | 0.12 |
| 37 | 0.26 |
| 39 | 0.050 |
| 40 | 0.060 |
| 44 | 0.32 |
| 50 | 0.088 |
| 52 | 2.0 |
| 56 | 0.005 |
| 57 | 0.65 |
| 61 | 0.22 |
| 66 | 0.39 |
| 70 | 0.11 |
| 71 | 0.10 |
| 75 | 0.028 |
| 90 | 0.14 |
| 92 | 0.27 |
| 94 | 0.22 |
| 95 | 1.09 |
| 107 | 0.110 |
| 114 | 0.079 |
| 119 | 0.097 |

ANTI-HIV-1 ACTIVITY

Using the general methods of Pauwels et al., (*J. Virol. Methods*, 16, 171–185, 1987) and Mann et al. (*AIDS Research and Human Retroviruses*, 253–255, 1989 (antiviral assays of actue HIV-1 infection were performed in the H9 cell line. Cultures were batch infected in 1 ml of RPM1 1640 media/10% fetal calf serum containing $10^5$ infectious doses of $HIV1_{iiib}$ for an effective multiplicity of infection of 0.01. After 2 hours of viral absorption, cells were washed once and palted in 96-wellmicrotiter plates at a density of $10^4$ cells per well. Test compounds were added to produce the desired concentration of drug and 0.1% DMSO in a final volume of 200 μl. Uninfected parallel cultures were maintained for XTT cytotoxicity assay at 7 days post infection. Cultures were tested for viral replication by reverse transcriptase assay at 4 and 7 days post infection.

ANTIVIRAL ACTIVITY IN H9 CELLS

| Example # | Concentration for 50% Protection [μM] |
|---|---|
| 94 | 29 |
| 95 | 39 |
| 107 | 8 |
| 114 | 26 |
| 119 | 59 |

Combinations of protease inhibitor with other AIDS treatments, such as (but not limited to) the HIV reverse transcriptase inhibitors AZT or ddC, may produce synergistic results. J. C. Craig et al., *Antiviral Chem. Chemother.*, 4/3: 161–166 (1993); E. V. Connell et al., *Antimicrob. Agents Chemother.*, 38: 348–352 (1994); D. M. Lambert et al., *Antiviral Res.*, 21: 327–342 (1993); A. M. Caliendo et al., *Clin. Infect. Dis.*, 18/4: 516–524 (1994).

The compounds of the invention display antibacterial activity when tested by the microtitration dilution method as described in Heifetz, et al., *Antimicr. Agents. & Chemoth.* 6:124 (1974) which is incorporated herein by reference.

By use of the above referenced method, the following minimum inhibitory concentration values (MICs in μg/mL) were obtained for representative compounds of the invention vs. clinically relevant gram positive pathogens which have become highly resistant to conventional therapy in recent years.

ANTIBACTERIAL ACTIVITY μg/ml

|  | Ex. 65 | Ex. 114 | Ex. 122 |
|---|---|---|---|
| Staphylococcus aureus H228 | 25 | 50 | 12.5 |
| Staphylococcus aureus UC-76 | 25 | 50 | 12.5 |
| Enterococcus foecalis MGH2 | 100 | >100 | >100 |
| Streptococcus pneumonia 5V-1 | 25 | 12.5 | 12.5 |
| Streptococcus pyogenes C203 | 25 | 50 | 25 |

It should be apparent to those skilled in the art that other compositions not specifically disclosed in the instant specification are, nevertheless, contemplated thereby. Such other compositions are considered to be within the scope and spirit of the present invention. Hence, the invention should not be limited by the description of the specific embodiments disclosed herein but only by the following claims.

What is claimed is:

1. A compound or a pharmaceutically acceptable salt thereof of formula

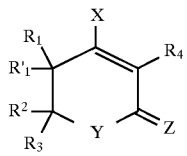

1 wherein

X is $OR_5$, $NHR_5$, $CH_2OR_5$, $CO_2R_6$, or $SR_5$, wherein $R_5$ is $R_6$ or $COR_6$ wherein $R_6$ is independently H, a straight chain alkyl group containing 1 to 6 carbon atoms, a branched or cyclic alkyl group containing 3 to 7 carbon atoms, an alkylcycloalkyl group of 5–9 carbon atoms, benzyl, phenyl, or a heterocycle;

Z is O or S;

Y is O, or S $R_1$ and $R_1'$ are each independently $[CH_2]_{n1}$-$[W_1]_{n2}$-$[Ar]_{n2}$-$[CH_2]_{n3}$-$[W_2]_{n4}$-$R_7$;

$R_2$ is independently selected from the group of structures from which $R_1$ is selected with the proviso that if $W_1$ is a heteroatom n1 is an integer of from 1 to 4;

$R_3$ is independently selected from the group of structures from which $R_1$ is selected with the proviso that if $W_1$ is a heteroatom n1 is an integer of from 1 to 4;

$R_2$ and $R_3$ may be taken together to form an unsubstituted or substituted 3-, 4-, 5-, 6-, or 7-membered ring, wherein the substituents are one or more of the $R_7$ groups listed below;

$R_4$ is $[CH_2]_{n1}$-$[W_3]_{n2}$-$[W_4]_{n4}$-$[Ar]_{n2}$-$[CH_2]_{n3}$-$[W_2]_{n4}$-$R_7$;

n1, n2, n3, n4, and n5 are independently integers of from 0 to 4, 0 to 1, 0 to 4, 0 to 1, and 0 to 2, respectively;

$W_1$, $W_2$ and $W_4$ are independently O, $OCONR_7$ $S(O)_{n5}$, CO, C(=$NR_7$)$NR_7$, $CR_7$=$CR_7$, C=C, $NR_7$, CS, C=N—$R_7$, C=$NOR_7$, $NR_7SO_2$, $SO_2NR_7$, C=C($R_7$)$_2$,$CR_7N(R_7)_2$, $CR_7OR_7$, C($R_7$)$_2$, $NCO_2R_7$, $NR_7CO_2$, $CO_2$, $NCON(R_7)_2$, $NR_7CONR_7$, $NCOR_7$, $NR_7CO$, or $CONR_7$;

$W_3$ is independently selected from the group of structures from which $W_1$ is selected, with the further limitation that if n1 in $R_4$ is zero, that $W_3$ is selected from the group of structures consisting of —CO, —$CR_7$=$CR_7$, —C≡C, —CS, —C=N—$R_7$, —C=$NOR_7$, —$CR_7N(R_7)_2$, —C=C($R_7$)$_2$, —$CR_7OR_7$, —C($R_7$)$_2$, —$CO_2$, and —$CONR_7$, $R_7$ is independently H, Ar, a straight or branched alkyl or alkenyl group containing from 1 to 6 carbon atoms, or two $R_7$ groups can be taken together to form a ring of 3–7 atoms, or a substituted derivative thereof wherein the substituents are one or more of $CO_2R_6$, $COR_6$, $CON(R_6)_2$, $NR_6CON(R_6)_2$, $NR_6COR_6$, $OR_6$, $S(O)_{n5}R_6$, $N(R_6)_2$, Cl, Br, F, $CF_3$, Ar, OAr, or $S(O)_{n5}$Ar;

Ar is independently phenyl, naphthyl, a 5- or 6-membered heterocycle containing 1 to 4 heteroatoms, a cycloalkyl containing 3 to 6 atoms, a fused ring system containing 8–10 atoms, or a substituted derivative thereof wherein the substituents are of F, Cl, Br, CN, $NO_2$, $(CH2)_{n6}R_6$, (CH2) $_{n6}$C(Me)=$CH_2$, $(CH_2)_{n6}N(R_6)_2$, $(CH_2)_{n6}NR_6CON(R_6)_2$, $(CH_2)_{n6}NR_6COR_6$, $(CH_2)_{n6}OR_6$, $(CH_2)_{n6}OCOR_6$, $(CH_2)_{n6}OCON(R_6)_2$, $(CH_2)_{n6}CO_2R_6$, $(CH_2)_{n6}CON(R_6)_2$, $(CH_2)_{n6}COR_6$, $CF_3$, $(CH_2)_{n6}S(O)_{n5}R_6$, $OCH_2O$, or $O(CH_2)_2O$; and n6 is independently an integer of from 0 to 3.

2. A compound of the formula of claim 1 wherein X is OH, $NH_2$, or SH;
Z is O;
Y is S; and
$R_1$ and $R_1'$ are H.

3. A compound of the formula of claim 1 wherein $R_4$ is

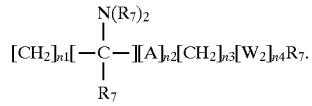

4. A compound of the formula of claim 1 wherein $R_4$ is

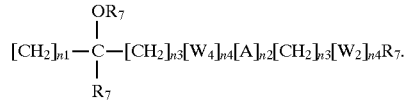

5. A compound of the formula of claim 1 wherein $W_3$ is selected from the group consisting of $CR_7$=$CR_7$, —C≡C—, and C($R_7$)2.

6. A compound of the formula of claim 5 selected from the group consisting of 5,6-Dihydro-4-hydroxy-6-phenyl-6-(2-phenylethyl)-3-[[3-(phenylmethoxy)phenyl]methyl]-2H-pyran-2-one;

5,6-Dihydro-4-hydroxy-6-(3-methylbutyl) -3-[5-methyl-1-(phenylmethyl)hexyl]-6-phenyl-2H-pyran-2-one;

3-[1-(Cyclohexylthio)-5-methylhexyl]-5,6-dihydro-4-hydroxy-6-(3-methylbutyl)-6-phenyl-2H-pyran-2-one;

3-[2-Cyclohexyl-1-[(3-methylbutyl)amino]ethyl]-5,6-dihydro-4-hydroxy-6-(3-methylbutyl) -6-phenyl-2H-pyran-2-one;

5,6-Dihydro-4-hydroxy-3-[(2-isopropyl-5-methylphenyl)methyl]-6-(2-phenylethyl)-6-phenyl-2H-pyran-2-one;

5,6-Dihydro-4-hydroxy-3-[(3-hydroxymethyl-2-isopropyl-5-methylphenyl)methyl]-6,6-diphenyl-2H-pyran-2-one;

5,6-Dihydro-4-hydroxy-3-[[4 -(hydroxymethyl)phenyl]methyl]-6-pentyl-6-phenyl-2H-pyran-2-one;

5,6-Dihydro-4-hydroxy-3-[(3-hydroxyphenyl) methyl]-6-(2-phenylethyl)-6-phenyl-2H-pyran-2-one;

5,6-Dihydro-4-hydroxy-6-pentyl-6-phenyl-3-[[4-(pyridin-3-ylmethoxy)phenyl]methyl]-2H-pyran-2-one;

5,6-Dihydro-4-hydroxy-3-[[2-isopropyl-3-[2-(morpholin-4-yl)ethoxy]phenyl]methyl]-6-(2-phenylethyl) -6-phenyl-2H-pyran-2-one;

5,6-Dihydro-4-hydroxy-3-(3-methyl-1-phenyl-but-2-enyl)-6,6-diphenyl-2H-pyran-2-one;

5,6-Dihydro-4-hydroxy-6-(3-methylbutyl)-3-(3-methyl-1-propyl-but-2-enyl)-6-phenyl-2H-pyran-2-one;

5,6-Dihydro-4-hydroxy-3-[[2-(hydroxymethyl)phenyl]methyl]-6-(2-phenylethyl)-6-phenyl-2H-pyran-2-one;

5,6-Dihydro-4-hydroxy-6-(2-phenylethyl)-6-phenyl-3-(2-phenyl-[1,3]dithiolan-2-yl)-2H-pyran-2-one;

4-Hydroxy-3-[2-methoxy(phenyl)methyl]-6-phenyl-6-(2-phenylethyl)-5,6-dihydro-2H-pyran-2-one;

3-[Cyclopentyl (cyclopentyloxy)methyl]-4-hydroxy-6-(2-phenylethyl)-6-propyl-5,6-dihydro-2H-pyran-2-one;

3-(1-Cyclopentyloxy-3-methylbutyl)-4-hydroxy-6-(3-methylbutyl)-6-phenyl-5,6-dihydro-2H-pyran-2-one and 6-Cyclopentyl-3-[cyclopentyl (isopropoxy)methyl]-4-hydroxy-6-(3-methylbutyl)-5,6-dihydro-2H-pyran-2-one.

7. A compound of the formula of claim 1 wherein $R_4$ is —Ar $[CH_2]_{n3}$ $[W_2]_{n4}$ $R_7$ with the limitation that Ar is not a $C_3$—$Cl_5$ spirocycle.

8. A compound of the formula of claim 7 selected from the group consisting of

6-Butyl-3-(3,5-dimethylphenyl)-5,6-dihydro-4-hydroxy-6-phenyl-2H-pyran-2-one;

3-[4-[(Phenylmethoxy)methyl]-1-tert-butyl-1H-imidazol-2-yl]-5,6-dihydro-4-hydroxy-6-(2-phenylethyl)-6-phenyl-2H-pyran-2-one and 3-(1-tert-Butyl-4-methyl-1H-pyrrol-2-yl) -5,6-dihydro-4-hydroxy-6,6-diphenyl-2H-pyran-2-one.

9. A compound of the formula of claim 1 wherein

X is $OR_5$, $NHR_5$, or $SR_5$;

Z is O;

Y is O;

$R_5$ is $COR_6$ or $R_6$; and $R_6$ is a straight chain alkyl group containing 1 to 6 carbon atoms, a branched or cyclic alkyl group containing 3 to 7 carbon atoms, benzyl, or phenyl.

10. A compound of the formula of claim 9 selected from the group consisting of

N-[3-[Cyclopropyl[4-(acetyloxy)-5,6-dihydro-2-oxo-6-phenyl-(2-phenylethyl)-2H-pyran-3-yl]methyl]phenyl] -benzenesulfonamide;

Propanoic acid 5-[cyclopropyl[3-[(phenylsulfonyl) amino]phenyl]methyl]-3,6 -dihydro-6-oxo-2,2-diphenyl-2H-pyran-4-yl ester;

2,2-Dimethylbutanoic acid 3,5-dihydro-6-oxo-2-(2-phenylethyl) -5-(1-phenylpropyl)-2-propyl-2H-pyran-4-yl ester and Benzenacetic acid 5-[cyclopropyl[3-[(ethylsulfonyl) amino]phenyl]methyl]-3,6-dihydro-6-oxo-2-(2-phenylethyl)-2-propyl-2H-pyran-4-yl ester.

11. A pharmaceutical composition for the treatment of infection or disease caused by a retrovirus, which comprises an amount of the compound of claim 1 sufficient to provide an antivirally effective dosage of the compound in the range of about 1 to about 50 mg/kg-day and a pharmaceutically effective carrier.

12. A pharmaceutical composition for the treatment of infection or disease caused by a retrovirus, which comprises an amount of the compound of claim 2 sufficient to provide an antivirally effective dosage of the compound in the range of about 1 to about 50 mg/kg-day and a pharmaceutically effective carrier.

13. A pharmaceutical composition for the treatment of infection or disease caused by a retrovirus, which comprises an amount of the compound of claim 3 sufficient to provide an antivirally effective dosage of the compound in the range of about 1 to about 50 mg/kg-day and a pharmaceutically effective carrier.

14. A method of treatment of infection or disease caused by a retrovirus, which comprises administering to a subject in need of such treatment a composition of claim 1.

15. A method of treatment of infection or disease caused by a retrovirus, which comprises administering to a subject in need of such treatment a composition of claim 1 in combination with an HIV reverse transcriptase inhibitor.

16. A method of treatment of infection or disease caused by a retrovirus, which comprises administering to a subject in need of such treatment a composition of claim 1 in combination with AZT.

17. A method of treatment of infection or disease caused by a retrovirus, which comprises administering to a subject in need of such treatment a composition of claim 1 in combination with ddC.

18. A method of treatment of infection or disease caused by a retrovirus, which comprises administering to a subject in need of such treatment a composition of claim 2.

19. A method of treatment of infection or disease caused by a retrovirus, which comprises administering to a subject in need of such treatment a composition of claim 2 in combination with a HIV reverse transcriptase inhibitor.

20. A method of treatment of infection or disease caused by a retrovirus, which comprises administering to a subject in need of such treatment a composition of claim 1.

21. A method of treatment of infection or disease caused by a retrovirus, which comprises administering to a subject in need of such treatment a composition of claim 1 in combination with a HIV reverse transcriptase inhibitor.

22. A method of treatment of infection or disease caused by a retrovirus, which comprises administering to a subject in need of such treatment a composition of claim 6.

23. A compound or a pharmaceutically acceptable salt thereof of the formula

1 wherein

X is OH or $NH_2$;

Z is O;

Y is O;

$R_1$ and $R'_1$ are each independently $[CH_2]_{n1}$-$[W_1]_{n2}$-$[AR]_{n2}$-$[CH_2]_{n3}$-$[W_2]_{n4}$-$R_7$;

$R_2$ and $R_3$ are each independently $R_1$ which is $[CH_2]_{n1}$-$[W_1]_{n2}$-$[Ar]_{n2}$-$[CH_2]_{n3}$-$[W_2]_{n4}$-$R_7$ with the proviso that if $W_1$ is a heteroatom n1 is an integer of from 1 to 4 and with the further proviso that $R_2$ and $R_3$ are not H;

$R_4$ is $[CH_2]_{n1}$-$[W_3]_{n2}$-$[CH_2]_{n3}$-$[W_4]_{n4}$-$[AR]_{n2}$-$[CH_2]_{n3}$-$[W_2]_{n4}R_7$;

n2, n3, n4 and n5 are independently integers of from 0 to 1, 0 to 4, 0 to 1 and 0 to 2, respectively;

$W_1$, $W_2$ and $W_4$ are independently O, $OCONR_7$, $S(O)_{n5}$, CO, $C(=NR_7)NR_7$, $CR_7=CR_7$, $C\equiv C$, $NR_7$, CS, $C=N-R_7$, $C=NOR_7$, $NR_7SO_2$, $SO_2NR_7$, $C=C(R_7)_2$, $CR_7N(R_7)_2$, $CR_7OR_7$, $C(R_7)_2$, $NCO_2R_7$, $NR_7CO_2$, $CO_2$, $NCON(R_7)_2$, $NR_7CONR_7$, $NCOR_7$, $NR_7CO$, or $CONR_7$;

$W_3$ is selected from a group consisting of CO, $CR_7=CR_7$, $C\equiv C$, CS, $C=N-R_7$, $C=C(R_7)_2$, $C(R_7)_2$, $CR_7OR_7$, $C(R_7)_2$, $-CO_2$, and CONR wherein R7 is independently H, Ar, a straight or branched alkyl or alkenyl group containing from 1 to 6 carbon atoms, or two $R_7$ groups can be taken together to form a ring of 3–7 atoms, or a substituted derivative thereof wherein the substituents are one or more of $CO_2R_6$, $COR_6$, $CON(R_6)_2$, $NR_6CON(R_6)_2$, $NR_6COR_6$, $OR_6$, $S(O)_{n5}R_6$, $N(R_6)_2$, Cl, Br, F, $CF_3$, Ar, OAr, or $S(O)_{n5}Ar$;

Ar is independently phenyl, naphthyl, a 5- or 6-membered heterocycle containing 1 to 4 heteroatoms, a cycloalkyl containing 3 to 6 atoms, a fused ring system containing 8–10 atoms, or a substituted derivative thereof wherein the substituents are of F, Cl, Br, CN, $NO_2$, $(CH_2)_{n6}R_6$, $(CH_2)_{n6}C(Me)=CH_2$, $(CH_2)_{n6}N(R_6)_2$, $(CH_2)_{n6}NR_6CON(R_6)_2$, $(CH_2)_{n6}NR_6COR_6$, $(CH_2)_{n6}OR_6$, $(CH_2)_{n6}OCOR_6$, $(CH_2)_{n6}OCON(R_6)_2$, $(CH_2)_{n6}CO_2R_6$, $(CH_2)_{n6}CON(R_6)_2$, $(CH_2)_{n6}COR_6$, $CF_3$, $(CH_2)_{n6}S(O)_{n5}R_6$, $OCH_2O$, or $O(CH_2)_2O$; and n6 is independently an integer of from 0 to 3.

* * * * *

UNITED STATES PATENT AND TRADEMARK OFFICE
CERTIFICATE OF CORRECTION

PATENT NO. : 5,840,751
DATED : Nov. 24, 1998
INVENTOR(S) : Ellsworth et al.

It is certified that error appears in the above-identified patent and that said Letters Patent is hereby corrected as shown below:

Column 75, line 57, insert --$[CH_2]_{n3}$-- between "$[W_3]_{n2}$" and "$[W_4]_{n4}$".

Column 75, line 61, "C=C" should read --C≡C--.

Column 77, line 32, "$C_3-Cl_5$" should read --$C_3-C_5$--.

Signed and Sealed this

Fourth Day of January, 2000

Attest:

Attesting Officer

*Acting Commissioner of Patents and Trademarks*